(12) United States Patent
Rammensee et al.

(10) Patent No.: US 8,067,529 B2
(45) Date of Patent: Nov. 29, 2011

(54) IMMUNOGENIC T-HELPER EPITOPES FROM HUMAN TUMOUR ANTIGENS AND IMMUNOTHERAPEUTIC METHODS USING SAID EPITOPES

(75) Inventors: Hans-Georg Rammensee, Tübingen-Unterjesingen (DE); Toni Weinschenk, Esslingen (DE); Jörn Dengjel, Tübingen (DE)

(73) Assignee: Immatics Biotechnologies GmbH, Tubingen (DE)

( * ) Notice: Subject to any disclaimer, the term of this patent is extended or adjusted under 35 U.S.C. 154(b) by 964 days.

(21) Appl. No.: 11/664,627

(22) PCT Filed: Sep. 9, 2005

(86) PCT No.: PCT/EP2005/009719
§ 371 (c)(1),
(2), (4) Date: Oct. 2, 2007

(87) PCT Pub. No.: WO2006/037421
PCT Pub. Date: Apr. 13, 2006

(65) Prior Publication Data
US 2009/0317428 A1 Dec. 24, 2009

(30) Foreign Application Priority Data
Oct. 2, 2004 (EP) .................................... 04023546

(51) Int. Cl.
*C07H 21/04* (2006.01)
*C07K 5/00* (2006.01)
*C12N 15/00* (2006.01)
(52) U.S. Cl. ..................... 530/300; 536/23.1; 435/69.1
(58) Field of Classification Search .................. None
See application file for complete search history.

(56) References Cited

U.S. PATENT DOCUMENTS
5,912,167 A * 6/1999 Palmenberg et al. ....... 435/320.1
2003/0194704 A1* 10/2003 Penn et al. .................. 435/6

FOREIGN PATENT DOCUMENTS
WO  WO03042357 A2 * 5/2003
WO  2006/113671    10/2006

OTHER PUBLICATIONS

Ng et al., 2001, Journal of Biol. Chem. vol. 201, pp. 44444-44449).*
Sherman, La et al, 1998, Critical reviews in Immunol, 18(1-2): 47-54.*
Lauritzsen et al (International Journal of Cancer, 1998, vol. 78, pp. 216-222.*
Sarma et al (Journal of Experimental Medicine, 1999, vol. 189, pp. 811-820.*
Harig et al , Blood, 98 (10): 2999-3005, 2001.*
Nolling et al , J Bacteriol, 183:4824838, 2001.*
Dengjel et al., "Identificatin of a naturally . . . spectrometry," Eur. J. Immunol., 2004, pp. 3644-3651, vol. 34, No. 12, XP001206092, Germany.
Malcherek et al., "MHC class II-associated . . . presentation," Eur. J. Immunol., May 1998, pp. 1524-1533, vol. 28, No. 5, XP001206094, GB.
Rammensee et al. "Syfpeithi: database for MHC . . . motifs," Immunogenetics, 1999, pp. 213-219, vol. 50, No. 3-4, XP-002183663, DE.
Hedberg et al., "Expression of cyclin . . . tissue microarray," British Journal of Cancer., 2003, pp. 1417-1423, vol. 88, No. 9, XP001206106, GB.
Chaux et al., "Identification of MAGE-3 . . . Lymphocytes," Jr. Exp. Med., 1999, pp. 767-777, vol. 189, No. 5, XP000857617, Japan.
Ten Bosch et al., "Recognition of BCR-ABL . . . Peptide," Blood, 1996, pp. 3522-2527, vol. 88, No. 9, XP000647337, US.
Fu et al., "Minireview: Cyclin D1:Normal..Functions," Endocrinology, 2004, pp. 5439-5447, vol. 145, No. 12, XP009046546, US.
Borczuk et al., "Molecular Signatures in Biopsy Specimens of Lung Cancer," AJRCCM Articles in Press; Apr. 15, 2004; The American Thoracic Society.
Maeda et al., "Suppressor T cells regulate the nonanergic cell population that remains after peripheral tolerance is induced to the Mls-1 antigen in T cell receptor vβ8.1 transgenic mice," PNAS; Nov. 21, 2000, pp. 13257-13262; vol. 97; No. 24.
Polymenidou et al., "Humoral immune response to native eukaryotic prion protein correlates with anti-prion protection;" PNAS; Oct. 5, 2004; pp. 14670-14676; vol. 101, suppl. 2.
Kurts et al., "CD8 T cell ignorance or tolerance to islet antigens depends on antigen dose," PNAS; Oct. 26, 1999; pp. 12703-12707; vol. 96, No. 22.
Sadovnikova et al., "Peptide-specific cytotoxic T lymphocytes restricted by nonself major histocompatibility complex class I molecules: Reagents for tumor immunotherapy," Proc. Natl. Acad. Sci.; Nov. 1996; pp. 13114-13118; vol. 93; Immunology. Vella et al., "B cells are not essential for peripheral T-cell tolerance," Proc. Natl. Acad. Sci.; Jan. 1996; pp. 951-955; vol. 93; Immunology.
Vidard et al., "Specific T-cell tolerance may be preceded by a primary response," Proc. Natl. Acad. Sci.; Jun. 1994; pp. 5627-5631; vol. 91; Immunology.
Adam Adler, "Peripheral Tolerization of Effector and Memory T Cells: Implications for Autoimmunity and Tumor-Immunity," Curr Immunol Rev.; Jan. 1, 2005; pp. 21-28; 1(1); Bentham Science Publishers Ltd.

(Continued)

*Primary Examiner* — Misook Yu
*Assistant Examiner* — Lei Yao
(74) *Attorney, Agent, or Firm* — Baker Donelson Bearman Caldwell & Berkowitz, PC

(57) ABSTRACT

The present invention relates to immunotherapeutic methods, and molecules and cells for use in immunotherapeutic methods. In particular, the present invention relates to the immunotherapy of cancer, in particular renal cancer. The present invention furthermore relates to tumour-associated T-helper cell peptide epitopes, alone or in combination with other tumour-associated peptides, that serve as active pharmaceutical ingredients of vaccine compositions which stimulate anti-tumour immune responses. In particular, the present invention relates to 338 novel peptide sequences derived from HLA class II molecules of human tumour cell lines which can be used in vaccine compositions for eliciting anti-tumour immune responses.

17 Claims, 8 Drawing Sheets

OTHER PUBLICATIONS

Oehlen et al., "Expression of a Tolerizing Tumor Antigen in Peripheral Tissue Does Not Preclude Recovery of High-Affinity CD8+ T Cells or CTL Immunotherapy of Tumors Expressing the Antigen," J. Immunol.; 2001; pp. 2863-2870; 166; The American Association of Immunologists, Inc., Bethesda, MD.

Mihalyo et al., "In Vivo Cyclophosphamide and IL-2 Treatment Impedes Self-Antigen-Induced Effector CD4 Cell Tolerization: Implications for Adoptive Immunotherapy," J. Immunol.; 2004; pp. 5338-5345; 172; The American Association of Immunologists, Inc., Bethesda, MD.

Basil et al., "Common Cancer Biomarkers," Cancer Res. Mar. 15, 2006; pp. 2953-2961; 66(6).

Hugh McDevitt, "Specific antigen vaccination to treat autoimmune disease," PNAS; Oct. 5, 2004; pp. 14627-14630; vol. 101, suppl. 2; The National Academy of Sciences of the USA.

"Search of: Immunotherapy Vaccine," ClinicalTrials.gov; Aug. 9, 2010; (http://clinicaltrials.gov/ct2/results?term=Immunotherapy+Vaccine).

* cited by examiner

A

B

IMMUNOGENIC T-HELPER EPITOPES FROM HUMAN TUMOUR ANTIGENS AND IMMUNOTHERAPEUTIC METHODS USING SAID EPITOPES

CROSS-REFERENCE TO A RELATED APPLICATION

This application is a National Stage Application of International Application Number PCT/EP2005/009719, filed Sep. 9, 2005; which claims priority to European Application No. 04023546.7, filed Oct. 2, 2004.

The present invention relates to immunotherapeutic methods, and molecules and cells for use in immunotherapeutic methods. In particular, the present invention relates to the immunotherapy of cancer, in particular renal cancer. The present invention furthermore relates to tumour-associated T-helper cell peptide epitopes, alone or in combination with other tumour-associated peptides, that serve as active pharmaceutical ingredients of vaccine compositions which stimulate anti-tumour immune responses. In particular, the present invention relates to 338 novel peptide sequences derived from HLA class II molecules of human tumour cell lines which can be used in vaccine compositions for eliciting anti-tumour immune responses.

For the purposes of the present invention, all references as cited herein are incorporated by reference in their entireties.

BACKGROUND OF THE INVENTION

Stimulation of an immune response is dependent upon the presence of antigens recognised as foreign by the host immune system. The discovery of the existence of tumour associated antigens has now raised the possibility of using a host's immune system to intervene in tumour growth. Various mechanisms of harnessing both the humoral and cellular arms of the immune system are currently being explored for cancer immunotherapy.

Specific elements of the cellular immune response are capable of specifically recognising and destroying tumour cells. The isolation of cytotoxic T cells (CTL) from tumour-infiltrating cell populations or from peripheral blood suggests that such cells play an important role in natural immune defenses against cancer (Cheever et al., Annals N.Y. Acad. Sci. 1993 690:101-112). $CD8^+$ T-cells ($TCD8^+$) in particular, which recognise Class I molecules of the major histocompatibility complex (MHC)-bearing peptides of usually 8 to 10 residues derived from proteins located in the cytosols, play an important role in this response. The MHC-molecules of the human are also designated as human leukocyte-antigens (HLA).

There are two classes of MHC-molecules: MHC-I-molecules, that can be found on most cells having a nucleus that present peptides that result from proteolytic cleavage of endogenous proteins and larger peptides. MHC-II-molecules can be found only on professional antigen presenting cells (APC), and present peptides of exogenous proteins that are taken up by APCs during the course of endocytosis, and are subsequently processed. Complexes of peptide and MHC-I are recognised by CD8-positive cytotoxic T-lymphocytes, complexes of peptide and MHC-II are recognised by $CD4^+$-helper-T-cells.

In order for a peptide to trigger (elicit) a cellular immune response, it must bind to an MHC-molecule. This process is dependent on the allele of the MHC-molecule and specific polymorphisms of the amino acid sequence of the peptide. MHC-class-I-binding peptides are usually 8-10 residues in length and contain two conserved residues ("anchor") in their sequence that interact with the corresponding binding groove of the MHC-molecule.

There are now numerous examples of both mouse and human $TCD8^+$ that specifically recognise tumour cells and have therapeutic activity after adoptive transfer, in some cases inducing complete remission. However, despite the potential for T cells to eradicate tumours, it is obvious from the progressive growth of most cancers that many tumours escape recognition by TCD8+ in vivo. Though a variety of tumours have been found to be immunogenic, stimulation of an effective antitumour immune response has been difficult to demonstrate.

The antigens that are recognised by the tumour specific cytotoxic T-lymphocytes, that is, their epitopes, can be molecules derived from all protein classes, such as enzymes, receptors, transcription factors, etc. Furthermore, tumour associated antigens, for example, can also be present in tumour cells only, for example as products of mutated genes. Another important class of tumour associated antigens are tissue-specific structures, such as CT ("cancer testis")-antigens that are expressed in different kinds of tumours and in healthy tissue of the testis.

Various tumour associated antigens have been identified. Further, much research effort is being expended to identify additional tumour associated antigens. Some groups of tumour associated antigens, also referred to in the art as tumour specific antigens, are tissue specific. Examples include, but are not limited to, tyrosinase for melanoma, PSA and PSMA for prostate cancer and chromosomal cross-overs such as bcr/abl in lymphoma. However, many tumour associated antigens identified occur in multiple tumour types, and some, such as oncogenic proteins and/or tumour suppressor genes (tumour suppressor genes are, for example reviewed for renal cancer in Linehan W M, Walther M M, Zbar B. The genetic basis of cancer of the kidney. J Urol. 2003 December; 170(6 Pt 1):2163-72) which actually cause the transformation event, occur in nearly all tumour types. For example, normal cellular proteins that control cell growth and differentiation, such as p53 (which is an example for a tumour suppressor gene), ras, c-met, myc, pRB, VHL, and HER-2/neu, can accumulate mutations resulting in upregulation of expression of these gene products thereby making them oncogenic (McCartey et al. Cancer Research 1998 15:58 2601-5; Disis et al. Ciba Found. Symp. 1994 187:198-211). These mutant proteins can be the target of a tumour specific immune response in multiple types of cancer.

A tumour suppressor gene is a gene that reduces the probability that a cell in a multicellular organism will turn into a tumour cell. A mutation or deletion of such a gene will increase the probability of a tumour. In that way, a tumour suppressor gene is similar to an oncogene. Tumour suppressor genes, or more precisely, the proteins they code for, have a dampening or repressive effect on the regulation of the cell cycle. This is basically done by the tumour suppression genes/proteins in three ways: 1. Repression of genes that are essential for the continuing of the cell cycle. If these genes are not expressed, the cell cycle will not continue, effectively inhibiting cell division. 2. Coupling the cell cycle to DNA damage. As long as there is damaged DNA in the cell, it should not divide. If the damage can be repaired, the cell cycle can continue. 3. If the damage can not be repaired, the cell should initiate apoptosis, the programmed cell death, to remove the threat it poses for the greater good of the organism. The first tumour suppressor protein discovered was the pRb protein in human retinoblastoma. An important tumour suppressor is the p53 gene (see above).

Transforming proteins from oncogenic viruses such as E6 and E7 from HPV or EBNA1 from Epstein Barr virus (EBV) also occur in many tumour types and can be the target of a tumour specific immune response in multiple types of cancer (McKaig et al. Head Neck 1998 20(3):250-65; Punwaney et al. Head Neck 1999 21(1):21-9; Serth et al. Cancer Res. 1999 15:59(4):823-5; Pagano, J. S. Proc. Assoc. Am. Physicians 1999 111(6):573-80). Non-oncogenic host proteins such as MAGE and MUC family are also ubiquitous. Specifically, the MAGE family of antigens have been found in many different cancers including breast cancer, lung cancer, esophageal cancer, hepatic cancer, thyroid cancer, neuroblastoma, gastric cancer, multiple myeloma and melanoma (Gillespie, A. M. and Coleman, R. E. Cancer Treat. Rev. 1999 25(4):219-27). The MUC family of antigens has been associated with ovarian and endometrial cancer, breast cancer, multiple myeloma, pancreatic cancer, and colon and rectal cancer (Segal-Eiras, A. and Croce, M. V. Allergol. Immunopathol. 1997 25(4):176-81).

Further, most cancers are associated with more than one antigen. Examples of tumours that express more than one tumour antigen include, but are not limited to, breast cancer which has been shown to be associated with MUC-1, HER-2/neu, MAGE, p53, T/Tn and CEA, colon cancer which has been shown to be associated with MUC-2 and MUC-4, CEA, p53 and the MAGE family, melanoma which has been shown to be associated with members of the MAGE family, MART-1 and gp100, and prostate cancer which has been associated with GM2, Tn, sTn, Thompson-Friedenreich antigen (TF), MUC1, MUC2, the beta chain of human chorionic gonadotropin (hCG beta), HER2/neu, PSMA and PSA. In fact, panels of antigens have been suggested for use in immunotherapy against cancer to compensate for the fact that antigen-loss variants of the tumours can grow out under immune system pressure (Zhang et al. Clin. Cancer Res. 1998 4:2669; Kawashima et al. Hum. Immunol. 1998 59:1).

In order for the proteins to be recognised by the cytotoxic T-lymphocytes as tumour-specific antigen, and in order to be used in a therapy, particular prerequisites must be fulfilled. The antigen should be expressed mainly by tumour cells and not by normal healthy tissues or in rather small amounts. It is furthermore desirable, that the respective antigen is not only present in one type of tumour, but also in high concentrations (e.g. copy numbers per cell). Essential is the presence of epitopes in the amino acid sequence of the antigen, since such peptide ("immunogenic peptide") that is derived from a tumour associated antigen should lead to an in vitro or in vivo T-cell-response.

Until now, numerous strategies to target antigens into the class II processing pathway have been described. It is possible to incubate antigen presenting cells (APCs) with the antigen of interest in order to be taken up and processed (Chaux, P., Vantomme, V., Stroobant, V., Thielemans, K., Corthals, J., Luiten, R., Eggermont, A. M., Boon, T. & van der, B. P. (1999) *J. Exp. Med.* 189, 767-778). Other strategies use fusion proteins which contain lysosomal target sequences. Expressed in APCs, such fusion proteins direct the antigens into the class II processing compartment (Marks, M. S., Roche, P. A., van Donselaar, E., Woodruff, L., Peters, P. J. & Bonifacino, J. S. (1995) *J. Cell Biol.* 131, 351-369, Rodriguez, F., Harkins, S., Redwine, J. M., de Pereda, J. M. & Whitton, J. L. (2001) *J. Virol.* 75, 10421-10430).

T-helper cells play an important role in orchestrating the effector function of CTLs in anti-tumour immunity. T-helper cell epitopes that trigger a T-helper cell response of the Th1 type support effector functions of CD8+ Killer T-cells, which include cytotoxic functions directed against tumour cells displaying tumour-associated peptide/MHC complexes on their cell surfaces. In this way tumour-associated T-helper cell peptide epitopes, alone or in combination with other tumour-associated peptides, can serve as active pharmaceutical ingredients of vaccine compositions which stimulate anti-tumour immune responses.

The major task in the development of a tumour vaccine is therefore the identification and characterisation of novel tumour associated antigens and immunogenic T-helper epitopes derived therefrom, that can be recognised by $CD4^{++}$ CTLs. It is therefore an object of the present invention, to provide novel amino acid sequences for such peptide that has the ability to bind to a molecule of the human major histocompatibility complex (MHC) class-II.

According to the present invention, this object is solved by providing a tumour associated peptide that is selected from the group of peptides comprising at least on sequence according to any of SEQ ID No. 1 to SEQ ID No. 338 of the attached sequence listing, wherein the peptide has the ability to bind to a molecule of the human major histocompatibility complex (MHC) class-II.

The present invention further relates to 338 novel peptide sequences derived from HLA class II molecules of human tumour cell lines, in particular renal cancer cell lines, which can be used in vaccine compositions for eliciting anti-tumour immune responses. The novel peptide sequences have been identified by a new and generally applicable combined approach for the identification of unknown naturally processed HLA class II ligands of defined—e.g. tumour associated—antigens. Thus, new and promising candidates for peptide-based immunotherapy have been identified in a manner that includes selection of tumour antigens of outstanding interest and careful determination of peptide sequences derived thereof.

A first aspect of the invention provides a peptide, comprising an amino acid sequence according to any of SEQ ID No. 1 to SEQ ID No. 338 or a variant thereof provided that the peptide is not the intact human polypeptide from which the amino acid sequence is derived (i.e. one of the full-length sequences as listed in the locus link IDs (Accession numbers, see the attached table, below).

As described herein below, the peptides that form the basis of the present invention have all been identified as being presented by MHC class II bearing cells (Awells cells). Thus, these particular peptides as well as other peptides containing the sequence (i.e. derived peptides) will most likely all elicit a specific T-cell response, although the extent to which such response will be induced might vary from individual peptide to peptide. Differences, for example, could be caused due to mutations in said peptides (see below). The person of skill in the present art is well aware of methods that can be applied in order to determine the extent to which a response is induced by an individual peptide, in particular with reference to the examples herein and the respective literature.

Preferably, a peptide according to the present invention consists essentially of an amino acid sequence according to any of SEQ ID No. 1 to SEQ ID No. 338 or a variant thereof.

"Consisting essentially of" shall mean that a peptide according to the present invention, in addition to the sequence according to any of SEQ ID No. 1 to SEQ ID No. 338 or a variant thereof, contains additional N- and/or C-terminally located stretches of amino acids that are not necessarily forming part of the peptide that functions as core sequence of the peptide comprising the binding motif and as an immunogenic T-helper epitope.

Nevertheless, these stretches can be important in order to provide for an efficient introduction of the peptide according to the present invention into the cells. In one embodiment of the present invention, the peptide of the present invention comprises the 80 N-terminal amino acids of the HLA-DR antigen-associated invariant chain (p33, in the following "Ii") as derived from the NCBI, GenBank Accession-number X00497 (Strubin, M., Mach, B. and Long, E. O. The complete sequence of the mRNA for the HLA-DR-associated invariant chain reveals a polypeptide with an unusual transmembrane polarity EMBO J. 3 (4), 869-872 (1984)).

By a "variant" of the given amino acid sequence we mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence. For example, a peptide may be modified so that it at least maintains, if not improves, the ability to interact with and bind a suitable MHC molecule, such as HLA-DR, and so that it at least maintains, if not improves, the ability to generate activated CTL which can recognise and kill cells which aberrantly express a polypeptide which contains an amino acid sequence as defined in the aspects of the invention. As can derived from the database as described in the following, certain positions of HLA-DR binding peptides are typically anchor residues forming a core sequence fitting to the binding motif of the HLA binding groove. Modifications of these and other residues involved in binding HLA-DR may enhance binding without altering CTL recognition.

Those amino acid residues that are not essential to interact with the T cell receptor can be modified by replacement with another amino acid whose incorporation does not substantially effect T cell reactivity and does not eliminate binding to the relevant MHC. Thus, apart from the proviso given, the peptide of the invention may be any peptide (by which term we include oligopeptide or polypeptide) which includes the amino acid sequences or a portion or variant thereof as given.

It is furthermore known for MHC-class II presented peptides that these peptides are composed of a "core sequence" having a certain HLA-specific amino acid motif and, optionally, N- and/or C-terminal extensions which do not interfere with the function of the core sequence (i.e. are deemed as irrelevant for the interaction of the peptide and the T-cell). The N- and/or C-terminal extensions can be between 1 to 10 amino acids in length, respectively. Thus, a preferred peptide of the present invention exhibits an overall length of between 9 and 30 amino acids. These peptide can be used either directly in order to load MHC class II molecules or the sequence can be cloned into the vectors according to the description hereinbelow. As these peptides form the final product of the processing of larger peptides within the cell, longer peptides can be used as well. The peptides of the invention may be of any size, but typically they may be less than 100 000 in molecular weight, preferably less than 50 000, more preferably less than 10 000 and typically about 5 000. In terms of the number of amino acid residues, the peptides of the invention may have fewer than 1000 residues, preferably fewer than 500 residues, more preferably fewer than 100 residues.

If a peptide which is greater than around 12 amino acid residues is used directly to bind to a MHC molecule, it is preferred that the residues that flank the core HLA binding region are ones that do not substantially affect the ability of the peptide to bind specifically to the binding groove of the MHC molecule or to present the peptide to the CTL. However, as already indicated above, it will be appreciated that larger peptides may be used, especially when encoded by a polynucleotide, since these larger peptides may be fragmented by suitable antigen-presenting cells.

Examples for peptides of MHC ligands, motifs, variants, as well as certain examples for N and/or C-terminal extensions can be, for example, derived from the database SYFPEITHI (Rammensee H, Bachmann J, Emmerich N P, Bachor O A, Stevanovic S. SYFPEITHI: database for MHC ligands and peptide motifs. Immunogenetics. 1999 November; 50(3-4): 213-9. Review.).

As non-limiting examples, certain peptides for HLA-DR in the database are K H K V YACEVTHQG L S S (SEQ ID NO: 339) derived from Ig kappa chain 188-203 (Kovats et al. Eur J. Immunol. 1997 April; 27(4):1014-21); K V Q WKVDNALQS G N S (SEQ ID NO: 340) derived from Ig kappa chain 145-159 (Kovats et al. Eur J. Immunol. 1997 April; 27(4):1014-21), L P R L I AFTSEHSHF (SEQ ID NO: 341) derived from GAD65 270-283 (Endl et al. J Clin Invest. 1997 May 15; 99(10):2405-15) or F FRMVISNPA A T H Q D I D F L I (SEQ ID NO: 342) derived from GAD65 556-575 (Endl et al. J Clin Invest. 1997 May 15; 99(10):2405-15). In addition, peptides can also be derived from mutated sequences of antigens, such as in the case of ATGFKQSSK A L Q R P V A S (SEQ ID NO: 343) derived from bcr-abl 210kD fusion protein (ten Bosch et al. Blood. 1996 Nov. 1; 88(9): 3522-7), G YKVLVLNPS V A A T (SEQ ID NO: 344) derived from HCV-1 NS3 28-41 Diepolder et al. J. Virol. 1997 August; 71(8):6011-9), or FRKQNPDIV I Q Y M D D L Y V G (SEQ ID NO: 345) derived from HIV-1 (HXB2) RT 326-345 (van der Burg et al. J. Immunol. 1999 Jan. 1; 162(1):152-60). All "anchor" amino acids (see Friede et al., Biochim Biophys Acta. 1996 Jun. 7; 1316(2):85-101; Sette et al. J. Immunol. 1993 Sep. 15; 151(6):3163-70; Hammer et al. Cell. 1993 Jul. 16; 74(1):197-203., and Hammer et al. J Exp Med. 1995 May 1; 181(5):1847-55. As examples for HLA-DR4) have been indicated in bold, the putative core sequences have been underlined.

All the above described peptides are encompassed by the term "variants" of the given amino acid sequence.

By "peptide" we include not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) J. Immunol. 159, 3230-3237, incorporated herein by reference. This approach involves making pseudopeptides containing changes involving the backbone, and not the orientation of side chains. Meziere et al (1997) show that, at least for MHC class II and T helper cell responses, these pseudopeptides are useful. Retro-inverse peptides, which contain NH—CO bonds instead of CO—NH peptide bonds, are much more resistant to proteolysis.

Typically, the peptide of the invention is one which, if expressed in an antigen presenting cell, may be processed so that a fragment is produced which is able to bind to an appropriate MHC molecule and may be presented by a suitable cell and elicit a suitable T cell response. It will be appreciated that a fragment produced from the peptide may also be a peptide of the invention. Conveniently, the peptide of the invention contains a portion which includes the given amino acid sequence or a portion or variant thereof and a further portion which confers some desirable property. For example, the further portion may include a further T cell epitope (whether or not derived from the same polypeptide as the first T cell epitope-containing portion) or it may include a carrier protein or peptide. Thus, in one embodiment the peptide of the invention is a truncated human protein or a fusion protein of a protein fragment and another polypeptide portion provided that the human portion includes one or more inventive amino acid sequences.

In a particularly preferred embodiment, the peptide of the invention includes the amino acid sequence of the invention and at least one further T cell epitope wherein the further T cell epitope is able to facilitate the production of a T cell response directed at the type of tumour that aberrantly expresses a tumour-associated antigen. Thus, the peptides of the invention include so-called "beads on a string" polypeptides which can also be used as vaccines.

It will be appreciated from the following that in some applications the peptides of the invention may be used directly (i.e. they are not produced by expression of a polynucleotide in a patient's cell or in a cell given to a patient); in such applications it is preferred that the peptide has fewer than 100 residues.

It is preferred if the peptides of the invention are able to bind to HLA-DR. It is particularly preferred if the peptides bind selectively to HLA-DR4.

The peptides of the invention are particularly useful in immunotherapeutic methods to target and kill cells which aberrantly express polypeptides that form the basis for the present peptides of the invention. Since these specific peptides consisting of the given amino acid sequences bind to HLA-DR it is preferred that the peptides of the invention are ones which bind HLA-DR and when so bound the HLA-DR-peptide complex, when present on the surface of a suitable antigen-presenting cell, is capable of eliciting the production of a CTL which recognises a cell which aberrantly expresses a polypeptide comprising the given amino acid sequence.

In one embodiment of the present invention, the peptide of the present invention comprises the 80 N-terminal amino acids of the HLA-DR antigen-associated invariant chain (p33, in the following "Ii") as derived from the NCBI, GenBank Accession-number X00497 (see also below).

By "aberrantly expressed" we include the meaning that the polypeptide is overexpressed compared to normal levels of expression or that the gene is silent in the tissue from which the tumour is derived but in the tumour it is expressed. By "overexpressed" we mean that the polypeptide is present at a level at least 1.2× that present in normal tissue; preferably at least 2× and more preferably at least 5× or 10× the level present in normal tissue.

Peptides (at least those containing peptide linkages between amino acid residues) may be synthesised by the Fmoc-polyamide mode of solid-phase peptide synthesis as disclosed by Lu et al (1981) J. Org. Chem. 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised.

Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK.

Purification may be effected by any one, or a combination of, techniques such as size exclusion chromatography, ion-exchange chromatography and (usually) reverse-phase high performance liquid chromatography.

Analysis of peptides may be carried out using thin layer chromatography, reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

A further aspect of the invention provides a nucleic acid (e.g. polynucleotide) encoding a peptide of the invention. The polynucleotide may be DNA, cDNA, PNA, CNA, RNA or combinations thereof and it may or may not contain introns so long as it codes for the peptide. Of course, it is only peptides which contain naturally occurring amino acid residues joined by naturally occurring peptide bonds which are encodable by a polynucleotide. A still further aspect of the invention provides an expression vector capable of expressing a polypeptide according to the invention.

A variety of methods have been developed to operably link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or E. coli DNA polymerase I, enzymes that remove protruding, 3'-single-stranded termini with their 3'-5'-exonucleolytic activities, and fill in recessed 3'-ends with their polymerising activities.

The combination of these activities therefore generates blunt-ended DNA segments. The blunt-ended segments are then incubated with a large molar excess of linker molecules in the presence of an enzyme that is able to catalyse the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) Science 239, 487-491. This method may be used for introducing the DNA into a suitable vector, for example by engineering in suitable restriction sites, or it may be used to modify the DNA in other useful ways as is known in the art. In this method the DNA to be enzymatically amplified is flanked by two specific primers which themselves become incorporated into the amplified DNA. The said specific primers may contain restriction endonuclease recognition sites which can be used for cloning into expression vectors using methods known in the art.

The DNA (or in the case of retroviral vectors, RNA) is then expressed in a suitable host to produce a polypeptide comprising the compound of the invention. Thus, the DNA encoding the polypeptide constituting the compound of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. Nos. 4,440,859 issued 3 Apr. 1984 to Rutter et al, 4,530,901 issued 23 Jul. 1985 to Weissman, 4,582,800 issued 15 Apr. 1986 to Crowl, 4,677,063 issued 30 Jun. 1987 to Mark et al, 4,678,751 issued 7 Jul. 1987 to Goeddel, 4,704,362 issued 3 Nov. 1987 to Itakura et al, 4,710,463 issued 1 Dec. 1987 to Murray, 4,757,006 issued 12 Jul. 1988 to Toole, Jr. et al, 4,766,075 issued 23 Aug. 1988 to Goeddel et al and 4,810,648 issued 7 Mar. 1989 to Stalker, all of which are incorporated herein by reference.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus*), plant cells, animal cells and insect cells. Preferably, the system can be Awells cells.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention. Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells. An example of an inducible mammalian expression vector is pMSG, also available from Pharmacia. This vector uses the glucocorticoid-inducible promoter of the mouse mammary tumour virus long terminal repeat to drive expression of the cloned gene. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). Other vectors and expression systems are well known in the art for use with a variety of host cells.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and kidney cell lines. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors.

Transformation of appropriate cell hosts with a DNA construct of the present invention is accomplished by well known methods that typically depend on the type of vector used. With regard to transformation of prokaryotic host cells, see, for example, Cohen et al (1972) Proc. Natl. Acad. Sci. USA 69, 2110 and Sambrook et al (1989) Molecular Cloning, A Laboratory Manual, Cold Spring Harbor Laboratory, Cold Spring Harbor, N.Y. Transformation of yeast cells is described in Sherman et al (1986) Methods In Yeast Genetics, A Laboratory Manual, Cold Spring Harbor, N.Y. The method of Beggs (1978) Nature 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) J. Mol. Biol. 98, 503 or Berent et al (1985) Biotech. 3, 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies. Thus, in addition to the transformed host cells themselves, the present invention also contemplates a culture of those cells, preferably a monoclonal (clonally homogeneous) culture, or a culture derived from a monoclonal culture, in a nutrient medium.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules.

A further aspect of the invention provides a method of producing a peptide for intravenous (i. v.) injection, subcutaneous (s. c.) injection, intradermal (i. d.) injection, intraperitoneal (i. p.) injection, intramuscular (i. m.) injection. Preferred ways of peptide injection are s. c., i. d., i. p., i. m., and i. v. Preferred ways of DNA injection are i. d., i. m., s. c., i. p. and i. v. Doses of between 1 and 500 mg of peptide or DNA may be given.

A further aspect of the invention provides a method of killing target cells in a patient which target cells aberrantly express a polypeptide comprising an amino acid sequence of the invention, the method comprising administering to the patient an effective amount of a peptide according to the invention, or an effective amount of a polynucleotide or an expression vector encoding a said peptide, wherein the amount of said peptide or amount of said polynucleotide or expression vector is effective to provoke an anti-target cell immune response in said patient. The target cell is typically a tumour or cancer cell.

The peptide or peptide-encoding nucleic acid constitutes a tumour or cancer vaccine. It may be administered directly into the patient, into the affected organ or systemically, or applied ex vivo to cells derived from the patient or a human cell line which are subsequently administered to the patient, or used in vitro to select a subpopulation from immune cells derived from the patient, which are then re-administered to the patient. If the nucleic acid is administered to cells in vitro, it may be useful for the cells to be transfected so as to co-express immune-stimulating cytokines, such as interleukin-2.

The peptide may be substantially pure, or combined with an immune-stimulating adjuvant such as Detox, or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and Longenecker et al (1993) Ann. NY Acad. Sci. 690, 276-291). The peptide may also be tagged, or be a fusion protein, or be a hybrid molecule. The peptides whose sequence is given in the present invention are expected to stimulate $CD4^+$ CTL. However, stimulation is more efficient in the presence of help provided by $CD4^+$ T cells. Thus, the fusion partner or sections of a hybrid molecule suitably provide epitopes which stimulate $CD4^+$ T cells. $CD4^+$ stimulating epitopes are well known in the art and include those identified in tetanus toxoid. The polynucleotide may be substantially pure, or contained in a suitable vector or delivery system.

Suitable vectors and delivery systems include viral, such as systems based on adenovirus, vaccinia virus, retroviruses, herpes virus, adeno-associated virus or hybrids containing elements of more than one virus. Non-viral delivery systems include cationic lipids and cationic polymers as are well known in the art of DNA delivery. Physical delivery, such as via a "gene-gun" may also be used. The peptide or peptide encoded by the nucleic acid may be a fusion protein, for example with an epitope from tetanus toxoid which stimulates CD4+ T cells.

The peptide for use in a cancer vaccine may be any suitable peptide. In particular, it may be a suitable 9-mer peptide or a suitable 7-mer or 8-mer or 10-mer or 11-mer peptide or 12-mer. Longer peptides may also be suitable, but 9-mer or 10-mer peptides as described in the attached table 1 are preferred.

Suitably, any nucleic acid administered to the patient is sterile and pyrogen free. Naked DNA may be given intramuscularly or intradermally or subcutaneously. The peptides may be given intramuscularly, intradermally or subcutaneously.

Vaccination results in CTL responses stimulated by professional antigen presenting cells; once CTL are primed, there may be an advantage in enhancing MHC expression in tumour cells.

It may also be useful to target the vaccine to specific cell populations, for example antigen presenting cells, either by the site of injection, use of targeting vectors and delivery systems, or selective purification of such a cell population from the patient and ex vivo administration of the peptide or nucleic acid (for example dendritic cells may be sorted as described in Zhou et al (1995) Blood 86, 3295-3301; Roth et al (1996) Scand. J. Immunology 43, 646-651). For example, targeting vectors may comprise a tissue- or tumour-specific promoter which directs expression of the antigen at a suitable place.

A further aspect of the invention therefore provides a vaccine effective against cancer, or cancer or tumour cells, comprising an effective amount of a peptide according to the invention, or comprising a nucleic acid encoding such a peptide. It is particularly preferred if the vaccine is a nucleic acid vaccine. It is known that inoculation with a nucleic acid vaccine, such as a DNA vaccine, encoding a polypeptide leads to a T cell response.

Conveniently, the nucleic acid vaccine may comprise any suitable nucleic acid delivery means. The nucleic acid, preferably DNA, may be naked (i.e. with substantially no other components to be administered) or it may be delivered in a liposome or as part of a viral vector delivery system.

It is believed that uptake of the nucleic acid and expression of the encoded polypeptide by dendritic cells may be the mechanism of priming of the immune response; however, dendritic cells may not be transfected but are still important since they may pick up expressed peptide from transfected cells in the tissue.

It is preferred if the vaccine, such as DNA vaccine, is administered into the muscle. It is also preferred if the vaccine is administered into the skin. The nucleic acid vaccine may be administered without adjuvant. The nucleic acid vaccine may also be administered with an adjuvant such as BCG or alum. Other suitable adjuvants include Aquila's QS21 stimulon (Aquila Biotech, Worcester, Mass., USA) which is derived from saponin, mycobacterial extracts and synthetic bacterial cell wall mimics, and proprietory adjuvants such as Ribi's Detox. Quil A, another saponin derived adjuvant, may also be used (Superfos, Denmark). It is preferred if the nucleic acid vaccine is administered without adjuvant. Other adjuvants such as Freund's may also be useful. It may also be useful to give the peptide conjugated to keyhole limpet haemocyanin, preferably also with an adjuvant.

Polynucleotide-mediated immunisation therapy of cancer is described in Conry et al (1996) Seminars in Oncology 23, 135-147; Condon et al (1996) Nature Medicine 2, 1122-1127; Gong et al (1997) Nature Medicine 3, 558-561; Zhai et al (1996) J. Immunol. 156, 700-710; Graham et al (1996) Int J. Cancer 65, 664-670; and Burchell et al (1996) pp. 309-313 In: Breast Cancer, Advances in biology and therapeutics, Calvo et al (eds), John Libbey Eurotext, all of which are incorporated herein by reference.

A still further aspect of the present invention provides the use of a peptide according to the invention, or of a polynucleotide or expression vector encoding such a peptide, in the manufacture of a medicament for killing target cells in a patient which target cells aberrantly express a polypeptide comprising an amino acid sequence of the invention.

A further aspect of the invention provides a method for producing activated cytotoxic T lymphocytes (CTL) in vitro, the method comprising contacting in vitro CTL with antigen-loaded human class II MHC molecules expressed on the surface of a suitable antigen-presenting cell for a period of time sufficient to activate, in an antigen specific manner, said CTL wherein the antigen is a peptide according to the invention.

Suitably, the CTL are $CD4^+$ helper cells, preferably of TH1-type. The MHC class II molecules may be expressed on the surface of any suitable cell and it is preferred if the cell is one which does not naturally express MHC class II molecules (in which case the cell is transfected to express such a molecule) or, if it does, it is defective in the antigen-processing or antigen-presenting pathways. In this way, it is possible for the cell expressing the MHC class II molecule to be primed substantially completely with a chosen peptide antigen before activating the CTL.

The antigen-presenting cell (or stimulator cell) typically has an MHC class II molecule on its surface and preferably is substantially incapable of itself loading said MHC class II molecule with the selected antigen. As is described in more detail below, the MHC class II molecule may readily be loaded with the selected antigen in vitro.

Preferably the mammalian cell lacks or has a reduced level or has reduced function of the TAP peptide transporter. Suitable cells which lack the TAP peptide transporter include T2, RMA-S and Drosophila cells. TAP is the Transporter Associated with antigen Processing.

The human peptide loading deficient cell line T2 is available from the American Type Culture Collection, 12301 Parklawn Drive, Rockville, Md. 20852, USA under Catalogue No CRL 1992; the Drosophila cell line Schneider line 2 is available from the ATCC under Catalogue No CRL 19863; the mouse RMA-S cell line is described in Karre and Ljunggren (1985) J. Exp. Med. 162, 1745, incorporated herein by reference.

Conveniently said host cell before transfection expresses substantially no MHC class I molecules. It is also preferred if the stimulator cell expresses a molecule important for T cell costimulation such as any of B7.1, B7.2, ICAM-1 and LFA 3.

The nucleic acid sequences of numerous MHC class II molecules, and of the costimulator molecules, are publicly available from the GenBank and EMBL databases.

In a further embodiment, combinations of HLA molecules may also be used.

The use of recombinant polyepitope vaccines for the delivery of multiple $CD8^+$ CTL epitopes is described in Thomson et al (1996) J. Immunol. 157, 822-826 and WO 96/03144, both of which are incorporated herein by reference. In relation to the present invention, it may be desirable to include in a single vaccine, a peptide (or a nucleic acid encoding a peptide) wherein the peptide includes, in any order, an amino acid sequence of the present invention and a CD4+ T cell-stimulating epitope (such as from tetanus toxoid). Such a vaccine would be particularly useful for treating cancers. Such "bead-on-a-string" vaccines are typically DNA vaccines.

A number of other methods may be used for generating CTL in vitro. For example, the methods described in Peoples et al (1995) Proc. Natl. Acad. Sci. USA 92, 432-436 and Kawakami et al (1992) J. Immunol. 148, 638643 use autologous tumour-infiltrating lymphocytes in the generation of CTL. Plebanski et al (1995) Eur. J. Immunol. 25, 1783-1787 makes use of autologous peripheral blood lymphocytes (PLBs) in the preparation of CTL. Jochmus et al (1997) J. Gen. Virol. 78, 1689-1695 describes the production of autologous CTL by employing pulsing dendritic cells with peptide or polypeptide, or via infection with recombinant virus. Hill et al (1995) J. Exp. Med. 181, 2221-2228 and Jerome et al (1993) J. Immunol. 151, 1654-1662 make use of B cells in the production of autologous CTL. In addition, macrophages pulsed with peptide or polypeptide, or infected with recombinant virus, may be used in the preparation of autologous CTL.

Allogeneic cells may also be used in the preparation of CTL and this method is described in detail in WO 97/26328, incorporated herein by reference. For example, in addition to Drosophila cells and T2 cells, other cells may be used to present antigens such as CHO cells, baculovirus-infected insects cells, bacteria, yeast, vaccinia-infected target cells. In addition plant viruses may be used (see, for example, Porta et al (1994) Virology 202, 449-955 which describes the development of cowpea mosaic virus as a high-yielding system for the presentation of foreign peptides.

The activated CTL which are directed against the peptides of the invention are useful in therapy. Thus, a further aspect of the invention provides activated CTL obtainable by the foregoing methods of the invention.

A still further aspect of the invention provides activated CTL which selectively recognise a cell which aberrantly expresses a polypeptide comprising an amino acid sequence of the invention. Preferably, the CTL recognises the said cell by interacting with the HLA/peptide-complex (for example, binding). The CTL are useful in a method of killing target cells in a patient which target cells aberrantly express a polypeptide comprising an amino acid sequence of the invention wherein the patient is administered an effective number of the activated CTL. The CTL which are administered to the patient may be derived from the patient and activated as described above (i.e. they are autologous CTL). Alternatively, the CTL are not from the patient but are from another individual. Of course, it is preferred if the individual is a healthy individual. By "healthy individual" we mean that the individual is generally in good health, preferably has a competent immune system and, more preferably, is not suffering from any disease which can be readily tested for, and detected.

The activated CTL express a T cell receptor (TCR) which is involved in recognising cells which express the aberrant polypeptide. It is useful if the cDNA encoding the TCR is cloned from the activated CTL and transferred into a further CTL for expression.

In vivo, the target cells for the $CD4^+$ CTL according to the present invention can be cells of the tumour (which sometimes express MHC class II) and/or stromal cells surrounding the tumour (tumour cells) (which sometimes also express MHC class II).

The TCRs of CTL clones of the invention specific for the peptides of the invention are cloned. The TCR usage in the CTL clones is determined using (i) TCR variable region-specific monoclonal antibodies and (ii) RT PCR with primers specific for Vα and Vβ gene families. A cDNA library is prepared from poly-A mRNA extracted from the CTL clones. Primers specific for the C-terminal portion of the TCR a and P chains and for the N-terminal portion of the identified Va and P segments are used. The complete cDNA for the TCR a and chain is amplified with a high fidelity DNA polymerase and the amplified products cloned into a suitable cloning vector. The cloned a and P chain genes may be assembled into a single chain TCR by the method as described by Chung et al (1994) Proc. Natl. Acad. Sci. USA 91, 12654-12658. In this single chain construct the VaJ segment is followed by the V DJ segment, followed by the Cp segment followed by the transmembrane and cytoplasmic segment of the CD3 chain. This single chain TCR is then inserted into a retroviral expression vector (a panel of vectors may be used based on their ability to infect mature human $CD8^+$ T lymphocytes and to mediate gene expression: the retroviral vector system Kat is one preferred possibility (see Finer et al (1994) Blood 83, 43). High titre amphotrophic retrovirus are used to infect purified $CD8^+$ or $CD4^+$ T lymphocytes isolated from the peripheral blood of tumour patients (following a protocol published by Roberts et al (1994) Blood 84, 2878-2889, incorporated herein by reference). Anti-CD3 antibodies are used to trigger proliferation of purified $CD8^+$ T cells, which facilitates retroviral integration and stable expression of single chain TCRs. The efficiency of retroviral transduction is determined by staining of infected $CD8^+$ T cells with antibodies specific for the single chain TCR. In vitro analysis of transduced $CD8^+$ T cells establishes that they display the same tumour-specific killing as seen with the allo-restricted CTL clone from which the TCR chains were originally cloned. Populations of transduced $CD8^+$ T cells with the expected specificity may be used for adoptive immunotherapy of the tumour patients. Patients may be treated with in between $10^8$ to $10^{11}$ autologous, transduced CTL. Analogously to $CD8^+$, transduced $CD4^+$ T helper cells carrying related constructs can be generated.

Other suitable systems for introducing genes into CTL are described in Moritz et al (1994) Proc. Natl. Acad. Sci. USA 91, 4318-4322, incorporated herein by reference. Eshhar et al (1993) Proc. Natl. Acad. Sci. USA 90, 720-724 and Hwu et al (1993) J. Exp. Med. 178, 361-366 also describe the transfection of CTL. Thus, a further aspect of the invention provides a TCR which recognises a cell which aberrantly expresses a polypeptide comprising an amino acid sequence of the invention, the TCR being obtainable from the activated CTL.

As well as the TCR, functionally equivalent molecules to the TCR are included in the invention. These include any molecule which is functionally equivalent to a TCR which can perform the same function as a TCR. In particular, such molecules include genetically engineered three-domain single-chain TCRs as made by the method described by Chung et al (1994) Proc. Natl. Acad. Sci. USA 91, 12654-12658, incorporated herein by reference, and referred to above. The invention also includes a polynucleotide encoding the TCR or functionally equivalent molecule, and an expression vector encoding the TCR or functionally equivalent molecule thereof. Expression vectors which are suitable for expressing the TCR of the invention include those described above in respect of expression of the peptides of the invention.

It is, however, preferred that the expression vectors are ones which are able to express the TCR in a CTL following transfection.

A still further aspect of the invention provides a method of killing target cells in a patient which target cells aberrantly express a polypeptide comprising an amino acid sequence of the invention, the method comprising the steps of (1) obtaining CTL from the patient; (2) introducing into said cells a polynucleotide encoding a TCR, or a functionally equivalent molecule, as defined above; and (3) introducing the cells produced in step (2) into the patient.

A still further aspect of the invention provides a method of killing target cells in a patient which target cells aberrantly express a polypeptide comprising an amino acid sequence as defined in the first or second or third aspects of the invention, the method comprising the steps of (1) obtaining antigen presenting cells, such as dendritic cells, from said patient; (2) contacting said antigen presenting cells with a peptide as defined in the first or second or third aspects of the invention, or with a polynucleotide encoding such a peptide, ex vivo; and (3) reintroducing the so treated antigen presenting cells into the patient.

Preferably, the antigen presenting cells are dendritic cells. Suitably, the dendritic cells are autologous dendritic cells which are pulsed with an antigenic peptide. The antigenic peptide may be any suitable antigenic peptide which gives rise to an appropriate T cell response. T-cell therapy using autologous dendritic cells pulsed with peptides from a tumour associated antigen is disclosed in Murphy et al (1996) The Prostate 29, 371-380 and Tjua et al (1997) The Prostate 32, 272-278.

In a further embodiment the antigen presenting cells, such as dendritic cells, are contacted with a polynucleotide which encodes a peptide of the invention. The polynucleotide may be any suitable polynucleotide and it is preferred that it is capable of transducing the dendritic cell thus resulting in the presentation of a peptide and induction of immunity.

Conveniently, the polynucleotide may be comprised in a viral polynucleotide or virus. For example, adenovirus-transduced dendritic cells have been shown to induce antigen-specific antitumour immunity in relation to MUC1 (see Gong et al (1997) Gene Ther. 4, 1023-1028). Similarly, adenovirus-based systems may be used (see, for example, Wan et al (1997) Hum. Gene Ther. 8, 1355-1363); retroviral systems may be used (Specht et al (1997) J. Exp. Med. 186, 1213-1221 and Szabolcs et al (1997) Blood particle-mediated transfer to dendritic cells may also be used (Tuting et al (1997) Eur. J. Immunol. 27, 2702-2707); and RNA may also be used (Ashley et al (1997) J. Exp. Med. 186, 1177 1182).

It will be appreciated that, with respect to the methods of killing target cells in a patient, it is particularly preferred that the target cells are cancer cells, more preferably renal cancer cells.

It is particularly preferred if the patients who are treated by the methods of the invention have the HLA-DR haplotype. Thus, in a preferred embodiment the HLA haplotype of the patient is determined prior to treatment. HLA haplotyping may be carried out using any suitable method; such methods are well known in the art.

The invention includes in particular the use of the peptides of the invention (or polynucleotides encoding them) for active in vivo vaccination; for manipulation of autologous dendritic cells in vitro followed by introduction of the so-manipulated dendritic cells in vivo to activate CTL responses; to activate autologous CTL in vitro followed by adoptive therapy (i.e. the so-manipulated CTL are introduced into the patient); and to activate CTL from healthy donors (MHC matched or mismatched) in vitro followed by adoptive therapy.

In a preferred embodiment, the vaccines of the present invention are administered to a host either alone or in combination with another cancer therapy to inhibit or suppress the formation of tumours.

The peptide vaccine may be administered without adjuvant. The peptide vaccine may also be administered with an adjuvant such as BCG or alum. Other suitable adjuvants include Aquila's QS21 stimulon (Aquila Biotech, Worcester, Mass., USA) which is derived from saponin, mycobacterial extracts and synthetic bacterial cell wall mimics, and proprietary adjuvants such as Ribi's Detox. Quil A, another saponin derived adjuvant, may also be used (Superfos, Denmark). Other adjuvants such as Freund's or GMCSF may also be useful. It may also be useful to give the peptide conjugated to keyhole limpet haemocyanin, preferably also with an adjuvant.

The peptides according to the invention can also be used as diagnostic reagents. Using the peptides it can be analysed, whether in a CTL-population CTLs are present that are specifically directed against a peptide or are induced by a therapy. Furthermore, the increase of precursor T-cells can be tested with those peptides that have a reactivity against the defined peptide. Furthermore, the peptide can be used as marker in order to monitor the progression of the disease of a tumour that expresses said antigen of which the peptide is derived from.

In the attached table 1 the peptides as identified are listed. In addition, in the table the proteins are designated, from which the peptide is derived, and the respective position of the peptide in the respective protein. Furthermore the respective Acc-Numbers are given that relate to the Genbank of the "National Centre for Biotechnology Information" of the National Institute of Health.

In another preferred embodiment the peptides are used for staining of leukocytes, in particular of T-lymphocytes. This use is of particular advantage if it should be proven, whether in a CTL-population specific CTLs are present that are directed against a peptide. Furthermore the peptide can be used as marker for determining the progression of a therapy in a tumourous disease or disorder.

In another preferred embodiment the peptides are used for the production of an antibody. Polyclonal antibodies can be obtained in a standard fashion by Immunisation of Animals via injection of the peptide and subsequent purification of the immune globulin. Monoclonal antibodies can be produced according to standard protocols such as described, for example, in Methods Enzymol. (1986), 121, Hybridoma technology and monoclonal antibodies.

The invention in a further aspect relates to a pharmaceutical composition, that contains one or more of said peptides according to the invention. This composition is used for parenteral administration, such as subcutaneous, intradermal, intramuscular or oral administration. For this, the peptides are dissolved or suspended in a pharmaceutically acceptable, preferably aqueous carrier. In addition, the composition can contain excipients, such as buffers, binding agents, blasting agents, diluents, flavours, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients, 3. Ed., 2000, American Pharmaceutical Association and pharmaceutical press. The composition can be used for a prevention, prophylaxis and/or therapy of tumourous diseases.

The pharmaceutical preparation, containing at least one of the peptides of the present invention comprising any of the SEQ ID No. 1 to SEQ ID No. 338 is administered to a patient that suffers from a tumourous disease that is associated with the respective peptide or antigen. By this, a CTL-specific immune response can be triggered.

In another aspect of the present invention, a combination of two or several peptides according to the present invention can be used as vaccine, either in direct combination or within the same treatment regimen. Furthermore, combinations with other peptides, for example MHC class I specific peptides can be used. The person of skill will be able to select preferred combinations of immunogenic peptides by testing, for example, the generation of T-cells in vitro as well as their efficiency and overall presence, the proliferation, affinity and expansion of certain T-cells for certain peptides, and the functionality of the T-cells, e.g. by analysing the IFN-γ production (see also examples below). Usually, the most efficient peptides are then combined as a vaccine for the purposes as described above.

A suitable vaccine will contain 2, 3, 4, 5, 6, 7, 8, 9 or 10 different peptides, preferably 4, 5, 6 or 7 different peptides, and most preferably 6 different peptides.

Finally, the vaccine can be dependent from the specific type of cancer that the patient to be treated is suffering from as well as the status of the disease, earlier treatment regimens, the immune status of the patient, and, of course, the HLA-haplotype of the patient.

It has been shown that the 80 N-terminal amino acids of Ii are sufficient to direct proteins into the class II processing pathway (Sanderson, S., Frauwirth, K. & Shastri, N. (1995) *Proc. Natl. Acad. Sci. U.S.A* 92, 7217-7221, Wang, R. F., Wang, X., Atwood, A. C., Topalian, S. L. & Rosenberg, S. A. (1999) *Science* 284, 1351-1354). To deliver an exemplary proof of concept for the present invention, the inventors generated fusion proteins consisting of the 80 N-terminal amino acids of Ii and an exemplary antigen associated with various malignancies, cyclin D1 (CCND1).

Cyclin D1 is a cell cycle regulator involved in the G1-S transition through interactions with cyclin-dependent kinases. Moreover, cyclin D1 is a proto-oncogene and has been shown to be overexpressed in several tumour types (Hedberg, Y., Davoodi, E., Roos, G., Ljungberg, B. & Landberg, G. (1999) *Int. J. Cancer* 84, 268-272, Vasef, M. A., Brynes, R. K., Sturm, M., Bromley, C. & Robinson, R. A. (1999) *Mod. Pathol.* 12, 412-416, —Troussard, X., Avet-Loiseau, H., Macro, M., Mellerin, M. P., Malet, M., Roussel, M. & Sola, B. (2000) *Hematol. J.* 1, 181-185) whereas it is expressed at low level in a large panel of healthy organs and tissues without any particular distribution with the exception of liver and high aortic smooth muscle cells (Weinschenk, T., Gouttefangeas, C., Schirle, M., Obermayr, F., Walter, S., Schoor, O., Kurek, R., Loeser, W., Bichler, K. H., Wernet, D. et al. (2002) *Cancer Res.* 62, 5818-5827). In a differential mass spectrometric approach the inventors compared mass spectra of purified HLA peptides from transfected and non transfected cells and used the resulting peptides of interest in in vitro CD4+ T-helper cell priming experiments in order to prove the immunogenic character of these HLA class II ligands.

The identification of T-helper cell epitopes of tumour associated antigens remains an important task in anti-tumour immunotherapy. Here we report a new and generally applicable method and peptides that have been derived from differential peptide analysis by MS to identify naturally processed and presented MHC class II ligands of tumour associated antigens. This approach combines for the first time a transfection step of APC with a vector encoding for a fusion protein between the Ii chain and the Ag of interest, elution of the HLA-bound peptides and MS identification of the Ag-derived peptides presented by the transfectant by comparison to the non-transfected cells. Moreover, we could validate the method by showing that T cells induced against the identified peptide specifically recognise transfectants overexpressing the cognate Ag. Although the identified peptides still have to be tested for their immunogenicity in vivo, our approach leads to the exact characterisation of naturally processed MHC class II ligands. Thus, the inventors avoid testing either synthetic overlapping peptides of tumour associated antigens, or a broad range of peptides selected by epitope prediction, which is less accurate as compared to class I epitope prediction. In contrast to laborious T-cell assays, which might lead to the identification of cryptic T-cell epitopes unable to induce T-cell activation in vivo (Anderton, S. M., Viner, N. J., Matharu, P., Lowrey, P. A. & Wraith, D. C. (2002) *Nat. Immunol.* 3, 175-181), the work can be focused on the few peptides which are found to be presented. Moreover, using this method it is not necessary to produce the recombinant Ag or to possess Ag-expressing tumour cell lines in order to prove that the peptides are naturally processed.

The inventors used the N-terminus of Ii to direct tumour associated antigens into the class II processing compartment of EBV-transformed B cells. In order to achieve this we constructed a versatile vector with which we can express any antigen as a fusion protein with Ii and which helps us to determine the expression level of the protein in transfected cells by Western blot analysis. It has already been shown that the N-terminus of Ii is sufficient to target proteins into the class II processing compartment. But until now this has only been described in a model using ovalbumin (Sanderson, S., Frauwirth, K. & Shastri, N. (1995) *Proc. Natl. Acad. Sci. U.S.A* 92, 7217-7221), in order to identify unknown Ag using fusion protein-encoding cDNA libraries (Wang, R. F., Wang, X., Atwood, A. C., Topalian, S. L. & Rosenberg, S. A. (1999) *Science* 284, 1351-1354) or to confirm the specificity of known T-cell clones (Chaux, P., Vantomme, V., Stroobant, V., Thielemans, K., Corthals, J., Luiten, R., Eggermont, A. M., Boon, T. & van der, B. P. (1999) *J. Exp. Med.* 189, 767-778). To our knowledge this method has never been used before to identify naturally presented MHC class II bound peptides of known tumour associated antigens. The differential analysis of class II ligands of transfected and non transfected cells by MALDI-MS and the further characterisation of the differentially expressed peptides by ESI-MS results in a straightforward method for identifying class II ligands of antigens of interest. Transfection of cells with keratin 18 fusion proteins proved that our method is generally applicable for antigens of interest, again, we were also able to describe an HLA-DR-presented peptide from a model transgene, keratin 18.

The inventors identified an immunogenic HLA-DR4-presented cyclin D1 peptide antigen having the sequence NPPSMVAAGSVVAAV (SEQ ID No. 1), as well as 337 other HLA class II-associated peptides eluted from a transfected human tumour cell line. The Cyclin D1 peptide and other peptides identified from the human tumour cell line are possible candidates for clinical development of therapeutic vaccines for the treatment of human cancers (Weinschenk, T., Gouttefangeas, C., Schirle, M., Obermayr, F., Walter, S., Schoor, O., Kurek, R., Loeser, W., Bichler, K. H., Wernet, D. et al (2002) *Cancer Res.* 62, 5818-5827).

It should be understood that the features of the invention as disclosed and described herein can be used not only in the respective combination as indicated but also in a singular fashion without departing from the intended scope of the present invention.

The invention will now be described in more detail by reference to the following Figures, the Sequence listing, and the Examples. The following examples are provided for illustrative purposes only and are not intended to limit the invention.

SEQ ID No 1 to SEQ ID No 338 show peptide sequences of T-cell epitope containing peptides that are presented by MHC class II according to the present invention.

SEQ ID No 339 to SEQ ID No 350 show primer sequences as used in the examples.

EXAMPLES

Figure 1:
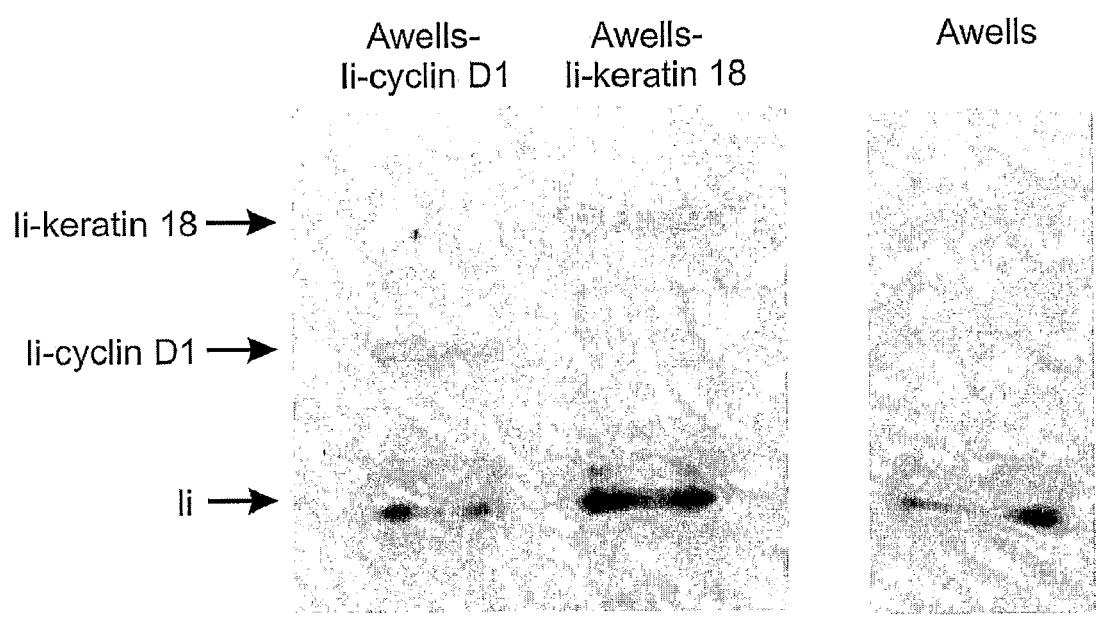
FIG. 1 shows a first Western blot analysis of fusion proteins that have been produced in the course of the experiments.

As will be obvious to those of skill in the art upon this disclosure and the present examples, the invention is also related to other epitopes of tumour associated antigens as specifically used in the following examples that are related to an immunogenic HLA-DR4-presented cyclin D1 peptide antigen having the sequence NPPSMVAAGSVVAAV (SEQ ID No. 1), and keratin 18. The examples are to be seen as general examples and outlines, which can be easily applied by those of skill in the art to all epitopes of tumour associated antigens of the present invention (i.e. comprising any of the sequences of SEQ ID No. 1 to SEQ ID No. 338) in order to fully enable the present invention.

Abbreviations used throughout the present application:
Ab: Antibody
Ag: Antigen
APC: antigen presenting cell
CD: Cluster of Differentiation
cpm: counts per minute
DC: Dendritic Cell EBV: Epstein-Barr Virus
ESI: electrospray ionisation
HLA: Human Leukocyte Antigen
HPLC: High Performance Liquid Chromatography
IFN: Interferon
Ii: invariant chain (CD74)
IL: Interleukin
MALDI: matrix assisted laser desorption/ionisation
MHC: Major Histocompatibility Complex
MS: mass spectrometry
$OD_{450}$: Optical Density at a wavelength of 450 nm
PBMC: Peripheral Blood Mononuclear Cells
PCR: Polymerase Chain Reaction
PHA: Phytohaemagglutinin
SDS-PAGE: Sodium Dodecyl Sulfate Polyacrylamide Gel Electrophoresis
S.I.: stimulation index
TOF: time of flight Cells and Antibodies The human B-lymphoblastoid cell line Awells (IHW-No. 9090; HLA-DRB1*0401, HLA-DRB4*0101) was maintained in RPMI 1640 (C.C.Pro, Neustadt, Germany) medium containing 10% FCS (Pan, Aidenbach, Germany) and supplemented with 2 mM L-glutamine (BioWhittaker, Verviers, Belgium), 100 U/ml penicillin and 100 µg/ml streptomycin (BioWhittaker). In the case of the transfected cell clones 0.8 mg/ml G418 (PAA Laboratories, Linz, Austria) was added. Stable transfectants were generated by electroporation of Awells (280 V, 975 µF; Gene Pulser II, Biorad, München, Germany) cells, followed by cloning using the limiting dilution method. The antibodies L243 (anti-HLA-DR) (Lampson, L. A. & Levy, R. (1980) J. Immunol. 125, 293-299) and W6/32 (anti HLA class I) (Brodsky, F. M. & Parham, P. (1982) J. Immunol. 128, 129-135) were purified from hybridoma culture supernatants using protein A-Sepharose beads (Pharmacia, Uppsala, Sweden). The Th-cell line was induced and cultured in IMDM (BioWhittaker) containing 10% human AB serum (Pel-Freez Clinical Systems, LLC, Milwaukee, Wis., USA) and supplemented with 100 U/ml penicillin and 100 µg/ml streptomycin, 2 mM L-glutamine and 50 µM β-mercaptoethanol. Antibodies used in flow cytometry analysis were from PharMingen (San Diego, Calif., USA).

Plasmid DNA Constructs

The cDNA encoding the 80 N-terminal amino acids of Ii (NCBI, GenBank Accession Number X00497) was amplified in a PCR reaction out of the vector pBluescript II KS(+) 41-1 (Stratagene, Heidelberg, Germany) obtained from A. Melms (Malcherek, G., Wirblich, C., Willcox, N., Rammensee, H. G., Trowsdale, J. & Melms, A. (1998) Eur. J. Immunol. 28, 1524-1533) and subcloned into the Hind III and BamH I sites of pcDNA3 (pcDNA3-Ii; Invitrogen, Karlsruhe, Germany) using the 5' primer ATCGAAGCTTCCAAGATGCACAG-GAGGAGAAGC (SEQ ID NO. 339) and the 3' primer ATCGGGATCCTTTGTCCAGCCGGCCCTGCTG (SEQ ID NO. 340). The genes of interest were amplified in a PCR reaction from cDNA from malignant renal tissue using the 5' primer ATCGGAATTCTGAGCTTCACCACTCGCTCC (SEQ ID NO. 341) and the 3' primer ATCGGCGGCCGCT-TAATGCCTCAGAACTTTGGT (SEQ ID NO. 342) for Keratin 18 (NCBI, GenBank Accession Number X12881) and the 5' primer ATCGGAATTCTGGAACACCAGCTC-CTGTGC (SEQ ID NO. 343) and the 3' primer ATCGGCG-GCCGCTCAGATGTCCACGTCCCGCAC (SEQ ID NO. 344) for Cyclin D1 (NCBI, GenBank X59798), respectively. The obtained cDNA was subcloned using TOPO TA cloning (Invitrogen, Karlsruhe, Germany) and finally inserted into the EcoR I and Not I sites of pcDNA3-Ii, in frame with the Ii sequence.

Real-Time Quantitative PCR

RNA from cells was isolated using TRIzol reagent (Invitrogen, Karlsruhe, Germany) according to the manufacturer's recommendations. cDNA was synthesized from 1 µg of total RNA. Real-time quantitative PCR (qPCR) was performed using the ABI PRISM 7000 Sequence Detection System (Applied Biosystems, Darmstadt, Germany). SYBR Green PCR Master Mix (Applied Biosystems) was used for PCR amplification and real-time detection of PCR products. Primer sequences are as follows: 18S rRNA, 5' primer CGGCTAC-CACATCCAAGGAA (SEQ ID NO. 345) and 3' primer GCTGGAATTACCGCGGCT (SEQ ID NO. 346); Keratin 18, 5' primer GAGCCTGGAGACCGAGAAC (SEQ ID NO. 347) and 3' primer TTGCGAAGATCTGAGCCC (SEQ ID NO. 348); Cyclin D1, 5' primer CACGATTTCATTGAA-CACTTCC (SEQ ID NO. 349) and 3' primer TGAACTTCA-CATCTGTGGCAC (SEQ ID NO. 350). PCR reactions were carried out in 20 µl with 300 nM of each primer (18S reverse primer: only 50 nM). All samples were amplified in duplicate. Expression differences between transfected and wildtype cells for different genes were calculated from PCR amplification curves by relative quantification using the comparative threshold cycle (CT) method. 18S ribosomal RNA was chosen as reference gene for normalisations.

Detection of Fusion Proteins

Fusion proteins were detected by Western blot analysis using the mAb PIN.1 (Stressgen, Biomol, Hamburg, Germany) which binds to amino acid residues 12-28 of Ii. Briefly, cells were lysed as described (Hsieh, C. S., deRoos, P., Honey, K., Beers, C. & Rudensky, A. Y. (2002) J. Immunol. 168, 2618-2625), lysates were boiled in Laemmli loading buffer, separated on a 12% SDS-PAGE and transferred onto nitrocellulose membranes. After a saturation step with BSA, membranes were incubated for 1 h at room temperature with the mAb PIN.1 (1 µg/ml). Proteins were visualised using a peroxidase-coupled sheep anti-mouse IgG (Amersham Pharmacia, Freiburg, Germany). In some cases, transfected cells were cultured in the presence of 10-100 µM chloroquin (Sigma, Steinheim, Germany) in order to investigate the endosomal/lysosomal targeting of the fusion proteins. Cells were then lysed and proteins were detected by Western blot as described above.

Ii-keratin 18 was also detected by immunoprecipitation and subsequent in situ digestion with trypsin followed by mass spectrometric analysis. Briefly, cells were lysed as described (Hsieh, C. S., deRoos, P., Honey, K., Beers, C. & Rudensky, A. Y. (2002) J. Immunol. 168, 2618-2625) and incubated with the mAb PIN.1 and protein A-sepharose beads (Pharmacia, Uppsala, Sweden). Sepharose pellets were washed, boiled in Laemmli loading buffer and run on a 12% SDS-PAGE. Protein spots were excised from the gel and digested in situ with trypsin, essentially as described (Shevchenko, A., Wilm, M., Vorm, O. & Mann, M. (1996) Anal Chem. 68, 850-858). The subsequent analysis was performed on a MALDI-TOF mass spectrometer (Reflex III, Bruker Daltonik, Bremen, Germany). The protein identity was verified by tandem MS spectra recorded on a hybrid quadrupole orthogonal acceleration time-of-flight tandem mass spectrometer (QStar Pulsar i Qqoa Tof; Applied Biosystems-MDS Sciex, Weiterstadt, Germany)

Elution of MHC Class II Bound Peptides

Frozen cell pellets (3.5 to $5 \times 10^{10}$ cells) were processed as previously described (Schirle, M., Keilholz, W., Weber, B., Gouttefangeas, C., Dumrese, T., Becker, H. D., Stevanovic, S. & Rammensee, H. G. (2000) *Eur. J. Immunol.* 30, 2216-2225) and peptides were isolated according to standard protocols (Seeger, F. H., Schirle, M., Keilholz, W., Rammensee, H. G. & Stevanovic, S. (1999) *Immunogenetics* 49, 996-999) using the HLA-DR specific mAb L243 (Lampson, L. A. & Levy, R. (1980) *J. Immunol.* 125, 293-299).

Molecular Analysis of DR-Eluted Peptides

Peptides were separated by reversed-phase high performance liquid chromatography (HPLC, SMART system, μRPC C2/C18 SC 2.1/10; Amersham Pharmacia Biotech, Freiburg, Germany), and fractions were analysed by MALDI-TOF mass spectrometry (MS) using a Bruker Reflex III mass spectrometer (Bruker Daltonik). Differentially presented peptides were further analysed by nano-ESI (electrospray ionisation) tandem MS on a hybrid quadrupole orthogonal acceleration time-of-flight tandem mass spectrometer (Q-TOF; Micromass, Manchester, United Kingdom) as described (Schirle, M., Keilholz, W., Weber, B., Gouttefangeas, C., Dumrese, T., Becker, H. D., Stevanovic, S. & Rammensee, H. G. (2000) *Eur. J. Immunol.* 30, 2216-2225).

Peptide Synthesis and Analysis

Peptides were synthesised in an automated peptide synthesiser EPS221 (Abimed, Langenfeld, Germany) following the Fmoc/tBu strategy. After removal from the resin by treatment with TFA/phenol/ethanedithiol/thioanisole/water (90/3.75/1.25/2.5/2.5 by vol.) for 1 h or 3 h (arginine-containing peptides) peptides were precipitated from methyl-tert. butyl ether, washed once with methyl-tert. butyl ether and twice with diethyl ether and resuspended in water prior to lyophilization. Synthesis products were analysed by HPLC (Varian star, Zinsser analytics, München, Germany) and MALDI-TOF mass spectrometry (future, GSG, Bruchsal, Germany). Peptides of less than 80% purity were purified by preparative HPLC.

Monocyte-Derived Dendritic Cells

Peripheral blood mononuclear cells (PBMC) were prepared according to classical procedures from an HLA-DRB1*0408-, HLA-DRB1*1101-, HLA-DRB3*0202-, HLA-DRB4*01-positive donor. Dendritic cells (DC) were obtained from plastic-adherent PBMC cultured in the presence of GM-CSF and IL-4 for 6 days as described previously (Bender, A., Sapp, M., Schuler, G., Steinman, R. M. & Bhardwaj, N. (1996) *J. Immunol. Methods* 196, 121-135), except that the medium used was X-VIVO 15 (BioWhiftaker) without serum. At day 6, immature DC were analysed by flow cytometry for CD1a, CD11c, CD14, CD40, CD83, CD86 as well as HLA-DR cell surface expression on a FACScalibur apparatus with CELLQuest software (Becton Dickinson, Mountain View, Calif.). DC were then matured in the presence of 50 μg/ml polyinosinic-polycytidylic acid (Poly I/C, Amersham Pharmacia, Uppsala, Sweden) and 10 ng/ml TNF-α (PharMingen) for two additional days and analysed again by flow cytometry for CD14, CD80, CD83 and CD86 cell surface expression. Mature DC showed a clear up-regulation of CD80, CD83 and CD86 molecules.

Generation of Peptide-Specific T-Helper Cells $3 \times 10^5$ matured DC were loaded for two hours with 10 μM of peptide NPPSMVAAGSVVAAV (SEQ ID NO: 1) in a 24-well plate and extensively washed. Then $4 \times 10^6$ fresh autologous PBMC were added onto DC in the presence of 10 ng/ml IL-12p70 in order to favour Th-1 development. PBMC were weekly restimulated with peptide-loaded irradiated autologous PBMC in the presence of 10 U/ml IL-2 and 5 ng/ml IL-7. After 3 and 5 restimulations, T cells were pooled and tested against autologous PBMC in the presence of peptide. The T-helper cell line was then amplified every 1-2 weeks with irradiated allogenic PBMC in the presence of 1 μg/ml PHA, 25-50 U/ml IL-2 and 5 ng/ml IL-7 and then tested for the recognition of the transfected cell lines. Every three to four weeks, the T-helper cell line was restimulated with irradiated autologous PBMC in the presence of 10 μM peptide, 10 U/ml IL-2 and 5 ng/ml IL-7.

Functional Assays and Characterisation of the T-Helper Cell Line

T-helper cell activation was tested by cell proliferation as estimated by thymidine incorporation as well as cytokine secretion. Briefly, $2 \times 10^5$ cells were incubated in triplicates in a 96-well plate with $2 \times 10^5$ irradiated autologous PBMC in the presence or absence of 10 μM peptide or 3 μg/ml PHA. After 24 hours, two portions of 50 μl supernatant were harvested and frozen and 50 μl fresh medium was added to the cells. After 54 hours, 50 μl of tritiated thymidine-containing medium (0.074 MBq/well, Hartmann Analytic, Braunschweig, Germany) was added and thymidine incorporation measured at 72 hours using a scintillation counter (Microbeta, Wallac, Freiburg, Germany). Cell proliferation is expressed as a stimulation index (S.I.), which corresponds to the ratio: (mean cpm of stimulated T cells)/(mean cpm of unstimulated T cells). IL-2 secretion was measured using the IL-2 dependent CTLL-2 cell line. Briefly, $10^4$ cells were incubated in the presence of supernatants for 20-24 hours. Then, thymidine-containing-medium (0.055 MBq/well) was added for 7-8 additional hours and thymidine incorporation was measured as described above. Results are also expressed as a S.I.

IFN-γ, IL-4 and IL-6 secretion was measured by sandwich ELISA using antibody pairs and peroxidase-conjugated streptavidin from PharMingen and according to Manufacturer's recommendations. We used the Supersensitive TMB (Sigma, Deisenhofen, Germany) as a substrate and the reaction was stopped using a 2 M $H_2SO_4$ solution. $OD_{450}$ was then measured and results expressed in pg/ml according to the standards.

Recognition of Cyclin D1-Transfected Cells by the Peptide-Specific T-Helper Cell Line Absence of detectable alloreaction of T cells against the transfectants was demonstrated by co-culturing fresh PBMC from the donor used to generate the T-helper line in the presence of different cell numbers of irradiated transfectants. Cell proliferation as well as IL-2, IL-4, IL-6 and IFN-γ secretion was measured as described above and the Effector/Target ratio to be used in further experiments was thus determined.

Recognition of the naturally processed peptide derived from cyclin D1 was tested by co-culturing the peptide-specific T-helper cell line ($2 \times 10^5$ cells) in the presence of irradiated Awells ($4 \times 10^4$ cells) transfected with a plasmid coding for either cyclin D1 or keratin 18 as a negative control and according to the cell ratio determined above. Irradiated autologous PBMC in the presence of 10 μM peptide or 3 μg/ml PHA served as positive controls. Cell proliferation as well as IL-2 and IFN-γ secretion was measured as described above. In some experiments, cells were cultured in the presence of 20 μg/ml of purified L243 antibody.

Results

Generation of Fusion Protein-Expressing Cell Clones

We cloned the cDNA encoding the 80 N-terminal amino acids of Ii in the vector pcDNA3 in such a way that the 3' end of the insert was followed by a general cloning site (GCS). This gave us a versatile vector to express fusion proteins of Ii and the genes of interest. In frame with Ii we cloned the cDNA of cyclin D1, as well as keratin 18 as a control.

The Awells cell line was stably transfected with vectors encoding the two fusion proteins using electroporation. Subsequently, single-cell-clones were generated and tested on their antigen expression on mRNA and protein level. Compared to the wildtype (untransfected cell line), the best Ii-keratin 18 clone expressed 5,700 times more keratin 18 and the best Ii-cyclin D1 clone expressed 1,200 times more cyclin D1, as determined by real-time quantitative PCR analysis. The data were normalised on 18S ribosomal RNA.

In Western blot analysis, the PIN.1 antibody was used to detect the Ii-fusion proteins. Compared to the wildtype, where only two bands corresponding to two isoforms of Ii (Warmerdam, P. A., Long, E. O. & Roche, P. A. (1996) *J. Cell Biol.* 133, 281-291) were detected, one additional band could be observed in each clone, representing the Ii-keratin 18 or Ii-cyclin D1 fusion proteins with the expected molecular weights (FIG. 1). In the case of the clone Awells-Ii-keratin 18 the fusion protein was also identified via immunoprecipitation followed by an in situ digestion with trypsin and subsequent MS/MS analysis.

The clones were also tested for their HLA class I and class II cell surface expression levels by flow cytometry, in order to determine whether the transfection and cloning procedure interfered with it. Both clones showed normal expression levels of HLA class I and class II molecules, as compared to the untransfected cell line.

Endosomal/Lysosomal Targeting of the Fusion Proteins

Figure 2:
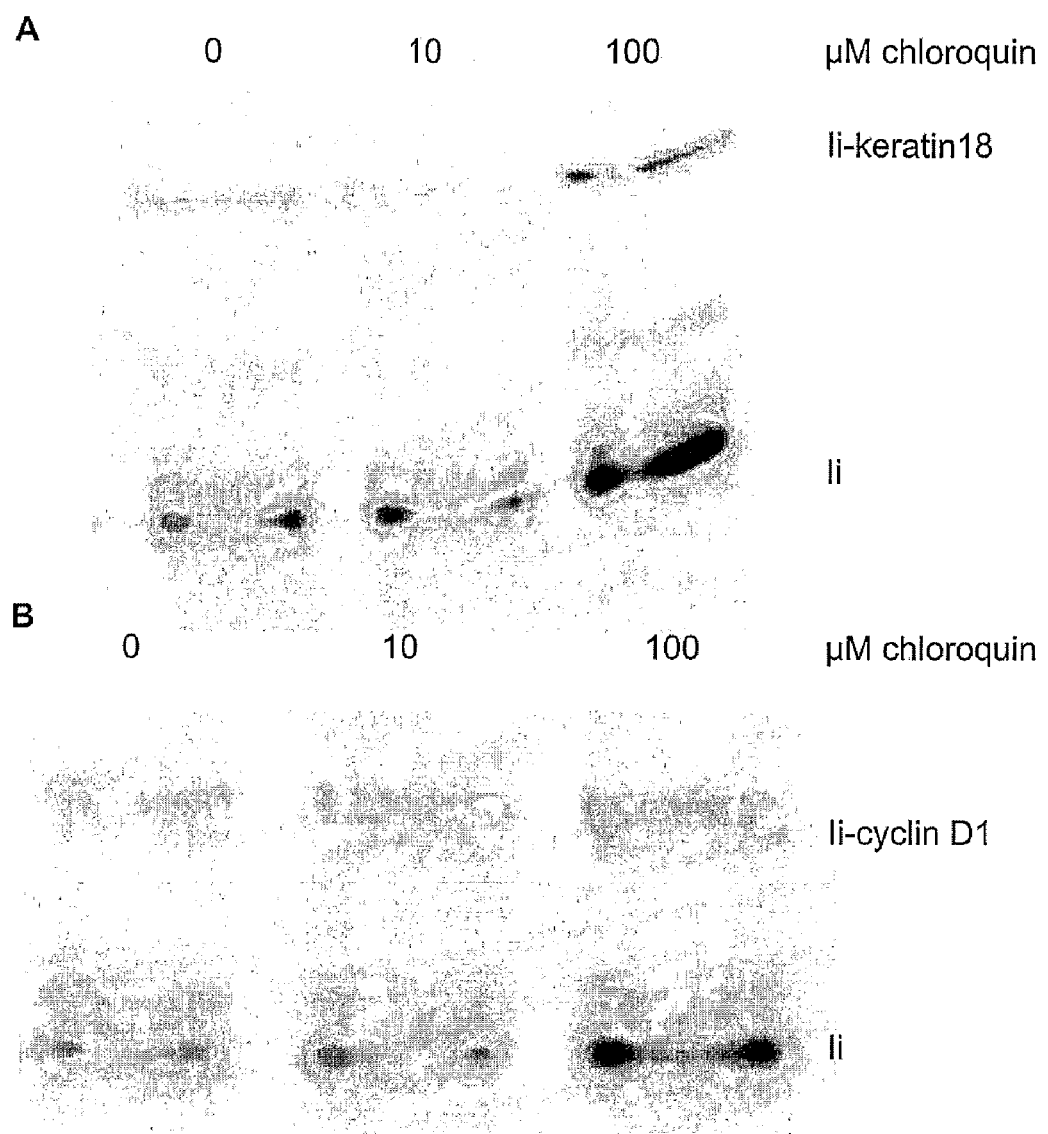
FIG. 2 shows a second Western blot analysis of fusion proteins that have been produced in the course of the experiments.

It has already been described that the N-terminus of Ii is sufficient to target proteins into the MHC class II pathway (Sanderson, S., Frauwirth, K. & Shastri, N. (1995) *Proc. Natl. Acad. Sci. U.S. A* 92, 7217-7221, Wang, R. F., Wang, X., Atwood, A. C., Topalian, S. L. & Rosenberg, S. A. (1999) *Science* 284, 1351-1354, Malcherek, G., Wirblich, C., Willcox, N., Rammensee, H. G., Trowsdale, J. & Melms, A. (1998) *Eur. J. Immunol.* 28, 1524-1533). To test whether our constructs really followed that route of Ag processing, we incubated the transfectants for 4 h with increasing amounts of chloroquin, a cytotoxic drug which inhibits lysosomal degradation of proteins by raising the lysosomal pH (Kaplan, J. & Keogh, E. A. (1981) *Cell* 24, 925-932, Tietze, C., Schlesinger, P. & Stahl, P. (1982) *J. Cell Biol.* 92, 417-424, Seglen, P. O. (1983) *Methods Enzymol.* 96:737-64, 737-764). Cells were then lysed and fusion proteins were detected by Western blot. FIG. 2 shows that the protein bands get more and more intense with increasing amounts of chloroquin, indicating that fusion protein amounts increase with chloroquin concentrations and thus proving that the fusion proteins follow the MHC class II pathway of protein degradation.

Figure 3:
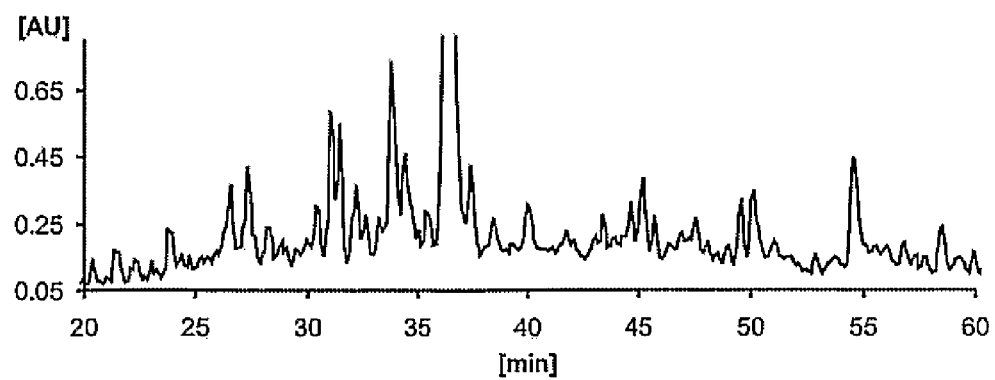
FIG. 3 shows the HPLC-chromatograms of the untransfected cell line and the Awells-Ii-cyclin D1 clone.
Figure 3:
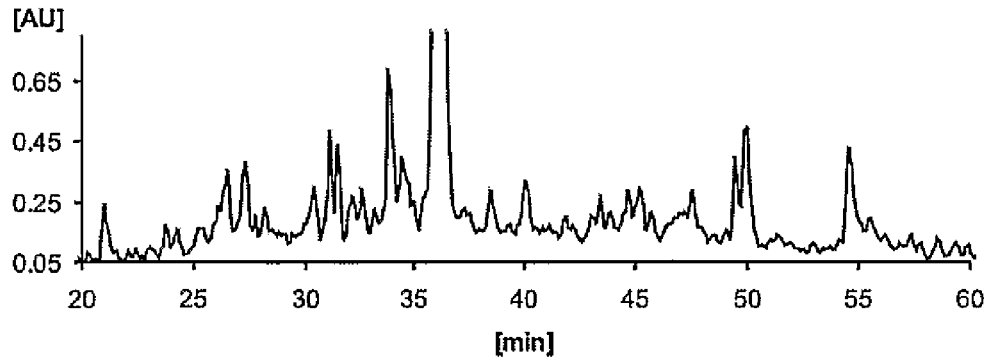
Figure 4:
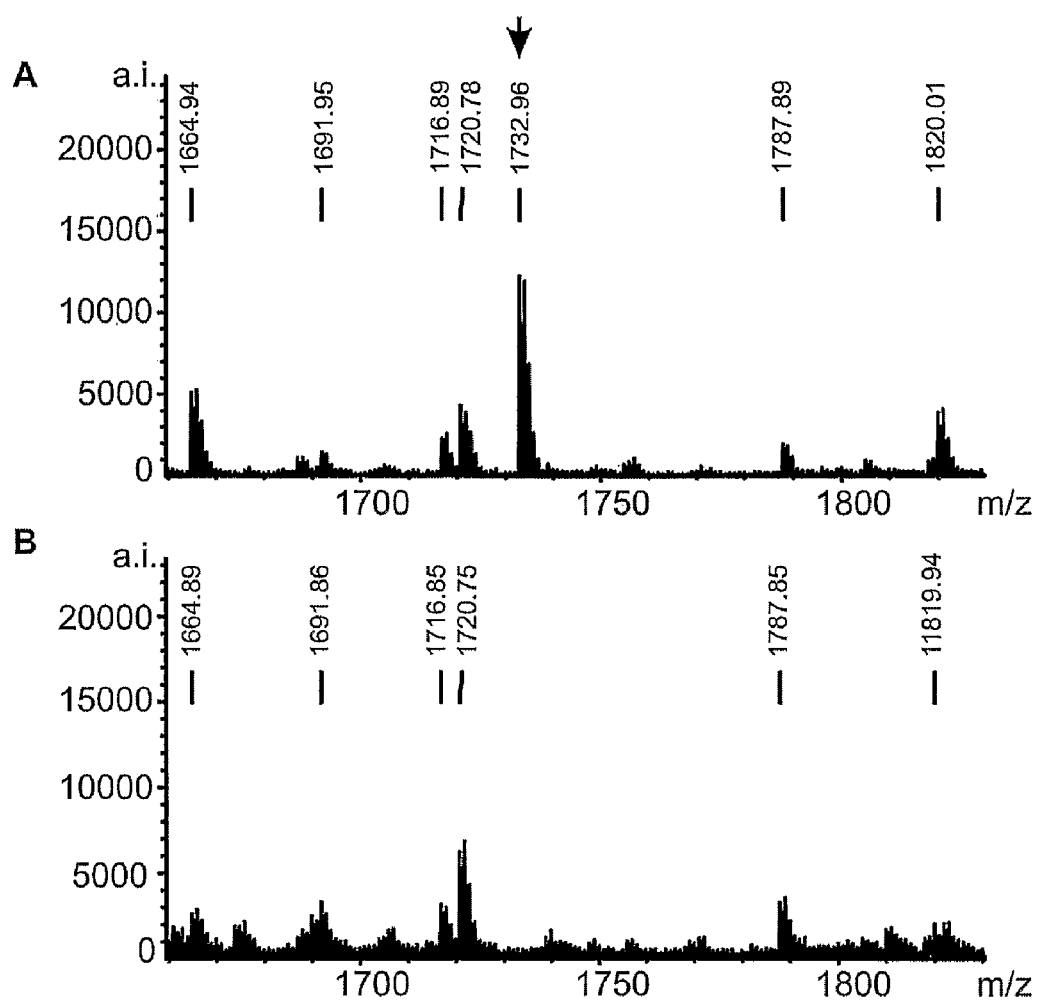
FIGS. 4 and 5 show the mass spectrometric analyses of a preferred fraction having a striking individual signal.
Figure 5:
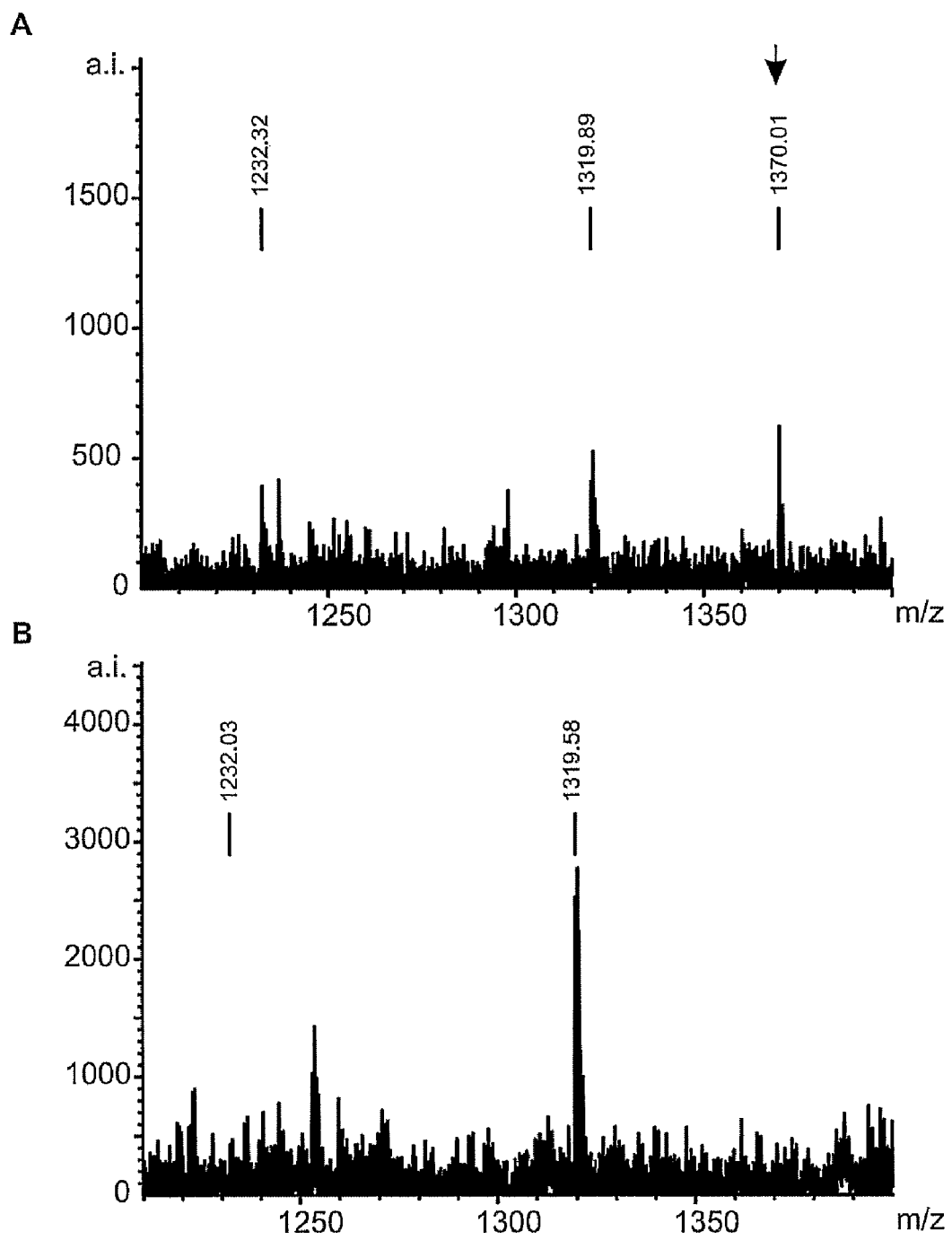
Figure 6:
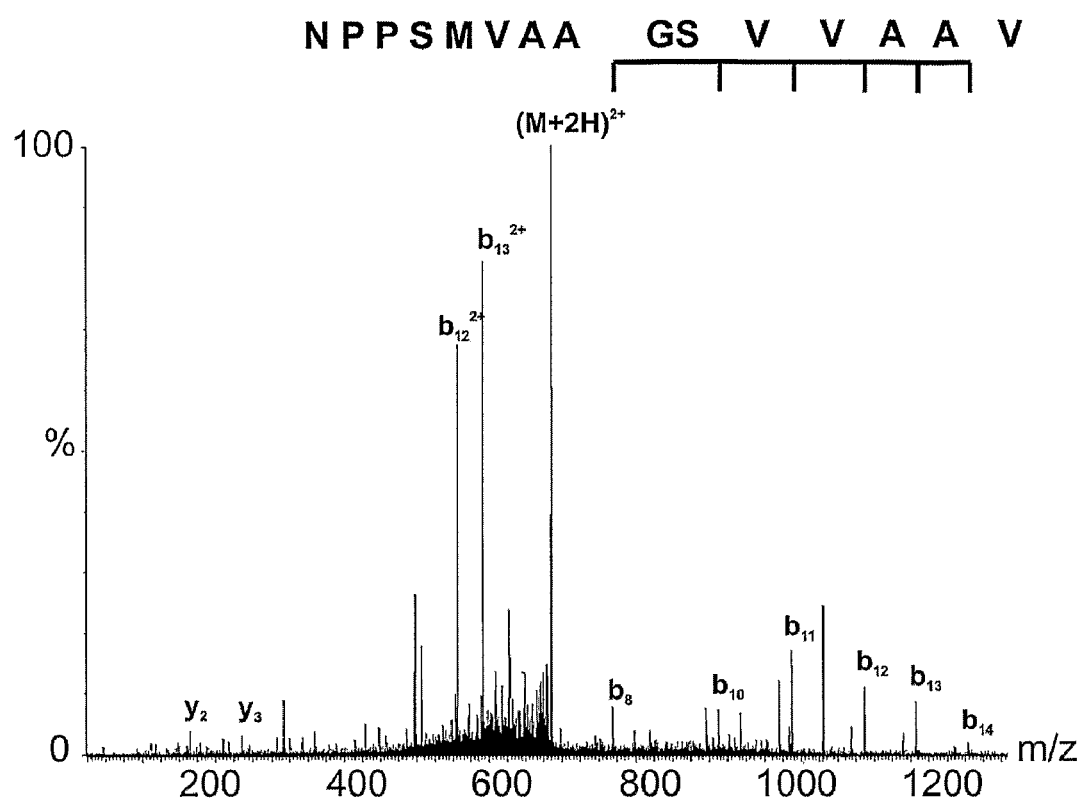
FIG. 6 shows the identification of the peptides NPPSMVAAGSVVAAV (SEQ ID No. 1) (cyclin $D1_{198-212}$).

Differential Mass Spectrometric Analysis of HLA-DR-Bound Peptides 3.5 to $5 \times 10^{10}$ cells from each clone and from the untransfected cell line were grown and the HLA-DR-bound peptides isolated and separated via HPLC as described previously (Seeger, F. H., Schirle, M., Keilholz, W., Rammensee, H. G. & Stevanovic, S. (1999) *Immunogenetics* 49, 996-999). The HPLC-chromatograms of the untransfected cell line and the Awells-Ii-cyclin D1 clone were compared (FIG. 3). Minor, mostly quantitative differences in the HLA-DR-presented peptide repertoire summed up to slightly different UV traces as shown in FIG. 3. As expected from our experience, no distinct UV signals could be assigned to peptides exclusively presented by the transfectants. The only subtle differences in HLA-DR-restricted peptide presentation between Awells and the transfected lines became also visible by MALDI-TOF analysis where most of the HPLC fractions contained identical patterns. FIG. 4 shows the mass spectrometric analysis of the only fraction with a striking individual signal (m/z: 1732.96) which occurred only in the peptide mixture eluted from the keratin 18-transfected line an represented a keratin-18-derived peptide. In FIG. 5, the m/z signal at 1370.1 indicates an exclusively presented peptide from the cyclin D1-transfectant. Both peptides were analysed in greater detail by nanoflow ESI MS/MS (tandem MS). The inventors were able to identify the peptides NPPSMVAAGSVVAAV (SEQ ID No. 1) (cyclin $D1_{198-212}$) (FIG. 6) and SHYFKIIEDLRAQI (SEQ ID No. 2) (keratin $18_{126-139}$) derived from the two transfected fusion proteins, respectively. The sequences were verified by mass spectra of the corresponding synthetic peptides.

Generation and Characterisation of a Peptide-Specific T-Helper Cell Line

Figure 7:
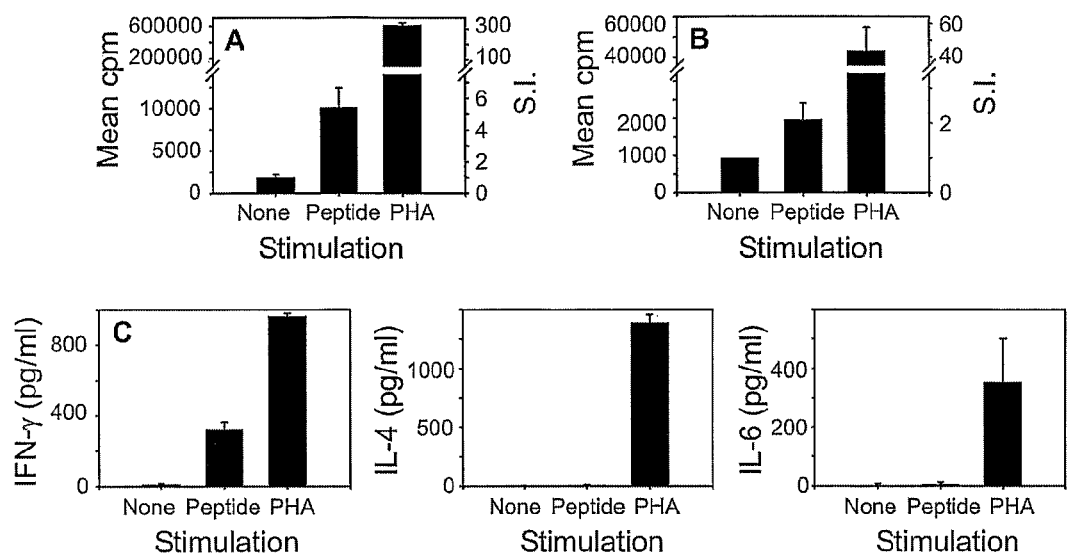
FIG. 7 shows the specific stimulation of T cells by the cyclin D1 peptide, (upper panel) and cytokine production of the T cells in response to the peptide (lower panel).

To establish a proof of concept for the identification of novel, HLA-class II-derived, tumour-associated and putatively immunogenic peptides, T cells specific for the identified cyclin D1 peptide were induced by in vitro stimulation with the corresponding synthetic peptide loaded onto HLA-DR4+ dendritic cells. After the third and the fifth round of in vitro (re-) stimulation, respectively, the specificity of the T-helper cell line was tested. T cells were specifically stimulated by the cyclin D1 peptide, as shown in FIG. 7 (upper panel). T cells proliferated in response to autologous PBMC loaded with the cyclin D1 peptide (S.I.=5.4). As a positive control, PHA induced a strong T-cell proliferation (S.I.=330). The inventors next analysed which type of T-helper cells (Th1 versus Th2) was stimulated in response to the peptide by examining the cytokine profile. As also shown in FIG. 7 (lower panel), the T cells produced IL-2 in response to the peptide, although to a low extent, whereas they were still sensitive to PHA stimulation. On the contrary, peptide-induced T-cell stimulation resulted in a strong IFN-γ secretion (3250 pg/ml, FIG. 7C) but no IL-4 or IL-6 secretion, although T-cells were still highly and moderately sensitive to PHA-induced cytokine secretion, respectively. Stimulation with an unrelated peptide as a negative control for eventual unspecific activation of CD4+ T-helper cells with T-cell receptors specific for HLA-DR4/cyclin $D1_{198-212}$ is presented in FIG. 8. In conclusion, the established CD4+ T-helper cell line is specific for the cyclin $D1_{198-212}$ peptide and is of the Th1 type. This type is particularly important in helping specific CD8+ killer T cells in the elimination of tumour cells.

The Peptide-Specific T-Helper Cell Line Also Recognises Cyclin D1-Transfected Cells Because Awells cells and the T-cell line are not perfectly HLA-matched, we first tested whether any alloreaction could arise by co-culturing both. Briefly, different cell numbers of irradiated Awells-Ii-keratin 18 or Awells-Ii-cyclin D1 transfectants were co-cultured in the presence of a fixed number of PBMC from the T cell donor, and cell proliferation as well as IL-2, IL-4, IL-6 and IFN-γ secretion were measured. A moderate T-cell proliferation was induced by both transfectants at high cell numbers but no cytokine secretion was observed (data not shown). We thus decided to use an (effector T cells)/(target cells) ratio of 5/1, at which only a slight T-cell proliferation was observed in the absence of cytokine secretion. As a consequence, T-cell activation resulting in cytokine secretion could only be induced specifically by the cognate antigen presented by the transfectant.

Figure 8:
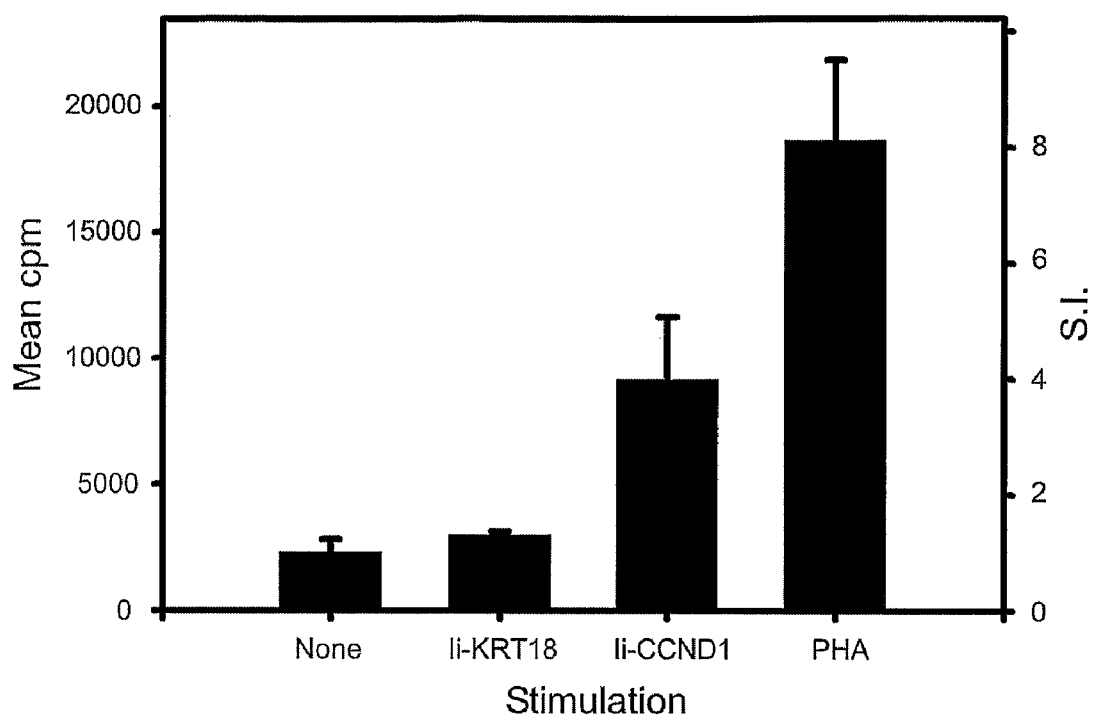
FIG. 8 shows a negative control for eventual unspecific activation of CD4+ T-helper cells with T-cell receptors specific for HLA-DR4/cyclin $D1_{198-212}$.

The T-helper cell line specific for the cyclin D1 peptide was able to recognise the transfected cells over-expressing the cyclin D1 protein and naturally processing and presenting the cyclin D1 peptide in association with HLA-DR molecules. As shown in FIG. 8, irradiated Awells-Ii-cyclin D1 tranfectants were able to specifically activate the T-helper cell line as observed by IL-2 secretion (S.I.=4.0). On the contrary, Awells-Ii-keratin 18 transfectants (used as negative control for T-cell stimulation and known to present the unrelated keratin 18 peptide$_{126-139}$ in association with HLA-DR) did not induce T-cell activation, indicating that the peptide-specific T-helper cell line specifically recognises the cognate antigen. Moreover, these results prove that the cyclin D1 peptide used in the present invention is a naturally processed peptide containing a T-cell epitope. This activation could be inhibited (by 71.2%) by the presence of the HLA-DR-specific blocking L243 Ab.

Production of Activated Cytotoxic Lymphocytes (CTL) Using Class II Molecules and the Peptide Antigen Cyclin D1$_{198-212}$ and their Administration Activated cytotoxic T lymphocytes (CTLs) are produced using HLA-DR Class II molecules and the peptide from cyclin D1$_{198-212}$ (SEQ ID No. 1).

In general, the method described in PCT patent application WO 93/17095 is used to produce the CTLs. Awells cells are used to present the peptide antigen to CTL. The HLA-DR molecule is expressed in the Awells cells. The peptide to be tested is synthesised on an Applied Biosystems synthesiser, ABI 431A (Foster City, Calif., USA) and subsequently purified by HPLC. As is described in detail in WO 93/17095, in order to optimise the in vitro conditions for the generation of specific cytotoxic T cells, the culture of stimulator cells is maintained in an appropriate medium. The stimulator cells are Awells cells, which are preferably maintained in serum-free medium (e.g. Excell 400).

Prior to incubation of the stimulator cells with the cells to be activated, e.g. precursor CD4$^+$ cells, an amount of antigenic peptide is added to the stimulator cell culture, of sufficient quantity to become loaded onto the human Class II molecules to be expressed on the surface of the stimulator cells. A sufficient amount of peptide is an amount that will allow about 200, and preferably 200 or more, human Class II MHC molecules loaded with peptide to be expressed on the surface of each stimulator cell. The stimulator cells are typically incubated with >20 pg/ml peptide.

Resting or precursor CD4+ cells are then incubated in culture with the appropriate stimulator cells for a time period sufficient to activate the CD4+ cells. The CD4+ cells shall thus be activated in an antigen-specific manner. The ratio of resting or precursor CD4+ (effector) cells to stimulator cells may vary from individual to individual and may further depend upon variables such as the amenability of an individual's lymphocytes to culturing conditions. The lymphocyte:stimulator cell (Awells cell) ratio is typically in the range of about 30:1 to 300:1. For example, $3\times10^1$ human PBL and $1\times10^6$ live Awells cells are admixed and maintained in 20 ml of RPMI 1640 culture medium.

The effector/stimulator culture are maintained for as long a time as is necessary to stimulate a therapeutically usable or effective number of CD4+ cells. The optimum time is typically between about one and five days, with a "plateau", i.e. a "maximum" specific CD4+ activation level, generally being observed after five days of culture. In vitro activation of CD4+ cells is typically detected within a brief period of time after transfection of a cell line. Transient expression in a transfected cell line capable of activating CD4+ cells is detectable within 48 hours of transfection. This clearly indicates that either stable or transient cultures of transformed cells expressing human Class II MHC molecules are effective in activating CD4+ cells.

Activated CD4+ cells may be effectively separated from the stimulator (Awells) cells using monoclonal antibodies specific for the stimulator cells, for the peptides loaded onto the stimulator cells, or for the CD4+ cells (or a segment thereof) to bind their appropriate complementary ligand. Antibody-tagged molecules are then extracted from the stimulator effector cell admixture via immunoprecipitation or immunoassay methods.

Effective, cytotoxic amounts of the activated CD4+ cells can vary between in vitro and in vivo uses, as well as with the amount and type of cells that are the ultimate target of these killer cells between about $1\times10^6$ and $1\times10^{12}$ activated CTL are used for adult humans.

The activated CD4+ cells are harvested from the Awells cell culture prior to administration of the CD4+ cells to the individual being treated.

Methods of re-introducing cellular components are used such as those exemplified in U.S. Pat. No. 4,844,893 to Honsik et al and U.S. Pat. No. 4,690,915 to Rosenberg. For example, administration of activated CD8 cells via intravenous infusion is appropriate.

TABLE 1

Tumour-associated T-helper cell peptide epitopes as identified in the present invention

| | Sequence | Position/Gene symbol[i] | Acc. No.[ii] | SEQ ID-No. |
|---|---|---|---|---|
| 1. | NPPSMVAAGSVVAAV | 198-212 CCND1 | P24385 | SEQ ID-No. 1 |
| 2. | SHYFKIIEDLRAQI | 126-139 KRT18 | P05783 | SEQ ID-No. 2 |
| 3. | SGTQFVCETVIRSL | 644-657 M17S2 | Q14596 | SEQ ID-No. 3 |
| 4. | SGTQFVCETVIRSLT | 644-658 M17S2 | Q14596 | SEQ ID-No. 4 |
| 5. | LKPAFKKDGSTTAGN | 260-274 ACAA1 | P09110 | SEQ ID-No. 5 |
| 6. | RDLTDYLMKILTERGYS | 183-199 ACTG1 | P02571 | SEQ ID-No. 6 |
| 7. | TDYLMKILTERGYS | 186-199 ACTG1 | P02571 | SEQ ID-No. 7 |

TABLE 1-continued

Tumour-associated T-helper cell peptide epitopes
as identified in the present invention

| Sequence | Position/Gene symbol[i] | Acc. No.[ii] | SEQ ID-No. |
|---|---|---|---|
| 8. TDYLMKILTERGYSFT | 186-201 ACTG1 | P02571 | SEQ ID-No. 8 |
| 9. WISKQEYDESGPSIVHRKCF | 356-375 ACTG1 | P02571 | SEQ ID-No. 9 |
| 10. YPEEAYIADLDAKSGAS | 247-263 ACLY | P53396 | SEQ ID-No. 10 |
| 11. EGRSFLAFPTLRAYHTL | 1378-1394 AGRN | XP_372195 | SEQ ID-No. 11 |
| 12. GRSFLAFPTLRAYHT | 1379-1393 AGRN | XP_372195 | SEQ ID-No. 12 |
| 13. GRSFLAFPTLRAYHTL | 1379-1394 AGRN | XP_372195 | SEQ ID-No. 13 |
| 14. ISRAQFVPLPVSVSVE | 185-200 AHSG | P12763 | SEQ ID-No. 14 |
| 15. SPDLPKLKPDPNTLCDEF | 133-150 ALB | P02769 | SEQ ID-No. 15 |
| 16. APGKGILAADESTGSIA | 24-40 ALDOA | P04075 | SEQ ID-No. 16 |
| 17. DVPKWISIMTERSVPHLQ | 208-225 ANXA2 | P07355 | SEQ ID-No. 17 |
| 18. VPKWISIMTERSVPH | 209-223 ANXA2 | P07355 | SEQ ID-No. 18 |
| 19. SASYKADTVAKVQG | 1848-1861 APOB | P04114 | SEQ ID-No. 19 |
| 20. IVVYTGDRTVMGRIA | 257-271 ATP1A1 | P05023 | SEQ ID-No. 20 |
| 21. IVVYTGDRTVMGRIAT | 257-272 ATP1A1 | P05023 | SEQ ID-No. 21 |
| 22. FYLLYYTEFTPTEKDEY | 82-98 B2M | P61769 | SEQ ID-No. 22 |
| 23. FYLLYYTEFTPTEKDEYA | 82-99 B2M | P61769 | SEQ ID-No. 23 |
| 24. LLYYTEFTPTEK | 84-95 B2M | P61769 | SEQ ID-No. 24 |
| 25. LLYYTEFTPTEKD | 84-96 B2M | P61769 | SEQ ID-No. 25 |
| 26. LLYYTEFTPTEKDE | 84-97 B2M | P61769 | SEQ ID-No. 26 |
| 27. LLYYTEFTPTEKDEYA | 84-99 B2M | P61769 | SEQ ID-No. 27 |
| 28. YLLYYTEFTPTEK | 83-95 B2M | P61769 | SEQ ID-No. 28 |
| 29. YLLYYTEFTPTEKDE | 83-97 B2M | P61769 | SEQ ID-No. 29 |
| 30. YLLYYTEFTPTEKDEY | 83-98 B2M | P61769 | SEQ ID-No. 30 |
| 31. YLLYYTEFTPTEKDEYA | 83-99 B2M | P61769 | SEQ ID-No. 31 |

TABLE 1-continued

Tumour-associated T-helper cell peptide epitopes
as identified in the present invention

| | Sequence | Position/Gene symbol[i] | Acc. No.[ii] | SEQ ID-No. |
|---|---|---|---|---|
| 32. | YTEFTPTEKDEY | 87-98 B2M | P61769 | SEQ ID-No. 32 |
| 33. | YYTEFTPTEKDEY | 86-98 B2M | P61769 | SEQ ID-No. 33 |
| 34. | TGKTPGAEIDFKYALIGTAVGVA | 74-96 C10orf128 | XP_378226 | SEQ ID-No. 34 |
| 35. | TEEFEVTKTAVAHRPG | 138-153 C19orf10 | NP_061980 | SEQ ID-No. 35 |
| 36. | RGYMEIEQSVKSFK | 173-186 C5orf15 | NP_064584 | SEQ ID-No. 36 |
| 37. | IPWFVSDTTIHDFN | 285-298 C6orf211 | NP_078849 | SEQ ID-No. 37 |
| 38. | IAYDVTYSLACVR | 306-318 CCR7 | P32248 | SEQ ID-No. 38 |
| 39. | NIAYDVTYSLACVR | 305-318 CCR7 | P32248 | SEQ ID-No. 39 |
| 40. | SLMVTNDGATILKN | 60-73 CCT2 | P78371 | SEQ ID-No. 40 |
| 41. | ATQYFADRDMFCAGRVP | 299-315 CCT7 | Q99832 | SEQ ID-No. 41 |
| 42. | VATQYFADRDMFCAGRVP | 298-315 CCT7 | Q99832 | SEQ ID-No. 42 |
| 43. | GPKPLFRRMSSLVGP | 26-40 MS4A1 | P11836 | SEQ ID-No. 43 |
| 44. | GPKPLFRRMSSLVGPT | 26-41 MS4A1 | P11836 | SEQ ID-No. 44 |
| 45. | GPKPLFRRMSSLVGPTQS | 26-43 MS4A1 | P11836 | SEQ ID-No. 45 |
| 46. | SGPKPLFRRMSSLVGPTQS | 25-43 MS4A1 | P11836 | SEQ ID-No. 46 |
| 47. | SGPKPLFRRMSSLVGPTQSF | 25-44 MS4A1 | P11836 | SEQ ID-No. 47 |
| 48. | RDMFTLEDTL | 140-149 CD38 | P28907 | SEQ ID-No. 48 |
| 49. | RDMFTLEDTLLG | 140-151 CD38 | P28907 | SEQ ID-No. 49 |
| 50. | RDMFTLEDTLLGYLAD | 140-155 CD38 | P28907 | SEQ ID-No. 50 |
| 51. | VQRDMFTLEDTL | 138-149 CD38 | P28907 | SEQ ID-No. 51 |
| 52. | SPGEPQIIFCRSEAAHQG | 389-406 PTPRC | P08575 | SEQ ID-No. 52 |
| 53. | SPGEPQIIFCRSEAAHQGVI | 389-408 PTPRC | P08575 | SEQ ID-No. 53 |
| 54. | ATPLLMQALPMGALPQGP | 110-127 CD74 | P04233 | SEQ ID-No. 54 |
| 55. | GHLKIMHDAIGFR | 160-172 CLN5 | O75503 | SEQ ID-No. 55 |

TABLE 1-continued

Tumour-associated T-helper cell peptide epitopes
as identified in the present invention

| | Sequence | Position/Gene symbol[i] | Acc. No.[ii] | SEQ ID-No. |
|---|---|---|---|---|
| 56. | LGHLKIMHDAIGFR | 159-172 CLN5 | O75503 | SEQ ID-No. 56 |
| 57. | NPPLFALDKDAPLRY | 47-61 CLSTN3 | Q9BQT9 | SEQ ID-No. 57 |
| 58. | LEKIVLDNSVFSEHRN | 1008-1023 CLTCL1 | P53675 | SEQ ID-No. 58 |
| 59. | GQRRFNLQKNFVGKVA | 177-192 COCH | O43405 | SEQ ID-No. 59 |
| 60. | IGQRRFNLQKNFVGKVAL | 176-193 COCH | O43405 | SEQ ID-No. 60 |
| 61. | RRFNLQKNFVGKVA | 179-192 COCH | O43405 | SEQ ID-No. 61 |
| 62. | VPGTYKITASARGYN | 836-850 CPD | O75976 | SEQ ID-No. 62 |
| 63. | LAKWVAIQSVSAWPE | 22-36 CNDP2 | Q96KP4 | SEQ ID-No. 63 |
| 64. | VARFAAAATQQQTA | 404-417 CPNE3 | O75131 | SEQ ID-No. 64 |
| 65. | WGALATISTLEAVR | 68-81 CREG | NP_003842 | SEQ ID-No. 65 |
| 66. | VGVPYRITVTAVSASG | 385-400 IL27RA | NP_004834 | SEQ ID-No. 66 |
| 67. | VPYRITVTAVSASG | 387-400 IL27RA | NP_004834 | SEQ ID-No. 67 |
| 68. | DHNFVKAINAIQKSW | 171-185 CTSC | P53634 | SEQ ID-No. 68 |
| 69. | KKVVVYLQKLDTAYDDLG | 62-79 CTSC | P53634 | SEQ ID-No. 69 |
| 70. | KYDHNFVKAINAIQKSWT | 169-186 CTSC | P53634 | SEQ ID-No. 70 |
| 71. | SGMDYWIVKNSWGTGWG | 418-434 CTSC | P53634 | SEQ ID-No. 71 |
| 72. | YDHNFVKAINAIQK | 170-183 CTSC | P53634 | SEQ ID-No. 72 |
| 73. | YDHNFVKAINAIQKSWT | 170-186 CTSC | P53634 | SEQ ID-No. 73 |
| 74. | IFSFYLSRDPDAQPG | 228-242 CTSD | P07339 | SEQ ID-No. 74 |
| 75. | LSRDPDAQPGGE | 233-244 CTSD | P07339 | SEQ ID-No. 75 |
| 76. | GKEYWLVKNSWGHN | 290-303 CTSS | P25774 | SEQ ID-No. 76 |
| 77. | KNLKFVMLHNLEHSM | 54-68 CTSS | P25774 | SEQ ID-No. 77 |
| 78. | TTAFQYIIDNKGID | 186-199 CTSS | P25774 | SEQ ID-No. 78 |
| 79. | GTEYWIVRNSWGEPW | 253-267 CTSZ | Q9UBR2 | SEQ ID-No. 79 |

TABLE 1-continued

Tumour-associated T-helper cell peptide epitopes
as identified in the present invention

| Sequence | Position/ Gene symbol[i] | Acc. No.[ii] | SEQ ID-No. |
| --- | --- | --- | --- |
| 80. GYLPNQLFRTF | 730-740 DDX1 | Q92499 | SEQ ID-No. 80 |
| 81. IRFVVDSGKVKEM | 367-379 DHX34 | Q14147 | SEQ ID-No. 81 |
| 82. MEKYNIEKDIAAYIK | 29-43 Dlc2 | NP_542408 | SEQ ID-No. 82 |
| 83. LPFGAQSTQRGHTE | 114-127 DPP7 | Q9UHL4 | SEQ ID-No. 83 |
| 84. SKYYVTIIDAPGHRD | 83-97 EEF1A1 | P04720 | SEQ ID-No. 84 |
| 85. IEKFEKEAAEMGKG | 39-52 EEF1A2 | Q05639 | SEQ ID-No. 85 |
| 86. IEKFEKEAAEMGKGS | 39-53 EEF1A2 | Q05639 | SEQ ID-No. 86 |
| 87. IEKFEKEAAEMGKGSF | 39-54 EEF1A2 | Q05639 | SEQ ID-No. 87 |
| 88. TIEKFEKEAAEMGKGSF | 38-54 EEF1A2 | Q05639 | SEQ ID-No. 88 |
| 89. DIDAIFKDLSIRSVR | 57-71 WBSCR1 | Q15056 | SEQ ID-No. 89 |
| 90. GVPLYRHIADLAGN | 126-139 ENO1 | P06733 | SEQ ID-No. 90 |
| 91. GVPLYRHIADLAGNSEV | 126-142 ENO1 | P06733 | SEQ ID-No. 91 |
| 92. IKEKYGKDATNVGDEG | 195-210 ENO1 | P06733 | SEQ ID-No. 92 |
| 93. IKEKYGKDATNVGDEGG | 195-211 ENO1 | P06733 | SEQ ID-No. 93 |
| 94. KEKYGKDATNVGDEGG | 196-211 ENO1 | P06733 | SEQ ID-No. 94 |
| 95. VIKEKYGKDATNVGDEGG | 194-211 ENO1 | P06733 | SEQ ID-No. 95 |
| 96. VPLYRHIADLAGN | 127-139 ENO1 | P06733 | SEQ ID-No. 96 |
| 97. VPLYRHIADLAGNSE | 127-141 ENO1 | P06733 | SEQ ID-No. 97 |
| 98. VPLYRHIADLAGNSEV | 127-142 ENO1 | P06733 | SEQ ID-No. 98 |
| 99. VPLYRHIADLAGNSEVI | 127-143 ENO1 | P06733 | SEQ ID-No. 99 |
| 100. LLQKLILWRVL | 305-315 FLJ32752 | NP_653267 | SEQ ID-No. 100 |
| 101. LQNIIPASTGAAKAVG | 202-217 GAPD | P04406 | SEQ ID-No. 101 |
| 102. EPIEQKFVSISDLLVPK | 374-390 GDI2 | P50395 | SEQ ID-No. 102 |
| 103. AIFLFVDKTVPQSS | 75-88 GABARAPL2 | P60520 | SEQ ID-No. 103 |

TABLE 1-continued

Tumour-associated T-helper cell peptide epitopes
as identified in the present invention

| Sequence | Position/Gene symbol[i] | Acc. No.[ii] | SEQ ID-No. |
|---|---|---|---|
| 104. AIFLFVDKTVPQSSL | 75-89 GABARAPL2 | P60520 | SEQ ID-No. 104 |
| 105. AIFLFVDKTVPQSSLT | 75-90 GABARAPL2 | P60520 | SEQ ID-No. 105 |
| 106. FVDKTVPQSSL | 79-89 GABARAPL2 | P60520 | SEQ ID-No. 106 |
| 107. LPSEKAIFLFVDKTVPQSSLT | 70-90 GABARAPL2 | P60520 | SEQ ID-No. 107 |
| 108. KVNLLKIKTELCKKEV | 1035-1050 GLG1 | Q92896 | SEQ ID-No. 108 |
| 109. LGKWCSEKTETGQE | 643-656 GLG1 | Q92896 | SEQ ID-No. 109 |
| 110. VNLLKIKTELCKKEV | 1036-1050 GLG1 | Q92896 | SEQ ID-No. 110 |
| 111. GNYRIESVLSSSG | 166-178 GM2A | P17900 | SEQ ID-No. 111 |
| 112. GNYRIESVLSSSGK | 166-179 GM2A | P17900 | SEQ ID-No. 112 |
| 113. LGCIKIAASLKGI | 181-193 GM2A | P17900 | SEQ ID-No. 113 |
| 114. RLGCIKIAASLKGI | 180-193 GM2A | P17900 | SEQ ID-No. 114 |
| 115. TGNYRIESVLSSSG | 165-178 GM2A | P17900 | SEQ ID-No. 115 |
| 116. TGNYRIESVLSSSGK | 165-179 GM2A | P17900 | SEQ ID-No. 116 |
| 117. TGNYRIESVLSSSGKR | 165-180 GM2A | P17900 | SEQ ID-No. 117 |
| 118. TTGNYRIESVLSSSG | 164-178 GM2A | P17900 | SEQ ID-No. 118 |
| 119. TTGNYRIESVLSSSGK | 164-179 GM2A | P17900 | SEQ ID-No. 119 |
| 120. VTRAFVAARTFAQGL | 211-225 GPC4 | O75487 | SEQ ID-No. 120 |
| 121. DIFERIASEASRL | 68-80 HIST1H2BL | Q99880 | SEQ ID-No. 121 |
| 122. DIFERIASEASRLA | 68-81 HIST1H2BL | Q99880 | SEQ ID-No. 122 |
| 123. DIFERIASEASRLAH | 68-82 HIST1H2BL | Q99880 | SEQ ID-No. 123 |
| 124. DIFERIASEASRLAHY | 68-83 HIST1H2BL | Q99880 | SEQ ID-No. 124 |
| 125. VNDIFERIASEASRLAHYN | 66-84 HIST1H2BL | Q99880 | SEQ ID-No. 125 |
| 126. DDTQFVRFDSDAASQR | 53-68 HLA-A | CAA73716 | SEQ ID-No. 126 |
| 127. DDTQFVRFDSDAASQRME | 53-70 HLA-A | CAA73716 | SEQ ID-No. 127 |

TABLE 1-continued

Tumour-associated T-helper cell peptide epitopes
as identified in the present invention

| Sequence | Position/Gene symbol[i] | Acc. No.[ii] | SEQ ID-No. |
|---|---|---|---|
| 128. DDTQFVRFDSDAASQRMEP | 53-71 HLA-A | CAA73716 | SEQ ID-No. 128 |
| 129. DDTQFVRFDSDAASQRMEPR | 53-72 HLA-A | CAA73716 | SEQ ID-No. 129 |
| 130. DTEFVRFDSDAASQRME | 54-70 HLA-A | CAA73716 | SEQ ID-No. 130 |
| 131. DTEFVRFDSDAASQRMEP | 54-71 HLA-A | CAA73716 | SEQ ID-No. 131 |
| 132. DTQFVRFDSDAASQ | 54-67 HLA-A | CAA73716 | SEQ ID-No. 132 |
| 133. DTQFVRFDSDAASQR | 54-68 HLA-A | CAA73716 | SEQ ID-No. 133 |
| 134. DTQFVRFDSDAASQRM | 54-69 HLA-A | CAA73716 | SEQ ID-No. 134 |
| 135. DTQFVRFDSDAASQRME | 54-70 HLA-A | CAA73716 | SEQ ID-No. 135 |
| 136. DTQFVRFDSDAASQRMEP | 54-71 HLA-A | CAA73716 | SEQ ID-No. 136 |
| 137. DTQFVRFDSDAASQRMEPRAP | 54-74 HLA-A | CAA73716 | SEQ ID-No. 137 |
| 138. FVRFDSDAASQR | 57-68 HLA-A | CAA73716 | SEQ ID-No. 138 |
| 139. FVRFDSDAASQRME | 57-70 HLA-A | CAA73716 | SEQ ID-No. 139 |
| 140. KHKWEAAHVAEQLR | 168-181 HLA-A | CAA73716 | SEQ ID-No. 140 |
| 141. QFVRFDSDAASQRME | 56-70 HLA-A | CAA73716 | SEQ ID-No. 141 |
| 142. TQFVRFDSDAASQ | 55-67 HLA-A | CAA73716 | SEQ ID-No. 142 |
| 143. TQFVRFDSDAASQR | 55-68 HLA-A | CAA73716 | SEQ ID-No. 143 |
| 144. TTKHKWEAAHVAEQLR | 166-181 HLA-A | CAA73716 | SEQ ID-No. 144 |
| 145. VDDTEFVRFDSDAASQR | 52-68 HLA-A | CAA73716 | SEQ ID-No. 145 |
| 146. VDDTQFVRFDSDAASQRMEPRAPW | 52-75 HLA-A | CAA73716 | SEQ ID-No. 146 |
| 147. VDDTQFVRFDSDAASQRMEPRAPWIE | 52-77 HLA-A | CAA73716 | SEQ ID-No. 147 |
| 148. DLSSWTAADTAAQIT | 153-167 HLA-B | P30481 | SEQ ID-No. 148 |
| 149. DLSSWTAADTAAQITQ | 153-168 HLA-B | P30481 | SEQ ID-No. 149 |
| 150. DLSSWTAADTAAQITQRKW | 153-171 HLA-B | P30481 | SEQ ID-No. 150 |
| 151. DLSSWTAADTAAQITQRKWEAARVA | 153-177 HLA-B | P30481 | SEQ ID-No. 151 |

TABLE 1-continued

Tumour-associated T-helper cell peptide epitopes
as identified in the present invention

| Sequence | Position/Gene symbol[i] | Acc. No.[ii] | SEQ ID-No. |
|---|---|---|---|
| 152. DTLFVRFDSDATSPRKEPRAP | 54-74 HLA-B | P30481 | SEQ ID-No. 152 |
| 153. EDLSSWTAADTAAQIT | 152-167 HLA-B | P30481 | SEQ ID-No. 153 |
| 154. EDLSSWTAADTAAQITQR | 152-169 HLA-B | P30481 | SEQ ID-No. 154 |
| 155. EDLSSWTAADTAAQITQRKW | 152-171 HLA-B | P30481 | SEQ ID-No. 155 |
| 156. EDLSSWTAADTAAQITQRKWE | 152-172 HLA-B | P30481 | SEQ ID-No. 156 |
| 157. EDLSSWTAADTAAQITQRKWEAARVA | 152-177 HLA-B | P30481 | SEQ ID-No. 157 |
| 158. GPEYWDRETQISKTN | 80-94 HLA-B | P30481 | SEQ ID-No. 158 |
| 159. KDYIALNEDLSSWTA | 145-159 HLA-B | P30481 | SEQ ID-No. 159 |
| 160. LNEDLSSWTAADTAAQITQRKWE | 150-172 HLA-B | P30481 | SEQ ID-No. 160 |
| 161. LRWEPSSQSTVPIVGIVAG | 296-314 HLA-B | P30481 | SEQ ID-No. 161 |
| 162. LSSWTAADTAAEITERKWE | 154-172 HLA-B | P30481 | SEQ ID-No. 162 |
| 163. LSSWTAADTAAQITQR | 154-169 HLA-B | P30481 | SEQ ID-No. 163 |
| 164. LSSWTAADTAAQITQRKW | 154-171 HLA-B | P30481 | SEQ ID-No. 164 |
| 165. LSSWTAADTAAQITQRKWE | 154-172 HLA-B | P30481 | SEQ ID-No. 165 |
| 166. NEDLSSWTAADTAAQITQRKW | 151-171 HLA-B | P30481 | SEQ ID-No. 166 |
| 167. TLFVRFDSDATSP | 55-67 HLA-B | P30481 | SEQ ID-No. 167 |
| 168. VDDTLFVRFDSDATSPRKEPRAP | 52-74 HLA-B | P30481 | SEQ ID-No. 168 |
| 169. DDTQFVQFDSDAASPR | 53-68 HLA-C | Q9TNN7 | SEQ ID-No. 169 |
| 170. DGKDYIALNEDLRSWT | 143-158 HLA-C | Q9TNN7 | SEQ ID-No. 170 |
| 171. DGKDYIALNEDLRSWTA | 143-159 HLA-C | Q9TNN7 | SEQ ID-No. 171 |
| 172. DGKDYIALNEDLRSWTAA | 143-160 HLA-C | Q9TNN7 | SEQ ID-No. 172 |
| 173. DTQFVQFDSDAASPR | 54-68 HLA-C | Q9TNN7 | SEQ ID-No. 173 |
| 174. DTQFVQFDSDAASPRG | 54-69 HLA-C | Q9TNN7 | SEQ ID-No. 174 |
| 175. DTQFVQFDSDAASPRGEPR | 54-72 HLA-C | Q9TNN7 | SEQ ID-No. 175 |

TABLE 1-continued

Tumour-associated T-helper cell peptide epitopes
as identified in the present invention

| Sequence | Position/ Gene symbol[i] | Acc. No.[ii] | SEQ ID-No. |
|---|---|---|---|
| 176. DTQFVQFDSDAASPRGEPRAP | 54-74 HLA-C | Q9TNN7 | SEQ ID-No. 176 |
| 177. DYIALNEDLRSWTA | 146-159 HLA-C | Q9TNN7 | SEQ ID-No. 177 |
| 178. FVQFDSDAASPRGEP | 57-71 HLA-C | Q9TNN7 | SEQ ID-No. 178 |
| 179. GKDYIALNEDLRSWT | 144-158 HLA-C | Q9TNN7 | SEQ ID-No. 179 |
| 180. GRLLRGYNQFAYDGK | 131-145 HLA-C | Q9TNN7 | SEQ ID-No. 180 |
| 181. KDYIALNEDLRSW | 145-157 HLA-C | Q9TNN7 | SEQ ID-No. 181 |
| 182. TQFVQFDSDAASPR | 55-68 HLA-C | Q9TNN7 | SEQ ID-No. 182 |
| 183. TQFVQFDSDAASPRGEPR | 55-72 HLA-C | Q9TNN7 | SEQ ID-No. 183 |
| 184. VDDTQFVQFDSDAASPRGEPR | 52-72 HLA-C | Q9TNN7 | SEQ ID-No. 184 |
| 185. VDDTQFVQFDSDAASPRGEPRAP | 52-74 HLA-C | Q9TNN7 | SEQ ID-No. 185 |
| 186. YVDDTQFVQFDSDAASPRGEPRAP | 51-74 HLA-C | Q9TNN7 | SEQ ID-No. 186 |
| 187. FGPTFVSAVDGLSFQ | 167-181 HLA-DMA | CAA54170 | SEQ ID-No. 187 |
| 188. NREEFVRFDSDVGEFR | 24-39 HLA-DPB1 | AAA36255 | SEQ ID-No. 188 |
| 189. REEFVRFDSDVGEFR | 25-39 HLA-DPB1 | AAA36255 | SEQ ID-No. 189 |
| 190. DVEVYRAVTPLGPPD | 35-49 HLA-DQB1 | CAA71450 | SEQ ID-No. 190 |
| 191. AQGALANIAVDKANLEI | 81-97 HLA-DRA | P01903 | SEQ ID-No. 191 |
| 192. IQAEFYLNPDQSGEF | 33-47 HLA-DRA | P01903 | SEQ ID-No. 192 |
| 193. GAGLFIYFRNQKGHS | 243-257 HLA-DRB1 | P13760 | SEQ ID-No. 193 |
| 194. HQEEYVRFDSDVGEYR | 62-77 HLA-DRB1 | P13760 | SEQ ID-No. 194 |
| 195. HQEEYVRFDSDVGEYRA | 62-78 HLA-DRB1 | P13760 | SEQ ID-No. 195 |
| 196. HQEEYVRFDSDVGEYRAV | 62-79 HLA-DRB1 | P13760 | SEQ ID-No. 196 |
| 197. QEEYVRFDSDVGEYR | 63-77 HLA-DRB1 | P13760 | SEQ ID-No. 197 |
| 198. YVRFDSDVGEY | 66-76 HLA-DRB1 | P13760 | SEQ ID-No. 198 |
| 199. DLRSWTAVDTAAQISEQ | 150-166 HLA-E | P13747 | SEQ ID-No. 199 |

TABLE 1-continued

Tumour-associated T-helper cell peptide epitopes
as identified in the present invention

| Sequence | Position/Gene symbol[i] | Acc. No.[ii] | SEQ ID-No. |
|---|---|---|---|
| 200. LRSWTAVDTAAQIS | 151-164 HLA-E | P13747 | SEQ ID-No. 200 |
| 201. LRSWTAVDTAAQISEQ | 151-166 HLA-E | P13747 | SEQ ID-No. 201 |
| 202. VDDTQFVRFDSDSACPRMEP | 52-71 HLA-G | P17693 | SEQ ID-No. 202 |
| 203. YVDDTQFVRFDSDSACPRMEPRAP | 51-74 HLA-G | P17693 | SEQ ID-No. 203 |
| 204. AIPFVIEKAVRSSIY | 146-160 HPCL2 | Q9UJ83 | SEQ ID-No. 204 |
| 205. AIPFVIEKAVRSSIYG | 146-161 HPCL2 | Q9UJ83 | SEQ ID-No. 205 |
| 206. NVLRIINEPTAAAIAY | 168-183 HSPA1B | P08107 | SEQ ID-No. 206 |
| 207. RIINEPTAAAIA | 171-182 HSPA1B | P08107 | SEQ ID-No. 207 |
| 208. RIINEPTAAAIAYG | 171-184 HSPA1B | P08107 | SEQ ID-No. 208 |
| 209. VLRIINEPTAAAIA | 169-182 HSPA1B | P08107 | SEQ ID-No. 209 |
| 210. VLRIINEPTAAAIAY | 169-183 HSPA1B | P08107 | SEQ ID-No. 210 |
| 211. VLRIINEPTAAAIAYG | 169-184 HSPA1B | P08107 | SEQ ID-No. 211 |
| 212. VMRIINEPTAAAIAYG | 195-210 HSPA5 | P11021 | SEQ ID-No. 212 |
| 213. VPTKKSQIFSTASDNQPTVT | 443-462 HSPA5 | P11021 | SEQ ID-No. 213 |
| 214. GERAMTKDNNLLGRFE | 447-462 HSPA6 | P17066 | SEQ ID-No. 214 |
| 215. ERAMTKDNNLLGKFEL | 446-461 HSPA8 | P11142 | SEQ ID-No. 215 |
| 216. GERAMTKDNNLLGKFE | 445-460 HSPA8 | P11142 | SEQ ID-No. 216 |
| 217. GERAMTKDNNLLGKFEL | 445-461 HSPA8 | P11142 | SEQ ID-No. 217 |
| 218. GILNVSAVDKSTGKE | 484-498 HSPA8 | P11142 | SEQ ID-No. 218 |
| 219. RAMTKDNNLLGKFE | 447-460 HSPA8 | P11142 | SEQ ID-No. 219 |
| 220. IPIIIHPIDRSVD | 109-121 MTP18 | NP_057582 | SEQ ID-No. 220 |
| 221. DRKMVGDVTGAQAY | 65-78 IFITM1 | P13164 | SEQ ID-No. 221 |
| 222. DRKMVGDVTGAQAYA | 65-79 IFITM1 | P13164 | SEQ ID-No. 222 |
| 223. LGFIAFAYSVKSRD | 52-65 IFITM1 | P13164 | SEQ ID-No. 223 |

TABLE 1-continued

Tumour-associated T-helper cell peptide epitopes as identified in the present invention

| Sequence | Position/Gene symbol[i] | Acc. No.[ii] | SEQ ID-No. |
|---|---|---|---|
| 224. LITFLCDRDAGVGFP | 726-740 IGF2R | P11717 | SEQ ID-No. 224 |
| 225. LITFLCDRDAGVGFPE | 726-741 IGF2R | P11717 | SEQ ID-No. 225 |
| 226. KNTLYLQMNSLKTEDTA | 29-45 IGH@ | AAM87802 | SEQ ID-No. 226 |
| 227. NTLYLQMNSLKTEDT | 30-44 IGH@ | AAM87802 | SEQ ID-No. 227 |
| 228. NTLYLQMNSLKTEDTA | 30-45 IGH@ | AAM87802 | SEQ ID-No. 228 |
| 229. TLYLQMNSLKTED | 31-43 IGH@ | AAM87802 | SEQ ID-No. 229 |
| 230. TLYLQMNSLKTEDT | 31-44 IGH@ | AAM87802 | SEQ ID-No. 230 |
| 231. TLYLQMNSLKTEDTA | 31-45 IGH@ | AAM87802 | SEQ ID-No. 231 |
| 232. YLQMNSLKTEDT | 33-43 IGH@ | AAM87802 | SEQ ID-No. 232 |
| 233. ESGPTTYKVTSTLTIKESDWL | 171-191 IGHM | P01871 | SEQ ID-No. 233 |
| 234. GPTTYKVTSTLTIK | 173-186 IGHM | P01871 | SEQ ID-No. 234 |
| 235. GPTTYKVTSTLTIKE | 173-187 IGHM | P01871 | SEQ ID-No. 235 |
| 236. SGPTTYKVTSTLTIK | 172-186 IGHM | P01871 | SEQ ID-No. 236 |
| 237. SGPTTYKVTSTLTIKESDWL | 172-191 IGHM | P01871 | SEQ ID-No. 237 |
| 238. EPRRYGSAAALPS | 68-80 IGHMBP2 | P38935 | SEQ ID-No. 238 |
| 239. HKSYSCQVTHEGSTV | 81-95 IGLC1 | P01842 | SEQ ID-No. 239 |
| 240. HKSYSCQVTHEGSTVE | 81-96 IGLC1 | P01842 | SEQ ID-No. 240 |
| 241. KSHKSYSCQVTHEGSTVE | 79-96 IGLC1 | P01842 | SEQ ID-No. 241 |
| 242. KSYSCQVTHEGST | 82-94 IGLC1 | P01842 | SEQ ID-No. 242 |
| 243. KSYSCQVTHEGSTV | 82-95 IGLC1 | P01842 | SEQ ID-No. 243 |
| 244. KSYSCQVTHEGSTVE | 82-96 IGLC1 | P01842 | SEQ ID-No. 244 |
| 245. KSYSCQVTHEGSTVEK | 82-97 IGLC1 | P01842 | SEQ ID-No. 245 |
| 246. SHKSYSCQVTHEGST | 80-94 IGLC1 | P01842 | SEQ ID-No. 246 |
| 247. SHKSYSCQVTHEGSTV | 80-95 IGLC1 | P01842 | SEQ ID-No. 247 |

TABLE 1-continued

Tumour-associated T-helper cell peptide epitopes
as identified in the present invention

| Sequence | Position/Gene symbol[i] | Acc. No.[ii] | SEQ ID-No. |
|---|---|---|---|
| 248. SHKSYSCQVTHEGSTVE | 80-96 IGLC1 | P01842 | SEQ ID-No. 248 |
| 249. SHKSYSCQVTHEGSTVEKT | 80-98 IGLC1 | P01842 | SEQ ID-No. 249 |
| 250. TPEQWKSHKSYSCQVTHEGSTVE | 74-96 IGLC1 | P01842 | SEQ ID-No. 250 |
| 251. IEVWVAENALGKVT | 194-208 IL6ST | P40189 | SEQ ID-No. 251 |
| 252. YPSHSFIGEESVAAGEK | 62-78 IMPA1 | P29218 | SEQ ID-No. 252 |
| 253. DTGSYRAQISTKTSAK | 103-118 SLAMF6 | CAC59749 | SEQ ID-No. 253 |
| 254. FSQFLGDPVEKAAQ | 411-424 KIAA0494 | O75071 | SEQ ID-No. 254 |
| 255. LPSYEEALSLPSKTP | 236-250 LAPTM5 | Q13571 | SEQ ID-No. 255 |
| 256. LPSYEEALSLPSKTPE | 236-251 LAPTM5 | Q13571 | SEQ ID-No. 256 |
| 257. LPSYEEALSLPSKTPEG | 236-252 LAPTM5 | Q13571 | SEQ ID-No. 257 |
| 258. VVLPSYEEALSLPSKTPE | 234-251 LAPTM5 | Q13571 | SEQ ID-No. 258 |
| 259. GVPKDYTGEDVTPQN | 98-112 LGMN | Q99538 | SEQ ID-No. 259 |
| 260. VPKDYTGEDVTPQN | 99-112 LGMN | Q99538 | SEQ ID-No. 260 |
| 261. DVRKLYWLMKSSLNGDN | 902-918 LNPEP | Q9UIQ6 | SEQ ID-No. 261 |
| 262. KPTICSDQDNYCVT | 37-50 LY6E | Q16553 | SEQ ID-No. 262 |
| 263. LKPTICSDQDNYCVT | 36-50 LY6E | Q16553 | SEQ ID-No. 263 |
| 264. HPPELLFSASLPALG | 559-573 MAN2B1 | O00754 | SEQ ID-No. 264 |
| 265. VDYFLNVATAQGRYY | 292-306 MAN2B1 | O00754 | SEQ ID-No. 265 |
| 266. TPISEVYESEKDEDGFL | 92-108 MAP1LC3B | Q9GZQ8 | SEQ ID-No. 266 |
| 267. TPISEVYESEKDEDGFLY | 92-109 MAP1LC3B | Q9GZQ8 | SEQ ID-No. 267 |
| 268. SPDRVYINYYDMNAAN | 90-105 MIF | P14174 | SEQ ID-No. 268 |
| 269. VPDGFLSELTQQLAQ | 14-28 MIF | P14174 | SEQ ID-No. 269 |
| 270. DGRTFYIDHNSKITQ | 541-555 NEDD4L | NP_056092 | SEQ ID-No. 270 |
| 271. GPVGVFEWEAFARGT | 337-351 PGK1 | P00558 | SEQ ID-No. 271 |

TABLE 1-continued

Tumour-associated T-helper cell peptide epitopes
as identified in the present invention

| Sequence | Position/Gene symbol[i] | Acc. No.[ii] | SEQ ID-No. |
|---|---|---|---|
| 272. RVVMRVDFNVPMKN | 17-30 PGK1 | P00558 | SEQ ID-No. 272 |
| 273. SPDDKYIYVADILAHEIH | 228-245 PON2 | Q15165 | SEQ ID-No. 273 |
| 274. LPGLAKQPSFRQYSG | 38-52 PPGB | P10619 | SEQ ID-No. 274 |
| 275. VSFELFADKVPKTAEN | 19-34 PPIA | P05092 | SEQ ID-No. 275 |
| 276. GPSYWCQNTETAAQ | 498-511 PSAP | P07602 | SEQ ID-No. 276 |
| 277. VPGFADDPTELACRV | 417-431 PTGFRN | Q9P2B2 | SEQ ID-No. 277 |
| 278. GALLVYDITSRETYN | 83-97 RAB4A | P20338 | SEQ ID-No. 278 |
| 279. LIPSYIRDSTVAVVV | 78-92 RAB6B | Q9NRW1 | SEQ ID-No. 279 |
| 280. FPEPIKLDKNDRAKASA | 186-202 RAB7 | P51149 | SEQ ID-No. 280 |
| 281. AFFTLARDIKAKMD | 161-174 RAB8A | P61006 | SEQ ID-No. 281 |
| 282. NAFFTLARDIKAKMD | 160-174 RAB8A | P61006 | SEQ ID-No. 282 |
| 283. LLQQISQHQEHF | 313-324 RAD23B | P54727 | SEQ ID-No. 283 |
| 284. TEQFTAMRDLYMKN | 61-74 RAP1A | P10113 | SEQ ID-No. 284 |
| 285. IPSVFIGESSANSLKD | 145-160 RNF13 | O43567 | SEQ ID-No. 285 |
| 286. ADRDTYRRSAVPPGAD | 122-137 RPS10 | P46783 | SEQ ID-No. 286 |
| 287. DRDTYRRSAVPPGAD | 123-137 RPS10 | P46783 | SEQ ID-No. 287 |
| 288. RDTYRRSAVPPGAD | 124-137 RPS10 | P46783 | SEQ ID-No. 288 |
| 289. LPPNWKYESSTASA | 134-147 RPS13 | P62277 | SEQ ID-No. 289 |
| 290. RTFHRAASSAAQGAF | 308-326 SCAMP2 | O15127 | SEQ ID-No. 290 |
| 291. SRTFHRAASSAAQGA | 309-325 SCAMP2 | O15127 | SEQ ID-No. 291 |
| 292. SSRTFHRAASSAAQGA | 310-325 SCAMP2 | O15127 | SEQ ID-No. 292 |
| 293. SSRTFHRAASSAAQGAF | 310-326 SCAMP2 | O15127 | SEQ ID-No. 293 |
| 294. YGSYSTQASAAAAT | 83-96 SCAMP3 | O14828 | SEQ ID-No. 294 |
| 295. YGSYSTQASAAAATA | 83-97 SCAMP3 | O14828 | SEQ ID-No. 295 |

TABLE 1-continued

Tumour-associated T-helper cell peptide epitopes
as identified in the present invention

| Sequence | Position/Gene symbol[i] | Acc. No.[ii] | SEQ ID-No. |
|---|---|---|---|
| 296. YGSYSTQASAAAATAE | 83-98 SCAMP3 | O14828 | SEQ ID-No. 296 |
| 297. VPMYIGEISPTALR | 162-175 SLC2A14 | NP_703150 | SEQ ID-No. 297 |
| 298. ISIYSSERSVLQ | 519-530 SEMA7A | O75326 | SEQ ID-No. 298 |
| 299. VAAVFIAQLSQQSLDFVK | 396-413 SLC1A5 | Q15758 | SEQ ID-No. 299 |
| 300. TGALYRIGDLQAFQGHG | 120-136 SLC3A2 | P08195 | SEQ ID-No. 300 |
| 301. DYYKGEESNSSANK | 150-163 NAPB | Q9H115 | SEQ ID-No. 301 |
| 302. KPGIYRSNMDGSAAY | 899-913 SORL1 | Q92673 | SEQ ID-No. 302 |
| 303. RHPINEYYIADASEDQVF | 343-360 SORL1 | Q92673 | SEQ ID-No. 303 |
| 304. NPRKFNLDATELSIR | 74-88 STX6 | O43752 | SEQ ID-No. 304 |
| 305. NPRKFNLDATELSIRK | 74-89 STX6 | O43752 | SEQ ID-No. 305 |
| 306. NPRKFNLDATELSIRKA | 74-90 STX6 | O43752 | SEQ ID-No. 306 |
| 307. GPPIGSFTLIDSEVSQL | 88-104 unnamed protein product | BAD18470 | SEQ ID-No. 307 |
| 308. NPKDVLVGADSVRAAITF | 134-151 SYNGR2 | O43760 | SEQ ID-No. 308 |
| 309. HKGEIRGASTPFQFR | 107-121 TAX1BP1 | NP_006015 | SEQ ID-No. 309 |
| 310. DVAFVKDQTVIQ | 555-566 TF | Q29443 | SEQ ID-No. 310 |
| 311. FVKDQTVIQNTD | 558-569 TF | Q29443 | SEQ ID-No. 311 |
| 312. GDVAFVKDQTVIQ | 554-566 TF | Q29443 | SEQ ID-No. 312 |
| 313. GDVAFVKDQTVIQNTD | 554-569 TF | Q29443 | SEQ ID-No. 313 |
| 314. CPSDWKTDSTCRMVT | 353-367 TFRC | P02786 | SEQ ID-No. 314 |
| 315. CPSDWKTDSTCRMVTS | 353-368 TFRC | P02786 | SEQ ID-No. 315 |
| 316. CPSDWKTDSTCRMVTSE | 353-369 TFRC | P02786 | SEQ ID-No. 316 |
| 317. FTYINLDKAVLGTSN | 479-493 TFRC | P02786 | SEQ ID-No. 317 |
| 318. YVAYSKAATVTGKL | 219-232 TFRC | P02786 | SEQ ID-No. 318 |

TABLE 1-continued

Tumour-associated T-helper cell peptide epitopes as identified in the present invention

| Sequence | Position/ Gene symbol[i] | Acc. No.[ii] | SEQ ID-No. |
|---|---|---|---|
| 319. EIIHKALIDRNIQ | 62-74 TNFAIP3 | P21580 | SEQ ID-No. 319 |
| 320. GPLSWYSDPGLAGVS | 105-119 TNFSF9 | P41273 | SEQ ID-No. 320 |
| 321. LKPEFVDIINAKQ | 236-248 TPI1 | P60174 | SEQ ID-No. 321 |
| 322. GSSYGSETSIPAAAH | 811-825 TTYH3 | XP_166523 | SEQ ID-No. 322 |
| 323. AKFWEVISDEHGIDPT | 18-33 TUBB1 | P07437 | SEQ ID-No. 323 |
| 324. EPYNATLSVHQL | 181-192 TUBB5 | P05218 | SEQ ID-No. 324 |
| 325. EPYNATLSVHQLVE | 181-194 TUBB5 | P05218 | SEQ ID-No. 325 |
| 326. DYNIQKESTLHLVLR | 58-72 UBA52 | P02248 | SEQ ID-No. 326 |
| 327. SDYNIQKESTLHLV | 57-70 UBA52 | P02248 | SEQ ID-No. 327 |
| 328. DKGAFRIEINFPAEYPFKPP | 47-66 UBE2L3 | P51966 | SEQ ID-No. 328 |
| 329. KGAFRIEINFPAEYPFKPP | 48-66 UBE2L3 | P51966 | SEQ ID-No. 329 |
| 330. NPPYDKGAFRIEINFPAEYPFKPP | 43-66 UBE2L3 | P51966 | SEQ ID-No. 330 |
| 331. PPYDKGAFRIEINFPAEYPFKPP | 44-66 UBE2L3 | P51966 | SEQ ID-No. 331 |
| 332. NPDTLSAMSNPRAMQ | 447-461 UBQLN1 | Q9UMX0 | SEQ ID-No. 332 |
| 333. QLIYIPLPDEKSRVA | 640-654 VCP | P55072 | SEQ ID-No. 333 |
| 334. AAKYQLDPTASISA | 248-261 VDAC2 | P45880 | SEQ ID-No. 334 |
| 335. DPDPEDFADEQSLVGRFI | 478-495 VPS35 | Q96QK1 | SEQ ID-No. 335 |
| 336. APSGFYIASGDVSGKL | 67-82 WDR1 | O75083 | SEQ ID-No. 336 |
| 337. APSGFYIASGDVSGKLR | 67-83 WDR1 | O75083 | SEQ ID-No. 337 |
| 338. RASWRIISSIEQKEE | 57-71 YWHAE | NP_006752 | SEQ ID-No. 338 |

[i]According to HUGO gene nomenclature
[ii]Accession Number according to Entrez Protein Database (NCBI)

The invention claimed is:

1. An isolated tumour associated peptide comprising SEQ ID NO: 273 wherein said peptide exhibits an overall length of 100 or fewer amino acids.

2. The tumour associated peptide according to claim 1, wherein said peptide exhibits an overall length of not more than 30 amino acids.

3. The tumour associated peptide according to claim 1, consisting of SEQ ID NO: 273.

4. The tumour associated peptide according to claim 1, having the ability to bind to a molecule of the human major histocompatibility complex (MHC) class-II.

5. The tumour associated peptide according to claim 4, wherein when bound to HLA-DR the peptide-bound is capable of eliciting the production of a cytotoxic T lymphocyte (CTL) which recognizes a cell which aberrantly expresses a polypeptide comprising the given amino acid sequence.

6. The tumour associated peptide according to claim 1, wherein the peptide includes non-peptide bonds.

7. The tumor associated peptide of claim 1, wherein said peptide comprises an N-terminal extension of 1 to 10 amino acids in length.

8. The tumor associated peptide of claim 1, wherein said peptide comprises a C-terminal extension of 1 to 10 amino acids in length.

9. The tumor associated peptide of claim 1, wherein said peptide consists of:
   a) SEQ ID NO: 273; and
   b) an N-terminal extension of 1 to 10 amino acids in length; and
   c) a C-terminal extension of 1 to 10 amino acids in length.

10. The tumor associated peptide of claim 1, wherein said peptide consists of:
   a) SEQ ID NO: 273; and
   b) an N-terminal extension of 1 to 10 amino acids in length;
   c) a C-terminal extension of 1 to 10 amino acids in length; and
   d) N-terminal amino acids of the HLA-DR antigen-associated invariant chain (Ii).

11. A fusion protein comprising N-terminal amino acids of the HLA-DR antigen-associated invariant chain (Ii) and SEQ ID NO: 273.

12. An isolated nucleic acid, encoding a tumour associated peptide according to claim 1.

13. The nucleic acid according to claim 12 which is DNA, cDNA, PNA, CNA, RNA or combinations thereof.

14. An expression vector capable of expressing a nucleic acid encoding a tumour associated peptide according to claim 1.

15. An isolated host cell comprising a nucleic acid encoding a tumour associated peptide according to claim 1.

16. The host cell according to claim 15 that is a recombinant Awells cell.

17. A pharmaceutical composition comprising
a) a tumour associated peptide according to claim 1; or
b) a nucleic acid, encoding the tumour associated peptide;
and a pharmaceutically acceptable carrier.

* * * * *

SEQUENCE LISTING

<160> NUMBER OF SEQ ID NOS: 338

<210> SEQ ID NO 1
<211> LENGTH: 15
<212> TYPE: PRT
<213> ORGANISM: Homo sapiens

<400> SEQUENCE: 1

Asn Pro Pro Ser Met Val Ala Ala Gly Ser Val Val Ala Ala Val
1               5                   10                  15

<210> SEQ ID NO 2
<211> LENGTH: 14
<212> TYPE: PRT
<213> ORGANISM: Homo sapiens

<400> SEQUENCE: 2

Ser His Tyr Phe Lys Ile Ile Glu Asp Leu Arg Ala Gln Ile
1               5                   10

<210> SEQ ID NO 3
<211> LENGTH: 14
<212> TYPE: PRT
<213> ORGANISM: Homo sapiens

<400> SEQUENCE: 3

Ser Gly Thr Gln Phe Val Cys Glu Thr Val Ile Arg Ser Leu
1               5                   10

<210> SEQ ID NO 4
<211> LENGTH: 15
<212> TYPE: PRT
<213> ORGANISM: Homo sapiens

<400> SEQUENCE: 4

Ser Gly Thr Gln Phe Val Cys Glu Thr Val Ile Arg Ser Leu Thr
1               5                   10                  15

<210> SEQ ID NO 5
<211> LENGTH: 15
<212> TYPE: PRT
<213> ORGANISM: Homo sapiens

<400> SEQUENCE: 5

Leu Lys Pro Ala Phe Lys Lys Asp Gly Ser Thr Thr Ala Gly Asn
1               5                   10                  15

<210> SEQ ID NO 6
<211> LENGTH: 17
<212> TYPE: PRT
<213> ORGANISM: Homo sapiens

<400> SEQUENCE: 6

Arg Asp Leu Thr Asp Tyr Leu Met Lys Ile Leu Thr Glu Arg Gly Tyr
1               5                   10                  15

Ser

<210> SEQ ID NO 7
<211> LENGTH: 14
<212> TYPE: PRT
<213> ORGANISM: Homo sapiens

```
<400> SEQUENCE: 7

Thr Asp Tyr Leu Met Lys Ile Leu Thr Glu Arg Gly Tyr Ser
1               5                   10

<210> SEQ ID NO 8
<211> LENGTH: 16
<212> TYPE: PRT
<213> ORGANISM: Homo sapiens

<400> SEQUENCE: 8

Thr Asp Tyr Leu Met Lys Ile Leu Thr Glu Arg Gly Tyr Ser Phe Thr
1               5                   10                  15

<210> SEQ ID NO 9
<211> LENGTH: 20
<212> TYPE: PRT
<213> ORGANISM: Homo sapiens

<400> SEQUENCE: 9

Trp Ile Ser Lys Gln Glu Tyr Asp Glu Ser Gly Pro Ser Ile Val His
1               5                   10                  15

Arg Lys Cys Phe
            20

<210> SEQ ID NO 10
<211> LENGTH: 17
<212> TYPE: PRT
<213> ORGANISM: Homo sapiens

<400> SEQUENCE: 10

Tyr Pro Glu Glu Ala Tyr Ile Ala Asp Leu Asp Ala Lys Ser Gly Ala
1               5                   10                  15

Ser

<210> SEQ ID NO 11
<211> LENGTH: 17
<212> TYPE: PRT
<213> ORGANISM: Homo sapiens

<400> SEQUENCE: 11

Glu Gly Arg Ser Phe Leu Ala Phe Pro Thr Leu Arg Ala Tyr His Thr
1               5                   10                  15

Leu

<210> SEQ ID NO 12
<211> LENGTH: 15
<212> TYPE: PRT
<213> ORGANISM: Homo sapiens

<400> SEQUENCE: 12

Gly Arg Ser Phe Leu Ala Phe Pro Thr Leu Arg Ala Tyr His Thr
1               5                   10                  15

<210> SEQ ID NO 13
<211> LENGTH: 16
<212> TYPE: PRT
<213> ORGANISM: Homo sapiens

<400> SEQUENCE: 13

Gly Arg Ser Phe Leu Ala Phe Pro Thr Leu Arg Ala Tyr His Thr Leu
1               5                   10                  15
```

<210> SEQ ID NO 14
<211> LENGTH: 16
<212> TYPE: PRT
<213> ORGANISM: Homo sapiens

<400> SEQUENCE: 14

Ile Ser Arg Ala Gln Phe Val Pro Leu Pro Val Ser Val Ser Val Glu
1               5                   10                  15

<210> SEQ ID NO 15
<211> LENGTH: 18
<212> TYPE: PRT
<213> ORGANISM: Homo sapiens

<400> SEQUENCE: 15

Ser Pro Asp Leu Pro Lys Leu Lys Pro Asp Pro Asn Thr Leu Cys Asp
1               5                   10                  15

Glu Phe

<210> SEQ ID NO 16
<211> LENGTH: 17
<212> TYPE: PRT
<213> ORGANISM: Homo sapiens

<400> SEQUENCE: 16

Ala Pro Gly Lys Gly Ile Leu Ala Ala Asp Glu Ser Thr Gly Ser Ile
1               5                   10                  15

Ala

<210> SEQ ID NO 17
<211> LENGTH: 18
<212> TYPE: PRT
<213> ORGANISM: Homo sapiens

<400> SEQUENCE: 17

Asp Val Pro Lys Trp Ile Ser Ile Met Thr Glu Arg Ser Val Pro His
1               5                   10                  15

Leu Gln

<210> SEQ ID NO 18
<211> LENGTH: 15
<212> TYPE: PRT
<213> ORGANISM: Homo sapiens

<400> SEQUENCE: 18

Val Pro Lys Trp Ile Ser Ile Met Thr Glu Arg Ser Val Pro His
1               5                   10                  15

<210> SEQ ID NO 19
<211> LENGTH: 14
<212> TYPE: PRT
<213> ORGANISM: Homo sapiens

<400> SEQUENCE: 19

Ser Ala Ser Tyr Lys Ala Asp Thr Val Ala Lys Val Gln Gly
1               5                   10

<210> SEQ ID NO 20
<211> LENGTH: 15
<212> TYPE: PRT
<213> ORGANISM: Homo sapiens

<400> SEQUENCE: 20

```
Ile Val Val Tyr Thr Gly Asp Arg Thr Val Met Gly Arg Ile Ala
1               5                   10                  15

<210> SEQ ID NO 21
<211> LENGTH: 16
<212> TYPE: PRT
<213> ORGANISM: Homo sapiens

<400> SEQUENCE: 21

Ile Val Val Tyr Thr Gly Asp Arg Thr Val Met Gly Arg Ile Ala Thr
1               5                   10                  15

<210> SEQ ID NO 22
<211> LENGTH: 17
<212> TYPE: PRT
<213> ORGANISM: Homo sapiens

<400> SEQUENCE: 22

Phe Tyr Leu Leu Tyr Tyr Thr Glu Phe Thr Pro Thr Glu Lys Asp Glu
1               5                   10                  15

Tyr

<210> SEQ ID NO 23
<211> LENGTH: 18
<212> TYPE: PRT
<213> ORGANISM: Homo sapiens

<400> SEQUENCE: 23

Phe Tyr Leu Leu Tyr Tyr Thr Glu Phe Thr Pro Thr Glu Lys Asp Glu
1               5                   10                  15

Tyr Ala

<210> SEQ ID NO 24
<211> LENGTH: 12
<212> TYPE: PRT
<213> ORGANISM: Homo sapiens

<400> SEQUENCE: 24

Leu Leu Tyr Tyr Thr Glu Phe Thr Pro Thr Glu Lys
1               5                   10

<210> SEQ ID NO 25
<211> LENGTH: 13
<212> TYPE: PRT
<213> ORGANISM: Homo sapiens

<400> SEQUENCE: 25

Leu Leu Tyr Tyr Thr Glu Phe Thr Pro Thr Glu Lys Asp
1               5                   10

<210> SEQ ID NO 26
<211> LENGTH: 14
<212> TYPE: PRT
<213> ORGANISM: Homo sapiens

<400> SEQUENCE: 26

Leu Leu Tyr Tyr Thr Glu Phe Thr Pro Thr Glu Lys Asp Glu
1               5                   10

<210> SEQ ID NO 27
<211> LENGTH: 16
<212> TYPE: PRT
<213> ORGANISM: Homo sapiens
```

<400> SEQUENCE: 27

Leu Leu Tyr Tyr Thr Glu Phe Thr Pro Thr Glu Lys Asp Glu Tyr Ala
1               5                   10                  15

<210> SEQ ID NO 28
<211> LENGTH: 13
<212> TYPE: PRT
<213> ORGANISM: Homo sapiens

<400> SEQUENCE: 28

Tyr Leu Leu Tyr Tyr Thr Glu Phe Thr Pro Thr Glu Lys
1               5                   10

<210> SEQ ID NO 29
<211> LENGTH: 15
<212> TYPE: PRT
<213> ORGANISM: Homo sapiens

<400> SEQUENCE: 29

Tyr Leu Leu Tyr Tyr Thr Glu Phe Thr Pro Thr Glu Lys Asp Glu
1               5                   10                  15

<210> SEQ ID NO 30
<211> LENGTH: 16
<212> TYPE: PRT
<213> ORGANISM: Homo sapiens

<400> SEQUENCE: 30

Tyr Leu Leu Tyr Tyr Thr Glu Phe Thr Pro Thr Glu Lys Asp Glu Tyr
1               5                   10                  15

<210> SEQ ID NO 31
<211> LENGTH: 17
<212> TYPE: PRT
<213> ORGANISM: Homo sapiens

<400> SEQUENCE: 31

Tyr Leu Leu Tyr Tyr Thr Glu Phe Thr Pro Thr Glu Lys Asp Glu Tyr
1               5                   10                  15

Ala

<210> SEQ ID NO 32
<211> LENGTH: 12
<212> TYPE: PRT
<213> ORGANISM: Homo sapiens

<400> SEQUENCE: 32

Tyr Thr Glu Phe Thr Pro Thr Glu Lys Asp Glu Tyr
1               5                   10

<210> SEQ ID NO 33
<211> LENGTH: 13
<212> TYPE: PRT
<213> ORGANISM: Homo sapiens

<400> SEQUENCE: 33

Tyr Tyr Thr Glu Phe Thr Pro Thr Glu Lys Asp Glu Tyr
1               5                   10

<210> SEQ ID NO 34
<211> LENGTH: 23
<212> TYPE: PRT
<213> ORGANISM: Homo sapiens

```
<400> SEQUENCE: 34

Thr Gly Lys Thr Pro Gly Ala Glu Ile Asp Phe Lys Tyr Ala Leu Ile
1               5                   10                  15

Gly Thr Ala Val Gly Val Ala
            20

<210> SEQ ID NO 35
<211> LENGTH: 16
<212> TYPE: PRT
<213> ORGANISM: Homo sapiens

<400> SEQUENCE: 35

Thr Glu Glu Phe Glu Val Thr Lys Thr Ala Val Ala His Arg Pro Gly
1               5                   10                  15

<210> SEQ ID NO 36
<211> LENGTH: 14
<212> TYPE: PRT
<213> ORGANISM: Homo sapiens

<400> SEQUENCE: 36

Arg Gly Tyr Met Glu Ile Glu Gln Ser Val Lys Ser Phe Lys
1               5                   10

<210> SEQ ID NO 37
<211> LENGTH: 14
<212> TYPE: PRT
<213> ORGANISM: Homo sapiens

<400> SEQUENCE: 37

Ile Pro Trp Phe Val Ser Asp Thr Thr Ile His Asp Phe Asn
1               5                   10

<210> SEQ ID NO 38
<211> LENGTH: 13
<212> TYPE: PRT
<213> ORGANISM: Homo sapiens

<400> SEQUENCE: 38

Ile Ala Tyr Asp Val Thr Tyr Ser Leu Ala Cys Val Arg
1               5                   10

<210> SEQ ID NO 39
<211> LENGTH: 14
<212> TYPE: PRT
<213> ORGANISM: Homo sapiens

<400> SEQUENCE: 39

Asn Ile Ala Tyr Asp Val Thr Tyr Ser Leu Ala Cys Val Arg
1               5                   10

<210> SEQ ID NO 40
<211> LENGTH: 14
<212> TYPE: PRT
<213> ORGANISM: Homo sapiens

<400> SEQUENCE: 40

Ser Leu Met Val Thr Asn Asp Gly Ala Thr Ile Leu Lys Asn
1               5                   10

<210> SEQ ID NO 41
<211> LENGTH: 17
<212> TYPE: PRT
<213> ORGANISM: Homo sapiens
```

```
<400> SEQUENCE: 41

Ala Thr Gln Tyr Phe Ala Asp Arg Asp Met Phe Cys Ala Gly Arg Val
1               5                   10                  15

Pro

<210> SEQ ID NO 42
<211> LENGTH: 18
<212> TYPE: PRT
<213> ORGANISM: Homo sapiens

<400> SEQUENCE: 42

Val Ala Thr Gln Tyr Phe Ala Asp Arg Asp Met Phe Cys Ala Gly Arg
1               5                   10                  15

Val Pro

<210> SEQ ID NO 43
<211> LENGTH: 15
<212> TYPE: PRT
<213> ORGANISM: Homo sapiens

<400> SEQUENCE: 43

Gly Pro Lys Pro Leu Phe Arg Arg Met Ser Ser Leu Val Gly Pro
1               5                   10                  15

<210> SEQ ID NO 44
<211> LENGTH: 16
<212> TYPE: PRT
<213> ORGANISM: Homo sapiens

<400> SEQUENCE: 44

Gly Pro Lys Pro Leu Phe Arg Arg Met Ser Ser Leu Val Gly Pro Thr
1               5                   10                  15

<210> SEQ ID NO 45
<211> LENGTH: 18
<212> TYPE: PRT
<213> ORGANISM: Homo sapiens

<400> SEQUENCE: 45

Gly Pro Lys Pro Leu Phe Arg Arg Met Ser Ser Leu Val Gly Pro Thr
1               5                   10                  15

Gln Ser

<210> SEQ ID NO 46
<211> LENGTH: 19
<212> TYPE: PRT
<213> ORGANISM: Homo sapiens

<400> SEQUENCE: 46

Ser Gly Pro Lys Pro Leu Phe Arg Arg Met Ser Ser Leu Val Gly Pro
1               5                   10                  15

Thr Gln Ser

<210> SEQ ID NO 47
<211> LENGTH: 20
<212> TYPE: PRT
<213> ORGANISM: Homo sapiens

<400> SEQUENCE: 47

Ser Gly Pro Lys Pro Leu Phe Arg Arg Met Ser Ser Leu Val Gly Pro
1               5                   10                  15
```

-continued

Thr Gln Ser Phe
        20

<210> SEQ ID NO 48
<211> LENGTH: 10
<212> TYPE: PRT
<213> ORGANISM: Homo sapiens

<400> SEQUENCE: 48

Arg Asp Met Phe Thr Leu Glu Asp Thr Leu
1               5                   10

<210> SEQ ID NO 49
<211> LENGTH: 12
<212> TYPE: PRT
<213> ORGANISM: Homo sapiens

<400> SEQUENCE: 49

Arg Asp Met Phe Thr Leu Glu Asp Thr Leu Leu Gly
1               5                   10

<210> SEQ ID NO 50
<211> LENGTH: 16
<212> TYPE: PRT
<213> ORGANISM: Homo sapiens

<400> SEQUENCE: 50

Arg Asp Met Phe Thr Leu Glu Asp Thr Leu Leu Gly Tyr Leu Ala Asp
1               5                   10                  15

<210> SEQ ID NO 51
<211> LENGTH: 12
<212> TYPE: PRT
<213> ORGANISM: Homo sapiens

<400> SEQUENCE: 51

Val Gln Arg Asp Met Phe Thr Leu Glu Asp Thr Leu
1               5                   10

<210> SEQ ID NO 52
<211> LENGTH: 18
<212> TYPE: PRT
<213> ORGANISM: Homo sapiens

<400> SEQUENCE: 52

Ser Pro Gly Glu Pro Gln Ile Ile Phe Cys Arg Ser Glu Ala Ala His
1               5                   10                  15

Gln Gly

<210> SEQ ID NO 53
<211> LENGTH: 20
<212> TYPE: PRT
<213> ORGANISM: Homo sapiens

<400> SEQUENCE: 53

Ser Pro Gly Glu Pro Gln Ile Ile Phe Cys Arg Ser Glu Ala Ala His
1               5                   10                  15

Gln Gly Val Ile
        20

<210> SEQ ID NO 54
<211> LENGTH: 18
<212> TYPE: PRT
<213> ORGANISM: Homo sapiens

```
<400> SEQUENCE: 54

Ala Thr Pro Leu Leu Met Gln Ala Leu Pro Met Gly Ala Leu Pro Gln
1               5                   10                  15

Gly Pro

<210> SEQ ID NO 55
<211> LENGTH: 13
<212> TYPE: PRT
<213> ORGANISM: Homo sapiens

<400> SEQUENCE: 55

Gly His Leu Lys Ile Met His Asp Ala Ile Gly Phe Arg
1               5                   10

<210> SEQ ID NO 56
<211> LENGTH: 14
<212> TYPE: PRT
<213> ORGANISM: Homo sapiens

<400> SEQUENCE: 56

Leu Gly His Leu Lys Ile Met His Asp Ala Ile Gly Phe Arg
1               5                   10

<210> SEQ ID NO 57
<211> LENGTH: 15
<212> TYPE: PRT
<213> ORGANISM: Homo sapiens

<400> SEQUENCE: 57

Asn Pro Pro Leu Phe Ala Leu Asp Lys Asp Ala Pro Leu Arg Tyr
1               5                   10                  15

<210> SEQ ID NO 58
<211> LENGTH: 16
<212> TYPE: PRT
<213> ORGANISM: Homo sapiens

<400> SEQUENCE: 58

Leu Glu Lys Ile Val Leu Asp Asn Ser Val Phe Ser Glu His Arg Asn
1               5                   10                  15

<210> SEQ ID NO 59
<211> LENGTH: 16
<212> TYPE: PRT
<213> ORGANISM: Homo sapiens

<400> SEQUENCE: 59

Gly Gln Arg Arg Phe Asn Leu Gln Lys Asn Phe Val Gly Lys Val Ala
1               5                   10                  15

<210> SEQ ID NO 60
<211> LENGTH: 18
<212> TYPE: PRT
<213> ORGANISM: Homo sapiens

<400> SEQUENCE: 60

Ile Gly Gln Arg Arg Phe Asn Leu Gln Lys Asn Phe Val Gly Lys Val
1               5                   10                  15

Ala Leu

<210> SEQ ID NO 61
<211> LENGTH: 14
<212> TYPE: PRT
```

<213> ORGANISM: Homo sapiens

<400> SEQUENCE: 61

Arg Arg Phe Asn Leu Gln Lys Asn Phe Val Gly Lys Val Ala
1               5                   10

<210> SEQ ID NO 62
<211> LENGTH: 15
<212> TYPE: PRT
<213> ORGANISM: Homo sapiens

<400> SEQUENCE: 62

Val Pro Gly Thr Tyr Lys Ile Thr Ala Ser Ala Arg Gly Tyr Asn
1               5                   10                  15

<210> SEQ ID NO 63
<211> LENGTH: 15
<212> TYPE: PRT
<213> ORGANISM: Homo sapiens

<400> SEQUENCE: 63

Leu Ala Lys Trp Val Ala Ile Gln Ser Val Ser Ala Trp Pro Glu
1               5                   10                  15

<210> SEQ ID NO 64
<211> LENGTH: 14
<212> TYPE: PRT
<213> ORGANISM: Homo sapiens

<400> SEQUENCE: 64

Val Ala Arg Phe Ala Ala Ala Thr Gln Gln Gln Thr Ala
1               5                   10

<210> SEQ ID NO 65
<211> LENGTH: 14
<212> TYPE: PRT
<213> ORGANISM: Homo sapiens

<400> SEQUENCE: 65

Trp Gly Ala Leu Ala Thr Ile Ser Thr Leu Glu Ala Val Arg
1               5                   10

<210> SEQ ID NO 66
<211> LENGTH: 16
<212> TYPE: PRT
<213> ORGANISM: Homo sapiens

<400> SEQUENCE: 66

Val Gly Val Pro Tyr Arg Ile Thr Val Thr Ala Val Ser Ala Ser Gly
1               5                   10                  15

<210> SEQ ID NO 67
<211> LENGTH: 14
<212> TYPE: PRT
<213> ORGANISM: Homo sapiens

<400> SEQUENCE: 67

Val Pro Tyr Arg Ile Thr Val Thr Ala Val Ser Ala Ser Gly
1               5                   10

<210> SEQ ID NO 68
<211> LENGTH: 15
<212> TYPE: PRT
<213> ORGANISM: Homo sapiens

<400> SEQUENCE: 68

Asp His Asn Phe Val Lys Ala Ile Asn Ala Ile Gln Lys Ser Trp
1               5                   10                  15

<210> SEQ ID NO 69
<211> LENGTH: 18
<212> TYPE: PRT
<213> ORGANISM: Homo sapiens

<400> SEQUENCE: 69

Lys Lys Val Val Val Tyr Leu Gln Lys Leu Asp Thr Ala Tyr Asp Asp
1               5                   10                  15

Leu Gly

<210> SEQ ID NO 70
<211> LENGTH: 18
<212> TYPE: PRT
<213> ORGANISM: Homo sapiens

<400> SEQUENCE: 70

Lys Tyr Asp His Asn Phe Val Lys Ala Ile Asn Ala Ile Gln Lys Ser
1               5                   10                  15

Trp Thr

<210> SEQ ID NO 71
<211> LENGTH: 17
<212> TYPE: PRT
<213> ORGANISM: Homo sapiens

<400> SEQUENCE: 71

Ser Gly Met Asp Tyr Trp Ile Val Lys Asn Ser Trp Gly Thr Gly Trp
1               5                   10                  15

Gly

<210> SEQ ID NO 72
<211> LENGTH: 14
<212> TYPE: PRT
<213> ORGANISM: Homo sapiens

<400> SEQUENCE: 72

Tyr Asp His Asn Phe Val Lys Ala Ile Asn Ala Ile Gln Lys
1               5                   10

<210> SEQ ID NO 73
<211> LENGTH: 17
<212> TYPE: PRT
<213> ORGANISM: Homo sapiens

<400> SEQUENCE: 73

Tyr Asp His Asn Phe Val Lys Ala Ile Asn Ala Ile Gln Lys Ser Trp
1               5                   10                  15

Thr

<210> SEQ ID NO 74
<211> LENGTH: 15
<212> TYPE: PRT
<213> ORGANISM: Homo sapiens

<400> SEQUENCE: 74

Ile Phe Ser Phe Tyr Leu Ser Arg Asp Pro Asp Ala Gln Pro Gly
1               5                   10                  15

<210> SEQ ID NO 75

```
<211> LENGTH: 12
<212> TYPE: PRT
<213> ORGANISM: Homo sapiens

<400> SEQUENCE: 75

Leu Ser Arg Asp Pro Asp Ala Gln Pro Gly Gly Glu
1               5                   10

<210> SEQ ID NO 76
<211> LENGTH: 14
<212> TYPE: PRT
<213> ORGANISM: Homo sapiens

<400> SEQUENCE: 76

Gly Lys Glu Tyr Trp Leu Val Lys Asn Ser Trp Gly His Asn
1               5                   10

<210> SEQ ID NO 77
<211> LENGTH: 15
<212> TYPE: PRT
<213> ORGANISM: Homo sapiens

<400> SEQUENCE: 77

Lys Asn Leu Lys Phe Val Met Leu His Asn Leu Glu His Ser Met
1               5                   10                  15

<210> SEQ ID NO 78
<211> LENGTH: 14
<212> TYPE: PRT
<213> ORGANISM: Homo sapiens

<400> SEQUENCE: 78

Thr Thr Ala Phe Gln Tyr Ile Ile Asp Asn Lys Gly Ile Asp
1               5                   10

<210> SEQ ID NO 79
<211> LENGTH: 15
<212> TYPE: PRT
<213> ORGANISM: Homo sapiens

<400> SEQUENCE: 79

Gly Thr Glu Tyr Trp Ile Val Arg Asn Ser Trp Gly Glu Pro Trp
1               5                   10                  15

<210> SEQ ID NO 80
<211> LENGTH: 11
<212> TYPE: PRT
<213> ORGANISM: Homo sapiens

<400> SEQUENCE: 80

Gly Tyr Leu Pro Asn Gln Leu Phe Arg Thr Phe
1               5                   10

<210> SEQ ID NO 81
<211> LENGTH: 13
<212> TYPE: PRT
<213> ORGANISM: Homo sapiens

<400> SEQUENCE: 81

Ile Arg Phe Val Val Asp Ser Gly Lys Val Lys Glu Met
1               5                   10

<210> SEQ ID NO 82
<211> LENGTH: 15
<212> TYPE: PRT
```

```
<400> SEQUENCE: 82

Met Glu Lys Tyr Asn Ile Glu Lys Asp Ile Ala Ala Tyr Ile Lys
1               5                   10                  15

<210> SEQ ID NO 83
<211> LENGTH: 14
<212> TYPE: PRT
<213> ORGANISM: Homo sapiens

<400> SEQUENCE: 83

Leu Pro Phe Gly Ala Gln Ser Thr Gln Arg Gly His Thr Glu
1               5                   10

<210> SEQ ID NO 84
<211> LENGTH: 15
<212> TYPE: PRT
<213> ORGANISM: Homo sapiens

<400> SEQUENCE: 84

Ser Lys Tyr Tyr Val Thr Ile Ile Asp Ala Pro Gly His Arg Asp
1               5                   10                  15

<210> SEQ ID NO 85
<211> LENGTH: 14
<212> TYPE: PRT
<213> ORGANISM: Homo sapiens

<400> SEQUENCE: 85

Ile Glu Lys Phe Glu Lys Glu Ala Ala Glu Met Gly Lys Gly
1               5                   10

<210> SEQ ID NO 86
<211> LENGTH: 15
<212> TYPE: PRT
<213> ORGANISM: Homo sapiens

<400> SEQUENCE: 86

Ile Glu Lys Phe Glu Lys Glu Ala Ala Glu Met Gly Lys Gly Ser
1               5                   10                  15

<210> SEQ ID NO 87
<211> LENGTH: 16
<212> TYPE: PRT
<213> ORGANISM: Homo sapiens

<400> SEQUENCE: 87

Ile Glu Lys Phe Glu Lys Glu Ala Ala Glu Met Gly Lys Gly Ser Phe
1               5                   10                  15

<210> SEQ ID NO 88
<211> LENGTH: 17
<212> TYPE: PRT
<213> ORGANISM: Homo sapiens

<400> SEQUENCE: 88

Thr Ile Glu Lys Phe Glu Lys Glu Ala Ala Glu Met Gly Lys Gly Ser
1               5                   10                  15

Phe

<210> SEQ ID NO 89
<211> LENGTH: 15
<212> TYPE: PRT
<213> ORGANISM: Homo sapiens
```

<400> SEQUENCE: 89

Asp Ile Asp Ala Ile Phe Lys Asp Leu Ser Ile Arg Ser Val Arg
1               5                   10                  15

<210> SEQ ID NO 90
<211> LENGTH: 14
<212> TYPE: PRT
<213> ORGANISM: Homo sapiens

<400> SEQUENCE: 90

Gly Val Pro Leu Tyr Arg His Ile Ala Asp Leu Ala Gly Asn
1               5                   10

<210> SEQ ID NO 91
<211> LENGTH: 17
<212> TYPE: PRT
<213> ORGANISM: Homo sapiens

<400> SEQUENCE: 91

Gly Val Pro Leu Tyr Arg His Ile Ala Asp Leu Ala Gly Asn Ser Glu
1               5                   10                  15

Val

<210> SEQ ID NO 92
<211> LENGTH: 16
<212> TYPE: PRT
<213> ORGANISM: Homo sapiens

<400> SEQUENCE: 92

Ile Lys Glu Lys Tyr Gly Lys Asp Ala Thr Asn Val Gly Asp Glu Gly
1               5                   10                  15

<210> SEQ ID NO 93
<211> LENGTH: 17
<212> TYPE: PRT
<213> ORGANISM: Homo sapiens

<400> SEQUENCE: 93

Ile Lys Glu Lys Tyr Gly Lys Asp Ala Thr Asn Val Gly Asp Glu Gly
1               5                   10                  15

Gly

<210> SEQ ID NO 94
<211> LENGTH: 16
<212> TYPE: PRT
<213> ORGANISM: Homo sapiens

<400> SEQUENCE: 94

Lys Glu Lys Tyr Gly Lys Asp Ala Thr Asn Val Gly Asp Glu Gly Gly
1               5                   10                  15

<210> SEQ ID NO 95
<211> LENGTH: 18
<212> TYPE: PRT
<213> ORGANISM: Homo sapiens

<400> SEQUENCE: 95

Val Ile Lys Glu Lys Tyr Gly Lys Asp Ala Thr Asn Val Gly Asp Glu
1               5                   10                  15

Gly Gly

<210> SEQ ID NO 96

```
<211> LENGTH: 13
<212> TYPE: PRT
<213> ORGANISM: Homo sapiens

<400> SEQUENCE: 96

Val Pro Leu Tyr Arg His Ile Ala Asp Leu Ala Gly Asn
1               5                   10

<210> SEQ ID NO 97
<211> LENGTH: 15
<212> TYPE: PRT
<213> ORGANISM: Homo sapiens

<400> SEQUENCE: 97

Val Pro Leu Tyr Arg His Ile Ala Asp Leu Ala Gly Asn Ser Glu
1               5                   10                  15

<210> SEQ ID NO 98
<211> LENGTH: 16
<212> TYPE: PRT
<213> ORGANISM: Homo sapiens

<400> SEQUENCE: 98

Val Pro Leu Tyr Arg His Ile Ala Asp Leu Ala Gly Asn Ser Glu Val
1               5                   10                  15

<210> SEQ ID NO 99
<211> LENGTH: 17
<212> TYPE: PRT
<213> ORGANISM: Homo sapiens

<400> SEQUENCE: 99

Val Pro Leu Tyr Arg His Ile Ala Asp Leu Ala Gly Asn Ser Glu Val
1               5                   10                  15

Ile

<210> SEQ ID NO 100
<211> LENGTH: 11
<212> TYPE: PRT
<213> ORGANISM: Homo sapiens

<400> SEQUENCE: 100

Leu Leu Gln Lys Leu Ile Leu Trp Arg Val Leu
1               5                   10

<210> SEQ ID NO 101
<211> LENGTH: 16
<212> TYPE: PRT
<213> ORGANISM: Homo sapiens

<400> SEQUENCE: 101

Leu Gln Asn Ile Ile Pro Ala Ser Thr Gly Ala Ala Lys Ala Val Gly
1               5                   10                  15

<210> SEQ ID NO 102
<211> LENGTH: 17
<212> TYPE: PRT
<213> ORGANISM: Homo sapiens

<400> SEQUENCE: 102

Glu Pro Ile Glu Gln Lys Phe Val Ser Ile Ser Asp Leu Leu Val Pro
1               5                   10                  15

Lys
```

<210> SEQ ID NO 103
<211> LENGTH: 14
<212> TYPE: PRT
<213> ORGANISM: Homo sapiens

<400> SEQUENCE: 103

Ala Ile Phe Leu Phe Val Asp Lys Thr Val Pro Gln Ser Ser
1               5                   10

<210> SEQ ID NO 104
<211> LENGTH: 15
<212> TYPE: PRT
<213> ORGANISM: Homo sapiens

<400> SEQUENCE: 104

Ala Ile Phe Leu Phe Val Asp Lys Thr Val Pro Gln Ser Ser Leu
1               5                   10                  15

<210> SEQ ID NO 105
<211> LENGTH: 16
<212> TYPE: PRT
<213> ORGANISM: Homo sapiens

<400> SEQUENCE: 105

Ala Ile Phe Leu Phe Val Asp Lys Thr Val Pro Gln Ser Ser Leu Thr
1               5                   10                  15

<210> SEQ ID NO 106
<211> LENGTH: 11
<212> TYPE: PRT
<213> ORGANISM: Homo sapiens

<400> SEQUENCE: 106

Phe Val Asp Lys Thr Val Pro Gln Ser Ser Leu
1               5                   10

<210> SEQ ID NO 107
<211> LENGTH: 21
<212> TYPE: PRT
<213> ORGANISM: Homo sapiens

<400> SEQUENCE: 107

Leu Pro Ser Glu Lys Ala Ile Phe Leu Phe Val Asp Lys Thr Val Pro
1               5                   10                  15

Gln Ser Ser Leu Thr
            20

<210> SEQ ID NO 108
<211> LENGTH: 16
<212> TYPE: PRT
<213> ORGANISM: Homo sapiens

<400> SEQUENCE: 108

Lys Val Asn Leu Leu Lys Ile Lys Thr Glu Leu Cys Lys Lys Glu Val
1               5                   10                  15

<210> SEQ ID NO 109
<211> LENGTH: 14
<212> TYPE: PRT
<213> ORGANISM: Homo sapiens

<400> SEQUENCE: 109

Leu Gly Lys Trp Cys Ser Glu Lys Thr Glu Thr Gly Gln Glu
1               5                   10

```
<210> SEQ ID NO 110
<211> LENGTH: 15
<212> TYPE: PRT
<213> ORGANISM: Homo sapiens

<400> SEQUENCE: 110

Val Asn Leu Leu Lys Ile Lys Thr Glu Leu Cys Lys Lys Glu Val
1               5                   10                  15

<210> SEQ ID NO 111
<211> LENGTH: 13
<212> TYPE: PRT
<213> ORGANISM: Homo sapiens

<400> SEQUENCE: 111

Gly Asn Tyr Arg Ile Glu Ser Val Leu Ser Ser Ser Gly
1               5                   10

<210> SEQ ID NO 112
<211> LENGTH: 14
<212> TYPE: PRT
<213> ORGANISM: Homo sapiens

<400> SEQUENCE: 112

Gly Asn Tyr Arg Ile Glu Ser Val Leu Ser Ser Ser Gly Lys
1               5                   10

<210> SEQ ID NO 113
<211> LENGTH: 13
<212> TYPE: PRT
<213> ORGANISM: Homo sapiens

<400> SEQUENCE: 113

Leu Gly Cys Ile Lys Ile Ala Ala Ser Leu Lys Gly Ile
1               5                   10

<210> SEQ ID NO 114
<211> LENGTH: 14
<212> TYPE: PRT
<213> ORGANISM: Homo sapiens

<400> SEQUENCE: 114

Arg Leu Gly Cys Ile Lys Ile Ala Ala Ser Leu Lys Gly Ile
1               5                   10

<210> SEQ ID NO 115
<211> LENGTH: 14
<212> TYPE: PRT
<213> ORGANISM: Homo sapiens

<400> SEQUENCE: 115

Thr Gly Asn Tyr Arg Ile Glu Ser Val Leu Ser Ser Ser Gly
1               5                   10

<210> SEQ ID NO 116
<211> LENGTH: 15
<212> TYPE: PRT
<213> ORGANISM: Homo sapiens

<400> SEQUENCE: 116

Thr Gly Asn Tyr Arg Ile Glu Ser Val Leu Ser Ser Ser Gly Lys
1               5                   10                  15

<210> SEQ ID NO 117
```

```
<211> LENGTH: 16
<212> TYPE: PRT
<213> ORGANISM: Homo sapiens

<400> SEQUENCE: 117

Thr Gly Asn Tyr Arg Ile Glu Ser Val Leu Ser Ser Ser Gly Lys Arg
1               5                   10                  15

<210> SEQ ID NO 118
<211> LENGTH: 15
<212> TYPE: PRT
<213> ORGANISM: Homo sapiens

<400> SEQUENCE: 118

Thr Thr Gly Asn Tyr Arg Ile Glu Ser Val Leu Ser Ser Ser Gly
1               5                   10                  15

<210> SEQ ID NO 119
<211> LENGTH: 16
<212> TYPE: PRT
<213> ORGANISM: Homo sapiens

<400> SEQUENCE: 119

Thr Thr Gly Asn Tyr Arg Ile Glu Ser Val Leu Ser Ser Ser Gly Lys
1               5                   10                  15

<210> SEQ ID NO 120
<211> LENGTH: 15
<212> TYPE: PRT
<213> ORGANISM: Homo sapiens

<400> SEQUENCE: 120

Val Thr Arg Ala Phe Val Ala Ala Arg Thr Phe Ala Gln Gly Leu
1               5                   10                  15

<210> SEQ ID NO 121
<211> LENGTH: 13
<212> TYPE: PRT
<213> ORGANISM: Homo sapiens

<400> SEQUENCE: 121

Asp Ile Phe Glu Arg Ile Ala Ser Glu Ala Ser Arg Leu
1               5                   10

<210> SEQ ID NO 122
<211> LENGTH: 14
<212> TYPE: PRT
<213> ORGANISM: Homo sapiens

<400> SEQUENCE: 122

Asp Ile Phe Glu Arg Ile Ala Ser Glu Ala Ser Arg Leu Ala
1               5                   10

<210> SEQ ID NO 123
<211> LENGTH: 15
<212> TYPE: PRT
<213> ORGANISM: Homo sapiens

<400> SEQUENCE: 123

Asp Ile Phe Glu Arg Ile Ala Ser Glu Ala Ser Arg Leu Ala His
1               5                   10                  15

<210> SEQ ID NO 124
<211> LENGTH: 16
<212> TYPE: PRT
```

```
<400> SEQUENCE: 124

Asp Ile Phe Glu Arg Ile Ala Ser Glu Ala Ser Arg Leu Ala His Tyr
1               5                   10                  15

<210> SEQ ID NO 125
<211> LENGTH: 19
<212> TYPE: PRT
<213> ORGANISM: Homo sapiens

<400> SEQUENCE: 125

Val Asn Asp Ile Phe Glu Arg Ile Ala Ser Glu Ala Ser Arg Leu Ala
1               5                   10                  15

His Tyr Asn

<210> SEQ ID NO 126
<211> LENGTH: 16
<212> TYPE: PRT
<213> ORGANISM: Homo sapiens

<400> SEQUENCE: 126

Asp Asp Thr Gln Phe Val Arg Phe Asp Ser Asp Ala Ala Ser Gln Arg
1               5                   10                  15

<210> SEQ ID NO 127
<211> LENGTH: 18
<212> TYPE: PRT
<213> ORGANISM: Homo sapiens

<400> SEQUENCE: 127

Asp Asp Thr Gln Phe Val Arg Phe Asp Ser Asp Ala Ala Ser Gln Arg
1               5                   10                  15

Met Glu

<210> SEQ ID NO 128
<211> LENGTH: 19
<212> TYPE: PRT
<213> ORGANISM: Homo sapiens

<400> SEQUENCE: 128

Asp Asp Thr Gln Phe Val Arg Phe Asp Ser Asp Ala Ala Ser Gln Arg
1               5                   10                  15

Met Glu Pro

<210> SEQ ID NO 129
<211> LENGTH: 20
<212> TYPE: PRT
<213> ORGANISM: Homo sapiens

<400> SEQUENCE: 129

Asp Asp Thr Gln Phe Val Arg Phe Asp Ser Asp Ala Ala Ser Gln Arg
1               5                   10                  15

Met Glu Pro Arg
            20

<210> SEQ ID NO 130
<211> LENGTH: 17
<212> TYPE: PRT
<213> ORGANISM: Homo sapiens

<400> SEQUENCE: 130

Asp Thr Glu Phe Val Arg Phe Asp Ser Asp Ala Ala Ser Gln Arg Met
1               5                   10                  15
```

<210> SEQ ID NO 131
<211> LENGTH: 18
<212> TYPE: PRT
<213> ORGANISM: Homo sapiens

<400> SEQUENCE: 131

Asp Thr Glu Phe Val Arg Phe Asp Ser Asp Ala Ala Ser Gln Arg Met
1               5                   10                  15

Glu Pro

<210> SEQ ID NO 132
<211> LENGTH: 14
<212> TYPE: PRT
<213> ORGANISM: Homo sapiens

<400> SEQUENCE: 132

Asp Thr Gln Phe Val Arg Phe Asp Ser Asp Ala Ala Ser Gln
1               5                   10

<210> SEQ ID NO 133
<211> LENGTH: 15
<212> TYPE: PRT
<213> ORGANISM: Homo sapiens

<400> SEQUENCE: 133

Asp Thr Gln Phe Val Arg Phe Asp Ser Asp Ala Ala Ser Gln Arg
1               5                   10                  15

<210> SEQ ID NO 134
<211> LENGTH: 16
<212> TYPE: PRT
<213> ORGANISM: Homo sapiens

<400> SEQUENCE: 134

Asp Thr Gln Phe Val Arg Phe Asp Ser Asp Ala Ala Ser Gln Arg Met
1               5                   10                  15

<210> SEQ ID NO 135
<211> LENGTH: 17
<212> TYPE: PRT
<213> ORGANISM: Homo sapiens

<400> SEQUENCE: 135

Asp Thr Gln Phe Val Arg Phe Asp Ser Asp Ala Ala Ser Gln Arg Met
1               5                   10                  15

Glu

<210> SEQ ID NO 136
<211> LENGTH: 18
<212> TYPE: PRT
<213> ORGANISM: Homo sapiens

<400> SEQUENCE: 136

Asp Thr Gln Phe Val Arg Phe Asp Ser Asp Ala Ala Ser Gln Arg Met
1               5                   10                  15

Glu Pro

<210> SEQ ID NO 137
<211> LENGTH: 21
<212> TYPE: PRT
<213> ORGANISM: Homo sapiens

```
<400> SEQUENCE: 137

Asp Thr Gln Phe Val Arg Phe Asp Ser Asp Ala Ala Ser Gln Arg Met
1               5                   10                  15

Glu Pro Arg Ala Pro
            20

<210> SEQ ID NO 138
<211> LENGTH: 12
<212> TYPE: PRT
<213> ORGANISM: Homo sapiens

<400> SEQUENCE: 138

Phe Val Arg Phe Asp Ser Asp Ala Ala Ser Gln Arg
1               5                   10

<210> SEQ ID NO 139
<211> LENGTH: 14
<212> TYPE: PRT
<213> ORGANISM: Homo sapiens

<400> SEQUENCE: 139

Phe Val Arg Phe Asp Ser Asp Ala Ala Ser Gln Arg Met Glu
1               5                   10

<210> SEQ ID NO 140
<211> LENGTH: 14
<212> TYPE: PRT
<213> ORGANISM: Homo sapiens

<400> SEQUENCE: 140

Lys His Lys Trp Glu Ala Ala His Val Ala Glu Gln Leu Arg
1               5                   10

<210> SEQ ID NO 141
<211> LENGTH: 15
<212> TYPE: PRT
<213> ORGANISM: Homo sapiens

<400> SEQUENCE: 141

Gln Phe Val Arg Phe Asp Ser Asp Ala Ala Ser Gln Arg Met Glu
1               5                   10                  15

<210> SEQ ID NO 142
<211> LENGTH: 13
<212> TYPE: PRT
<213> ORGANISM: Homo sapiens

<400> SEQUENCE: 142

Thr Gln Phe Val Arg Phe Asp Ser Asp Ala Ala Ser Gln
1               5                   10

<210> SEQ ID NO 143
<211> LENGTH: 14
<212> TYPE: PRT
<213> ORGANISM: Homo sapiens

<400> SEQUENCE: 143

Thr Gln Phe Val Arg Phe Asp Ser Asp Ala Ala Ser Gln Arg
1               5                   10

<210> SEQ ID NO 144
<211> LENGTH: 16
<212> TYPE: PRT
<213> ORGANISM: Homo sapiens
```

<400> SEQUENCE: 144

Thr Thr Lys His Lys Trp Glu Ala Ala His Val Ala Glu Gln Leu Arg
1               5                   10                  15

<210> SEQ ID NO 145
<211> LENGTH: 17
<212> TYPE: PRT
<213> ORGANISM: Homo sapiens

<400> SEQUENCE: 145

Val Asp Asp Thr Glu Phe Val Arg Phe Asp Ser Asp Ala Ala Ser Gln
1               5                   10                  15

Arg

<210> SEQ ID NO 146
<211> LENGTH: 24
<212> TYPE: PRT
<213> ORGANISM: Homo sapiens

<400> SEQUENCE: 146

Val Asp Asp Thr Gln Phe Val Arg Phe Asp Ser Asp Ala Ala Ser Gln
1               5                   10                  15

Arg Met Glu Pro Arg Ala Pro Trp
            20

<210> SEQ ID NO 147
<211> LENGTH: 26
<212> TYPE: PRT
<213> ORGANISM: Homo sapiens

<400> SEQUENCE: 147

Val Asp Asp Thr Gln Phe Val Arg Phe Asp Ser Asp Ala Ala Ser Gln
1               5                   10                  15

Arg Met Glu Pro Arg Ala Pro Trp Ile Glu
            20                  25

<210> SEQ ID NO 148
<211> LENGTH: 15
<212> TYPE: PRT
<213> ORGANISM: Homo sapiens

<400> SEQUENCE: 148

Asp Leu Ser Ser Trp Thr Ala Ala Asp Thr Ala Ala Gln Ile Thr
1               5                   10                  15

<210> SEQ ID NO 149
<211> LENGTH: 16
<212> TYPE: PRT
<213> ORGANISM: Homo sapiens

<400> SEQUENCE: 149

Asp Leu Ser Ser Trp Thr Ala Ala Asp Thr Ala Ala Gln Ile Thr Gln
1               5                   10                  15

<210> SEQ ID NO 150
<211> LENGTH: 19
<212> TYPE: PRT
<213> ORGANISM: Homo sapiens

<400> SEQUENCE: 150

Asp Leu Ser Ser Trp Thr Ala Ala Asp Thr Ala Ala Gln Ile Thr Gln
1               5                   10                  15

Arg Lys Trp

<210> SEQ ID NO 151
<211> LENGTH: 25
<212> TYPE: PRT
<213> ORGANISM: Homo sapiens

<400> SEQUENCE: 151

Asp Leu Ser Ser Trp Thr Ala Ala Asp Thr Ala Ala Gln Ile Thr Gln
1               5                   10                  15

Arg Lys Trp Glu Ala Ala Arg Val Ala
            20                  25

<210> SEQ ID NO 152
<211> LENGTH: 21
<212> TYPE: PRT
<213> ORGANISM: Homo sapiens

<400> SEQUENCE: 152

Asp Thr Leu Phe Val Arg Phe Asp Ser Asp Ala Thr Ser Pro Arg Lys
1               5                   10                  15

Glu Pro Arg Ala Pro
            20

<210> SEQ ID NO 153
<211> LENGTH: 16
<212> TYPE: PRT
<213> ORGANISM: Homo sapiens

<400> SEQUENCE: 153

Glu Asp Leu Ser Ser Trp Thr Ala Ala Asp Thr Ala Ala Gln Ile Thr
1               5                   10                  15

<210> SEQ ID NO 154
<211> LENGTH: 18
<212> TYPE: PRT
<213> ORGANISM: Homo sapiens

<400> SEQUENCE: 154

Glu Asp Leu Ser Ser Trp Thr Ala Ala Asp Thr Ala Ala Gln Ile Thr
1               5                   10                  15

Gln Arg

<210> SEQ ID NO 155
<211> LENGTH: 20
<212> TYPE: PRT
<213> ORGANISM: Homo sapiens

<400> SEQUENCE: 155

Glu Asp Leu Ser Ser Trp Thr Ala Ala Asp Thr Ala Ala Gln Ile Thr
1               5                   10                  15

Gln Arg Lys Trp
            20

<210> SEQ ID NO 156
<211> LENGTH: 21
<212> TYPE: PRT
<213> ORGANISM: Homo sapiens

<400> SEQUENCE: 156

Glu Asp Leu Ser Ser Trp Thr Ala Ala Asp Thr Ala Ala Gln Ile Thr
1               5                   10                  15

```
Gln Arg Lys Trp Glu
        20

<210> SEQ ID NO 157
<211> LENGTH: 26
<212> TYPE: PRT
<213> ORGANISM: Homo sapiens

<400> SEQUENCE: 157

Glu Asp Leu Ser Ser Trp Thr Ala Ala Asp Thr Ala Ala Gln Ile Thr
1               5                   10                  15

Gln Arg Lys Trp Glu Ala Ala Arg Val Ala
        20                  25

<210> SEQ ID NO 158
<211> LENGTH: 15
<212> TYPE: PRT
<213> ORGANISM: Homo sapiens

<400> SEQUENCE: 158

Gly Pro Glu Tyr Trp Asp Arg Glu Thr Gln Ile Ser Lys Thr Asn
1               5                   10                  15

<210> SEQ ID NO 159
<211> LENGTH: 15
<212> TYPE: PRT
<213> ORGANISM: Homo sapiens

<400> SEQUENCE: 159

Lys Asp Tyr Ile Ala Leu Asn Glu Asp Leu Ser Ser Trp Thr Ala
1               5                   10                  15

<210> SEQ ID NO 160
<211> LENGTH: 23
<212> TYPE: PRT
<213> ORGANISM: Homo sapiens

<400> SEQUENCE: 160

Leu Asn Glu Asp Leu Ser Ser Trp Thr Ala Ala Asp Thr Ala Ala Gln
1               5                   10                  15

Ile Thr Gln Arg Lys Trp Glu
        20

<210> SEQ ID NO 161
<211> LENGTH: 19
<212> TYPE: PRT
<213> ORGANISM: Homo sapiens

<400> SEQUENCE: 161

Leu Arg Trp Glu Pro Ser Ser Gln Ser Thr Val Pro Ile Val Gly Ile
1               5                   10                  15

Val Ala Gly

<210> SEQ ID NO 162
<211> LENGTH: 19
<212> TYPE: PRT
<213> ORGANISM: Homo sapiens

<400> SEQUENCE: 162

Leu Ser Ser Trp Thr Ala Ala Asp Thr Ala Ala Glu Ile Thr Glu Arg
1               5                   10                  15

Lys Trp Glu
```

-continued

<210> SEQ ID NO 163
<211> LENGTH: 16
<212> TYPE: PRT
<213> ORGANISM: Homo sapiens

<400> SEQUENCE: 163

Leu Ser Ser Trp Thr Ala Ala Asp Thr Ala Ala Gln Ile Thr Gln Arg
1               5                   10                  15

<210> SEQ ID NO 164
<211> LENGTH: 18
<212> TYPE: PRT
<213> ORGANISM: Homo sapiens

<400> SEQUENCE: 164

Leu Ser Ser Trp Thr Ala Ala Asp Thr Ala Ala Gln Ile Thr Gln Arg
1               5                   10                  15

Lys Trp

<210> SEQ ID NO 165
<211> LENGTH: 19
<212> TYPE: PRT
<213> ORGANISM: Homo sapiens

<400> SEQUENCE: 165

Leu Ser Ser Trp Thr Ala Ala Asp Thr Ala Ala Gln Ile Thr Gln Arg
1               5                   10                  15

Lys Trp Glu

<210> SEQ ID NO 166
<211> LENGTH: 21
<212> TYPE: PRT
<213> ORGANISM: Homo sapiens

<400> SEQUENCE: 166

Asn Glu Asp Leu Ser Ser Trp Thr Ala Ala Asp Thr Ala Ala Gln Ile
1               5                   10                  15

Thr Gln Arg Lys Trp
            20

<210> SEQ ID NO 167
<211> LENGTH: 13
<212> TYPE: PRT
<213> ORGANISM: Homo sapiens

<400> SEQUENCE: 167

Thr Leu Phe Val Arg Phe Asp Ser Asp Ala Thr Ser Pro
1               5                   10

<210> SEQ ID NO 168
<211> LENGTH: 23
<212> TYPE: PRT
<213> ORGANISM: Homo sapiens

<400> SEQUENCE: 168

Val Asp Asp Thr Leu Phe Val Arg Phe Asp Ser Asp Ala Thr Ser Pro
1               5                   10                  15

Arg Lys Glu Pro Arg Ala Pro
            20

<210> SEQ ID NO 169
<211> LENGTH: 16

```
<212> TYPE: PRT
<213> ORGANISM: Homo sapiens

<400> SEQUENCE: 169

Asp Asp Thr Gln Phe Val Gln Phe Asp Ser Asp Ala Ala Ser Pro Arg
1               5                   10                  15

<210> SEQ ID NO 170
<211> LENGTH: 16
<212> TYPE: PRT
<213> ORGANISM: Homo sapiens

<400> SEQUENCE: 170

Asp Gly Lys Asp Tyr Ile Ala Leu Asn Glu Asp Leu Arg Ser Trp Thr
1               5                   10                  15

<210> SEQ ID NO 171
<211> LENGTH: 17
<212> TYPE: PRT
<213> ORGANISM: Homo sapiens

<400> SEQUENCE: 171

Asp Gly Lys Asp Tyr Ile Ala Leu Asn Glu Asp Leu Arg Ser Trp Thr
1               5                   10                  15

Ala

<210> SEQ ID NO 172
<211> LENGTH: 18
<212> TYPE: PRT
<213> ORGANISM: Homo sapiens

<400> SEQUENCE: 172

Asp Gly Lys Asp Tyr Ile Ala Leu Asn Glu Asp Leu Arg Ser Trp Thr
1               5                   10                  15

Ala Ala

<210> SEQ ID NO 173
<211> LENGTH: 15
<212> TYPE: PRT
<213> ORGANISM: Homo sapiens

<400> SEQUENCE: 173

Asp Thr Gln Phe Val Gln Phe Asp Ser Asp Ala Ala Ser Pro Arg
1               5                   10                  15

<210> SEQ ID NO 174
<211> LENGTH: 16
<212> TYPE: PRT
<213> ORGANISM: Homo sapiens

<400> SEQUENCE: 174

Asp Thr Gln Phe Val Gln Phe Asp Ser Asp Ala Ala Ser Pro Arg Gly
1               5                   10                  15

<210> SEQ ID NO 175
<211> LENGTH: 19
<212> TYPE: PRT
<213> ORGANISM: Homo sapiens

<400> SEQUENCE: 175

Asp Thr Gln Phe Val Gln Phe Asp Ser Asp Ala Ala Ser Pro Arg Gly
1               5                   10                  15

Glu Pro Arg
```

```
<210> SEQ ID NO 176
<211> LENGTH: 21
<212> TYPE: PRT
<213> ORGANISM: Homo sapiens

<400> SEQUENCE: 176

Asp Thr Gln Phe Val Gln Phe Asp Ser Asp Ala Ala Ser Pro Arg Gly
1               5                   10                  15

Glu Pro Arg Ala Pro
            20

<210> SEQ ID NO 177
<211> LENGTH: 14
<212> TYPE: PRT
<213> ORGANISM: Homo sapiens

<400> SEQUENCE: 177

Asp Tyr Ile Ala Leu Asn Glu Asp Leu Arg Ser Trp Thr Ala
1               5                   10

<210> SEQ ID NO 178
<211> LENGTH: 15
<212> TYPE: PRT
<213> ORGANISM: Homo sapiens

<400> SEQUENCE: 178

Phe Val Gln Phe Asp Ser Asp Ala Ala Ser Pro Arg Gly Glu Pro
1               5                   10                  15

<210> SEQ ID NO 179
<211> LENGTH: 15
<212> TYPE: PRT
<213> ORGANISM: Homo sapiens

<400> SEQUENCE: 179

Gly Lys Asp Tyr Ile Ala Leu Asn Glu Asp Leu Arg Ser Trp Thr
1               5                   10                  15

<210> SEQ ID NO 180
<211> LENGTH: 15
<212> TYPE: PRT
<213> ORGANISM: Homo sapiens

<400> SEQUENCE: 180

Gly Arg Leu Leu Arg Gly Tyr Asn Gln Phe Ala Tyr Asp Gly Lys
1               5                   10                  15

<210> SEQ ID NO 181
<211> LENGTH: 13
<212> TYPE: PRT
<213> ORGANISM: Homo sapiens

<400> SEQUENCE: 181

Lys Asp Tyr Ile Ala Leu Asn Glu Asp Leu Arg Ser Trp
1               5                   10

<210> SEQ ID NO 182
<211> LENGTH: 14
<212> TYPE: PRT
<213> ORGANISM: Homo sapiens

<400> SEQUENCE: 182

Thr Gln Phe Val Gln Phe Asp Ser Asp Ala Ala Ser Pro Arg
1               5                   10
```

```
<210> SEQ ID NO 183
<211> LENGTH: 18
<212> TYPE: PRT
<213> ORGANISM: Homo sapiens

<400> SEQUENCE: 183

Thr Gln Phe Val Gln Phe Asp Ser Asp Ala Ala Ser Pro Arg Gly Glu
1               5                   10                  15

Pro Arg

<210> SEQ ID NO 184
<211> LENGTH: 21
<212> TYPE: PRT
<213> ORGANISM: Homo sapiens

<400> SEQUENCE: 184

Val Asp Asp Thr Gln Phe Val Gln Phe Asp Ser Asp Ala Ala Ser Pro
1               5                   10                  15

Arg Gly Glu Pro Arg
            20

<210> SEQ ID NO 185
<211> LENGTH: 23
<212> TYPE: PRT
<213> ORGANISM: Homo sapiens

<400> SEQUENCE: 185

Val Asp Asp Thr Gln Phe Val Gln Phe Asp Ser Asp Ala Ala Ser Pro
1               5                   10                  15

Arg Gly Glu Pro Arg Ala Pro
            20

<210> SEQ ID NO 186
<211> LENGTH: 24
<212> TYPE: PRT
<213> ORGANISM: Homo sapiens

<400> SEQUENCE: 186

Tyr Val Asp Asp Thr Gln Phe Val Gln Phe Asp Ser Asp Ala Ala Ser
1               5                   10                  15

Pro Arg Gly Glu Pro Arg Ala Pro
            20

<210> SEQ ID NO 187
<211> LENGTH: 15
<212> TYPE: PRT
<213> ORGANISM: Homo sapiens

<400> SEQUENCE: 187

Phe Gly Pro Thr Phe Val Ser Ala Val Asp Gly Leu Ser Phe Gln
1               5                   10                  15

<210> SEQ ID NO 188
<211> LENGTH: 16
<212> TYPE: PRT
<213> ORGANISM: Homo sapiens

<400> SEQUENCE: 188

Asn Arg Glu Glu Phe Val Arg Phe Asp Ser Asp Val Gly Glu Phe Arg
1               5                   10                  15

<210> SEQ ID NO 189
```

```
<211> LENGTH: 15
<212> TYPE: PRT
<213> ORGANISM: Homo sapiens

<400> SEQUENCE: 189

Arg Glu Glu Phe Val Arg Phe Asp Ser Asp Val Gly Glu Phe Arg
1               5                   10                  15

<210> SEQ ID NO 190
<211> LENGTH: 15
<212> TYPE: PRT
<213> ORGANISM: Homo sapiens

<400> SEQUENCE: 190

Asp Val Glu Val Tyr Arg Ala Val Thr Pro Leu Gly Pro Pro Asp
1               5                   10                  15

<210> SEQ ID NO 191
<211> LENGTH: 17
<212> TYPE: PRT
<213> ORGANISM: Homo sapiens

<400> SEQUENCE: 191

Ala Gln Gly Ala Leu Ala Asn Ile Ala Val Asp Lys Ala Asn Leu Glu
1               5                   10                  15

Ile

<210> SEQ ID NO 192
<211> LENGTH: 15
<212> TYPE: PRT
<213> ORGANISM: Homo sapiens

<400> SEQUENCE: 192

Ile Gln Ala Glu Phe Tyr Leu Asn Pro Asp Gln Ser Gly Glu Phe
1               5                   10                  15

<210> SEQ ID NO 193
<211> LENGTH: 15
<212> TYPE: PRT
<213> ORGANISM: Homo sapiens

<400> SEQUENCE: 193

Gly Ala Gly Leu Phe Ile Tyr Phe Arg Asn Gln Lys Gly His Ser
1               5                   10                  15

<210> SEQ ID NO 194
<211> LENGTH: 16
<212> TYPE: PRT
<213> ORGANISM: Homo sapiens

<400> SEQUENCE: 194

His Gln Glu Glu Tyr Val Arg Phe Asp Ser Asp Val Gly Glu Tyr Arg
1               5                   10                  15

<210> SEQ ID NO 195
<211> LENGTH: 17
<212> TYPE: PRT
<213> ORGANISM: Homo sapiens

<400> SEQUENCE: 195

His Gln Glu Glu Tyr Val Arg Phe Asp Ser Asp Val Gly Glu Tyr Arg
1               5                   10                  15

Ala
```

```
<210> SEQ ID NO 196
<211> LENGTH: 18
<212> TYPE: PRT
<213> ORGANISM: Homo sapiens

<400> SEQUENCE: 196

His Gln Glu Glu Tyr Val Arg Phe Asp Ser Asp Val Gly Glu Tyr Arg
1               5                   10                  15

Ala Val

<210> SEQ ID NO 197
<211> LENGTH: 15
<212> TYPE: PRT
<213> ORGANISM: Homo sapiens

<400> SEQUENCE: 197

Gln Glu Glu Tyr Val Arg Phe Asp Ser Asp Val Gly Glu Tyr Arg
1               5                   10                  15

<210> SEQ ID NO 198
<211> LENGTH: 11
<212> TYPE: PRT
<213> ORGANISM: Homo sapiens

<400> SEQUENCE: 198

Tyr Val Arg Phe Asp Ser Asp Val Gly Glu Tyr
1               5                   10

<210> SEQ ID NO 199
<211> LENGTH: 17
<212> TYPE: PRT
<213> ORGANISM: Homo sapiens

<400> SEQUENCE: 199

Asp Leu Arg Ser Trp Thr Ala Val Asp Thr Ala Ala Gln Ile Ser Glu
1               5                   10                  15

Gln

<210> SEQ ID NO 200
<211> LENGTH: 14
<212> TYPE: PRT
<213> ORGANISM: Homo sapiens

<400> SEQUENCE: 200

Leu Arg Ser Trp Thr Ala Val Asp Thr Ala Ala Gln Ile Ser
1               5                   10

<210> SEQ ID NO 201
<211> LENGTH: 16
<212> TYPE: PRT
<213> ORGANISM: Homo sapiens

<400> SEQUENCE: 201

Leu Arg Ser Trp Thr Ala Val Asp Thr Ala Ala Gln Ile Ser Glu Gln
1               5                   10                  15

<210> SEQ ID NO 202
<211> LENGTH: 20
<212> TYPE: PRT
<213> ORGANISM: Homo sapiens

<400> SEQUENCE: 202

Val Asp Asp Thr Gln Phe Val Arg Phe Asp Ser Asp Ser Ala Cys Pro
```

```
                1               5                  10                 15

Arg Met Glu Pro
            20

<210> SEQ ID NO 203
<211> LENGTH: 24
<212> TYPE: PRT
<213> ORGANISM: Homo sapiens

<400> SEQUENCE: 203

Tyr Val Asp Asp Thr Gln Phe Val Arg Phe Asp Ser Asp Ser Ala Cys
1               5                  10                 15

Pro Arg Met Glu Pro Arg Ala Pro
            20

<210> SEQ ID NO 204
<211> LENGTH: 15
<212> TYPE: PRT
<213> ORGANISM: Homo sapiens

<400> SEQUENCE: 204

Ala Ile Pro Phe Val Ile Glu Lys Ala Val Arg Ser Ser Ile Tyr
1               5                  10                 15

<210> SEQ ID NO 205
<211> LENGTH: 16
<212> TYPE: PRT
<213> ORGANISM: Homo sapiens

<400> SEQUENCE: 205

Ala Ile Pro Phe Val Ile Glu Lys Ala Val Arg Ser Ser Ile Tyr Gly
1               5                  10                 15

<210> SEQ ID NO 206
<211> LENGTH: 16
<212> TYPE: PRT
<213> ORGANISM: Homo sapiens

<400> SEQUENCE: 206

Asn Val Leu Arg Ile Ile Asn Glu Pro Thr Ala Ala Ile Ala Tyr
1               5                  10                 15

<210> SEQ ID NO 207
<211> LENGTH: 12
<212> TYPE: PRT
<213> ORGANISM: Homo sapiens

<400> SEQUENCE: 207

Arg Ile Ile Asn Glu Pro Thr Ala Ala Ala Ile Ala
1               5                  10

<210> SEQ ID NO 208
<211> LENGTH: 14
<212> TYPE: PRT
<213> ORGANISM: Homo sapiens

<400> SEQUENCE: 208

Arg Ile Ile Asn Glu Pro Thr Ala Ala Ala Ile Ala Tyr Gly
1               5                  10

<210> SEQ ID NO 209
<211> LENGTH: 14
<212> TYPE: PRT
```

<400> SEQUENCE: 209

Val Leu Arg Ile Ile Asn Glu Pro Thr Ala Ala Ala Ile Ala
1               5                   10

<210> SEQ ID NO 210
<211> LENGTH: 15
<212> TYPE: PRT
<213> ORGANISM: Homo sapiens

<400> SEQUENCE: 210

Val Leu Arg Ile Ile Asn Glu Pro Thr Ala Ala Ala Ile Ala Tyr
1               5                   10                  15

<210> SEQ ID NO 211
<211> LENGTH: 16
<212> TYPE: PRT
<213> ORGANISM: Homo sapiens

<400> SEQUENCE: 211

Val Leu Arg Ile Ile Asn Glu Pro Thr Ala Ala Ala Ile Ala Tyr Gly
1               5                   10                  15

<210> SEQ ID NO 212
<211> LENGTH: 16
<212> TYPE: PRT
<213> ORGANISM: Homo sapiens

<400> SEQUENCE: 212

Val Met Arg Ile Ile Asn Glu Pro Thr Ala Ala Ala Ile Ala Tyr Gly
1               5                   10                  15

<210> SEQ ID NO 213
<211> LENGTH: 20
<212> TYPE: PRT
<213> ORGANISM: Homo sapiens

<400> SEQUENCE: 213

Val Pro Thr Lys Lys Ser Gln Ile Phe Ser Thr Ala Ser Asp Asn Gln
1               5                   10                  15

Pro Thr Val Thr
            20

<210> SEQ ID NO 214
<211> LENGTH: 16
<212> TYPE: PRT
<213> ORGANISM: Homo sapiens

<400> SEQUENCE: 214

Gly Glu Arg Ala Met Thr Lys Asp Asn Asn Leu Leu Gly Arg Phe Glu
1               5                   10                  15

<210> SEQ ID NO 215
<211> LENGTH: 16
<212> TYPE: PRT
<213> ORGANISM: Homo sapiens

<400> SEQUENCE: 215

Glu Arg Ala Met Thr Lys Asp Asn Asn Leu Leu Gly Lys Phe Glu Leu
1               5                   10                  15

<210> SEQ ID NO 216
<211> LENGTH: 16
<212> TYPE: PRT

```
<400> SEQUENCE: 216

Gly Glu Arg Ala Met Thr Lys Asp Asn Asn Leu Leu Gly Lys Phe Glu
1               5                   10                  15

<210> SEQ ID NO 217
<211> LENGTH: 17
<212> TYPE: PRT
<213> ORGANISM: Homo sapiens

<400> SEQUENCE: 217

Gly Glu Arg Ala Met Thr Lys Asp Asn Asn Leu Leu Gly Lys Phe Glu
1               5                   10                  15

Leu

<210> SEQ ID NO 218
<211> LENGTH: 15
<212> TYPE: PRT
<213> ORGANISM: Homo sapiens

<400> SEQUENCE: 218

Gly Ile Leu Asn Val Ser Ala Val Asp Lys Ser Thr Gly Lys Glu
1               5                   10                  15

<210> SEQ ID NO 219
<211> LENGTH: 14
<212> TYPE: PRT
<213> ORGANISM: Homo sapiens

<400> SEQUENCE: 219

Arg Ala Met Thr Lys Asp Asn Asn Leu Leu Gly Lys Phe Glu
1               5                   10

<210> SEQ ID NO 220
<211> LENGTH: 13
<212> TYPE: PRT
<213> ORGANISM: Homo sapiens

<400> SEQUENCE: 220

Ile Pro Ile Ile Ile His Pro Ile Asp Arg Ser Val Asp
1               5                   10

<210> SEQ ID NO 221
<211> LENGTH: 14
<212> TYPE: PRT
<213> ORGANISM: Homo sapiens

<400> SEQUENCE: 221

Asp Arg Lys Met Val Gly Asp Val Thr Gly Ala Gln Ala Tyr
1               5                   10

<210> SEQ ID NO 222
<211> LENGTH: 15
<212> TYPE: PRT
<213> ORGANISM: Homo sapiens

<400> SEQUENCE: 222

Asp Arg Lys Met Val Gly Asp Val Thr Gly Ala Gln Ala Tyr Ala
1               5                   10                  15

<210> SEQ ID NO 223
<211> LENGTH: 14
<212> TYPE: PRT
<213> ORGANISM: Homo sapiens
```

<400> SEQUENCE: 223

Leu Gly Phe Ile Ala Phe Ala Tyr Ser Val Lys Ser Arg Asp
1               5                   10

<210> SEQ ID NO 224
<211> LENGTH: 15
<212> TYPE: PRT
<213> ORGANISM: Homo sapiens

<400> SEQUENCE: 224

Leu Ile Thr Phe Leu Cys Asp Arg Asp Ala Gly Val Gly Phe Pro
1               5                   10                  15

<210> SEQ ID NO 225
<211> LENGTH: 16
<212> TYPE: PRT
<213> ORGANISM: Homo sapiens

<400> SEQUENCE: 225

Leu Ile Thr Phe Leu Cys Asp Arg Asp Ala Gly Val Gly Phe Pro Glu
1               5                   10                  15

<210> SEQ ID NO 226
<211> LENGTH: 17
<212> TYPE: PRT
<213> ORGANISM: Homo sapiens

<400> SEQUENCE: 226

Lys Asn Thr Leu Tyr Leu Gln Met Asn Ser Leu Lys Thr Glu Asp Thr
1               5                   10                  15

Ala

<210> SEQ ID NO 227
<211> LENGTH: 15
<212> TYPE: PRT
<213> ORGANISM: Homo sapiens

<400> SEQUENCE: 227

Asn Thr Leu Tyr Leu Gln Met Asn Ser Leu Lys Thr Glu Asp Thr
1               5                   10                  15

<210> SEQ ID NO 228
<211> LENGTH: 16
<212> TYPE: PRT
<213> ORGANISM: Homo sapiens

<400> SEQUENCE: 228

Asn Thr Leu Tyr Leu Gln Met Asn Ser Leu Lys Thr Glu Asp Thr Ala
1               5                   10                  15

<210> SEQ ID NO 229
<211> LENGTH: 13
<212> TYPE: PRT
<213> ORGANISM: Homo sapiens

<400> SEQUENCE: 229

Thr Leu Tyr Leu Gln Met Asn Ser Leu Lys Thr Glu Asp
1               5                   10

<210> SEQ ID NO 230
<211> LENGTH: 14
<212> TYPE: PRT
<213> ORGANISM: Homo sapiens

<400> SEQUENCE: 230

Thr Leu Tyr Leu Gln Met Asn Ser Leu Lys Thr Glu Asp Thr
1               5                   10

<210> SEQ ID NO 231
<211> LENGTH: 15
<212> TYPE: PRT
<213> ORGANISM: Homo sapiens

<400> SEQUENCE: 231

Thr Leu Tyr Leu Gln Met Asn Ser Leu Lys Thr Glu Asp Thr Ala
1               5                   10                  15

<210> SEQ ID NO 232
<211> LENGTH: 12
<212> TYPE: PRT
<213> ORGANISM: Homo sapiens

<400> SEQUENCE: 232

Tyr Leu Gln Met Asn Ser Leu Lys Thr Glu Asp Thr
1               5                   10

<210> SEQ ID NO 233
<211> LENGTH: 21
<212> TYPE: PRT
<213> ORGANISM: Homo sapiens

<400> SEQUENCE: 233

Glu Ser Gly Pro Thr Thr Tyr Lys Val Thr Ser Thr Leu Thr Ile Lys
1               5                   10                  15

Glu Ser Asp Trp Leu
            20

<210> SEQ ID NO 234
<211> LENGTH: 14
<212> TYPE: PRT
<213> ORGANISM: Homo sapiens

<400> SEQUENCE: 234

Gly Pro Thr Thr Tyr Lys Val Thr Ser Thr Leu Thr Ile Lys
1               5                   10

<210> SEQ ID NO 235
<211> LENGTH: 15
<212> TYPE: PRT
<213> ORGANISM: Homo sapiens

<400> SEQUENCE: 235

Gly Pro Thr Thr Tyr Lys Val Thr Ser Thr Leu Thr Ile Lys Glu
1               5                   10                  15

<210> SEQ ID NO 236
<211> LENGTH: 15
<212> TYPE: PRT
<213> ORGANISM: Homo sapiens

<400> SEQUENCE: 236

Ser Gly Pro Thr Thr Tyr Lys Val Thr Ser Thr Leu Thr Ile Lys
1               5                   10                  15

<210> SEQ ID NO 237
<211> LENGTH: 20
<212> TYPE: PRT
<213> ORGANISM: Homo sapiens

<400> SEQUENCE: 237

```
Ser Gly Pro Thr Thr Tyr Lys Val Thr Ser Thr Leu Thr Ile Lys Glu
1               5                   10                  15

Ser Asp Trp Leu
            20

<210> SEQ ID NO 238
<211> LENGTH: 13
<212> TYPE: PRT
<213> ORGANISM: Homo sapiens

<400> SEQUENCE: 238

Glu Pro Arg Arg Tyr Gly Ser Ala Ala Ala Leu Pro Ser
1               5                   10

<210> SEQ ID NO 239
<211> LENGTH: 15
<212> TYPE: PRT
<213> ORGANISM: Homo sapiens

<400> SEQUENCE: 239

His Lys Ser Tyr Ser Cys Gln Val Thr His Glu Gly Ser Thr Val
1               5                   10                  15

<210> SEQ ID NO 240
<211> LENGTH: 16
<212> TYPE: PRT
<213> ORGANISM: Homo sapiens

<400> SEQUENCE: 240

His Lys Ser Tyr Ser Cys Gln Val Thr His Glu Gly Ser Thr Val Glu
1               5                   10                  15

<210> SEQ ID NO 241
<211> LENGTH: 18
<212> TYPE: PRT
<213> ORGANISM: Homo sapiens

<400> SEQUENCE: 241

Lys Ser His Lys Ser Tyr Ser Cys Gln Val Thr His Glu Gly Ser Thr
1               5                   10                  15

Val Glu

<210> SEQ ID NO 242
<211> LENGTH: 13
<212> TYPE: PRT
<213> ORGANISM: Homo sapiens

<400> SEQUENCE: 242

Lys Ser Tyr Ser Cys Gln Val Thr His Glu Gly Ser Thr
1               5                   10

<210> SEQ ID NO 243
<211> LENGTH: 14
<212> TYPE: PRT
<213> ORGANISM: Homo sapiens

<400> SEQUENCE: 243

Lys Ser Tyr Ser Cys Gln Val Thr His Glu Gly Ser Thr Val
1               5                   10

<210> SEQ ID NO 244
<211> LENGTH: 15
<212> TYPE: PRT
<213> ORGANISM: Homo sapiens
```

```
<400> SEQUENCE: 244

Lys Ser Tyr Ser Cys Gln Val Thr His Glu Gly Ser Thr Val Glu
1               5                   10                  15

<210> SEQ ID NO 245
<211> LENGTH: 16
<212> TYPE: PRT
<213> ORGANISM: Homo sapiens

<400> SEQUENCE: 245

Lys Ser Tyr Ser Cys Gln Val Thr His Glu Gly Ser Thr Val Glu Lys
1               5                   10                  15

<210> SEQ ID NO 246
<211> LENGTH: 15
<212> TYPE: PRT
<213> ORGANISM: Homo sapiens

<400> SEQUENCE: 246

Ser His Lys Ser Tyr Ser Cys Gln Val Thr His Glu Gly Ser Thr
1               5                   10                  15

<210> SEQ ID NO 247
<211> LENGTH: 16
<212> TYPE: PRT
<213> ORGANISM: Homo sapiens

<400> SEQUENCE: 247

Ser His Lys Ser Tyr Ser Cys Gln Val Thr His Glu Gly Ser Thr Val
1               5                   10                  15

<210> SEQ ID NO 248
<211> LENGTH: 17
<212> TYPE: PRT
<213> ORGANISM: Homo sapiens

<400> SEQUENCE: 248

Ser His Lys Ser Tyr Ser Cys Gln Val Thr His Glu Gly Ser Thr Val
1               5                   10                  15

Glu

<210> SEQ ID NO 249
<211> LENGTH: 19
<212> TYPE: PRT
<213> ORGANISM: Homo sapiens

<400> SEQUENCE: 249

Ser His Lys Ser Tyr Ser Cys Gln Val Thr His Glu Gly Ser Thr Val
1               5                   10                  15

Glu Lys Thr

<210> SEQ ID NO 250
<211> LENGTH: 23
<212> TYPE: PRT
<213> ORGANISM: Homo sapiens

<400> SEQUENCE: 250

Thr Pro Glu Gln Trp Lys Ser His Lys Ser Tyr Ser Cys Gln Val Thr
1               5                   10                  15

His Glu Gly Ser Thr Val Glu
            20
```

```
<210> SEQ ID NO 251
<211> LENGTH: 15
<212> TYPE: PRT
<213> ORGANISM: Homo sapiens

<400> SEQUENCE: 251

Ile Glu Val Trp Val Glu Ala Glu Asn Ala Leu Gly Lys Val Thr
1               5                   10                  15

<210> SEQ ID NO 252
<211> LENGTH: 17
<212> TYPE: PRT
<213> ORGANISM: Homo sapiens

<400> SEQUENCE: 252

Tyr Pro Ser His Ser Phe Ile Gly Glu Glu Ser Val Ala Ala Gly Glu
1               5                   10                  15

Lys

<210> SEQ ID NO 253
<211> LENGTH: 16
<212> TYPE: PRT
<213> ORGANISM: Homo sapiens

<400> SEQUENCE: 253

Asp Thr Gly Ser Tyr Arg Ala Gln Ile Ser Thr Lys Thr Ser Ala Lys
1               5                   10                  15

<210> SEQ ID NO 254
<211> LENGTH: 14
<212> TYPE: PRT
<213> ORGANISM: Homo sapiens

<400> SEQUENCE: 254

Phe Ser Gln Phe Leu Gly Asp Pro Val Glu Lys Ala Ala Gln
1               5                   10

<210> SEQ ID NO 255
<211> LENGTH: 15
<212> TYPE: PRT
<213> ORGANISM: Homo sapiens

<400> SEQUENCE: 255

Leu Pro Ser Tyr Glu Glu Ala Leu Ser Leu Pro Ser Lys Thr Pro
1               5                   10                  15

<210> SEQ ID NO 256
<211> LENGTH: 16
<212> TYPE: PRT
<213> ORGANISM: Homo sapiens

<400> SEQUENCE: 256

Leu Pro Ser Tyr Glu Glu Ala Leu Ser Leu Pro Ser Lys Thr Pro Glu
1               5                   10                  15

<210> SEQ ID NO 257
<211> LENGTH: 17
<212> TYPE: PRT
<213> ORGANISM: Homo sapiens

<400> SEQUENCE: 257

Leu Pro Ser Tyr Glu Glu Ala Leu Ser Leu Pro Ser Lys Thr Pro Glu
1               5                   10                  15

Gly
```

```
<210> SEQ ID NO 258
<211> LENGTH: 18
<212> TYPE: PRT
<213> ORGANISM: Homo sapiens

<400> SEQUENCE: 258

Val Val Leu Pro Ser Tyr Glu Glu Ala Leu Ser Leu Pro Ser Lys Thr
1               5                   10                  15
Pro Glu

<210> SEQ ID NO 259
<211> LENGTH: 15
<212> TYPE: PRT
<213> ORGANISM: Homo sapiens

<400> SEQUENCE: 259

Gly Val Pro Lys Asp Tyr Thr Gly Glu Asp Val Thr Pro Gln Asn
1               5                   10                  15

<210> SEQ ID NO 260
<211> LENGTH: 14
<212> TYPE: PRT
<213> ORGANISM: Homo sapiens

<400> SEQUENCE: 260

Val Pro Lys Asp Tyr Thr Gly Glu Asp Val Thr Pro Gln Asn
1               5                   10

<210> SEQ ID NO 261
<211> LENGTH: 17
<212> TYPE: PRT
<213> ORGANISM: Homo sapiens

<400> SEQUENCE: 261

Asp Val Arg Lys Leu Tyr Trp Leu Met Lys Ser Ser Leu Asn Gly Asp
1               5                   10                  15
Asn

<210> SEQ ID NO 262
<211> LENGTH: 14
<212> TYPE: PRT
<213> ORGANISM: Homo sapiens

<400> SEQUENCE: 262

Lys Pro Thr Ile Cys Ser Asp Gln Asp Asn Tyr Cys Val Thr
1               5                   10

<210> SEQ ID NO 263
<211> LENGTH: 15
<212> TYPE: PRT
<213> ORGANISM: Homo sapiens

<400> SEQUENCE: 263

Leu Lys Pro Thr Ile Cys Ser Asp Gln Asp Asn Tyr Cys Val Thr
1               5                   10                  15

<210> SEQ ID NO 264
<211> LENGTH: 15
<212> TYPE: PRT
<213> ORGANISM: Homo sapiens

<400> SEQUENCE: 264

His Pro Pro Glu Leu Leu Phe Ser Ala Ser Leu Pro Ala Leu Gly
1               5                   10                  15
```

```
<210> SEQ ID NO 265
<211> LENGTH: 15
<212> TYPE: PRT
<213> ORGANISM: Homo sapiens

<400> SEQUENCE: 265

Val Asp Tyr Phe Leu Asn Val Ala Thr Ala Gln Gly Arg Tyr Tyr
1               5                   10                  15

<210> SEQ ID NO 266
<211> LENGTH: 17
<212> TYPE: PRT
<213> ORGANISM: Homo sapiens

<400> SEQUENCE: 266

Thr Pro Ile Ser Glu Val Tyr Glu Ser Glu Lys Asp Glu Asp Gly Phe
1               5                   10                  15

Leu

<210> SEQ ID NO 267
<211> LENGTH: 18
<212> TYPE: PRT
<213> ORGANISM: Homo sapiens

<400> SEQUENCE: 267

Thr Pro Ile Ser Glu Val Tyr Glu Ser Glu Lys Asp Glu Asp Gly Phe
1               5                   10                  15

Leu Tyr

<210> SEQ ID NO 268
<211> LENGTH: 16
<212> TYPE: PRT
<213> ORGANISM: Homo sapiens

<400> SEQUENCE: 268

Ser Pro Asp Arg Val Tyr Ile Asn Tyr Tyr Asp Met Asn Ala Ala Asn
1               5                   10                  15

<210> SEQ ID NO 269
<211> LENGTH: 15
<212> TYPE: PRT
<213> ORGANISM: Homo sapiens

<400> SEQUENCE: 269

Val Pro Asp Gly Phe Leu Ser Glu Leu Thr Gln Gln Leu Ala Gln
1               5                   10                  15

<210> SEQ ID NO 270
<211> LENGTH: 15
<212> TYPE: PRT
<213> ORGANISM: Homo sapiens

<400> SEQUENCE: 270

Asp Gly Arg Thr Phe Tyr Ile Asp His Asn Ser Lys Ile Thr Gln
1               5                   10                  15

<210> SEQ ID NO 271
<211> LENGTH: 15
<212> TYPE: PRT
<213> ORGANISM: Homo sapiens

<400> SEQUENCE: 271

Gly Pro Val Gly Val Phe Glu Trp Glu Ala Phe Ala Arg Gly Thr
```

```
                1               5                10              15

<210> SEQ ID NO 272
<211> LENGTH: 14
<212> TYPE: PRT
<213> ORGANISM: Homo sapiens

<400> SEQUENCE: 272

Arg Val Val Met Arg Val Asp Phe Asn Val Pro Met Lys Asn
1               5                   10

<210> SEQ ID NO 273
<211> LENGTH: 18
<212> TYPE: PRT
<213> ORGANISM: Homo sapiens

<400> SEQUENCE: 273

Ser Pro Asp Asp Lys Tyr Ile Tyr Val Ala Asp Ile Leu Ala His Glu
1               5                   10                  15

Ile His

<210> SEQ ID NO 274
<211> LENGTH: 15
<212> TYPE: PRT
<213> ORGANISM: Homo sapiens

<400> SEQUENCE: 274

Leu Pro Gly Leu Ala Lys Gln Pro Ser Phe Arg Gln Tyr Ser Gly
1               5                   10                  15

<210> SEQ ID NO 275
<211> LENGTH: 16
<212> TYPE: PRT
<213> ORGANISM: Homo sapiens

<400> SEQUENCE: 275

Val Ser Phe Glu Leu Phe Ala Asp Lys Val Pro Lys Thr Ala Glu Asn
1               5                   10                  15

<210> SEQ ID NO 276
<211> LENGTH: 14
<212> TYPE: PRT
<213> ORGANISM: Homo sapiens

<400> SEQUENCE: 276

Gly Pro Ser Tyr Trp Cys Gln Asn Thr Glu Thr Ala Ala Gln
1               5                   10

<210> SEQ ID NO 277
<211> LENGTH: 15
<212> TYPE: PRT
<213> ORGANISM: Homo sapiens

<400> SEQUENCE: 277

Val Pro Gly Phe Ala Asp Asp Pro Thr Glu Leu Ala Cys Arg Val
1               5                   10                  15

<210> SEQ ID NO 278
<211> LENGTH: 15
<212> TYPE: PRT
<213> ORGANISM: Homo sapiens

<400> SEQUENCE: 278

Gly Ala Leu Leu Val Tyr Asp Ile Thr Ser Arg Glu Thr Tyr Asn
1               5                   10                  15
```

```
<210> SEQ ID NO 279
<211> LENGTH: 15
<212> TYPE: PRT
<213> ORGANISM: Homo sapiens

<400> SEQUENCE: 279

Leu Ile Pro Ser Tyr Ile Arg Asp Ser Thr Val Ala Val Val Val
1               5                   10                  15

<210> SEQ ID NO 280
<211> LENGTH: 17
<212> TYPE: PRT
<213> ORGANISM: Homo sapiens

<400> SEQUENCE: 280

Phe Pro Glu Pro Ile Lys Leu Asp Lys Asn Asp Arg Ala Lys Ala Ser
1               5                   10                  15

Ala

<210> SEQ ID NO 281
<211> LENGTH: 14
<212> TYPE: PRT
<213> ORGANISM: Homo sapiens

<400> SEQUENCE: 281

Ala Phe Phe Thr Leu Ala Arg Asp Ile Lys Ala Lys Met Asp
1               5                   10

<210> SEQ ID NO 282
<211> LENGTH: 15
<212> TYPE: PRT
<213> ORGANISM: Homo sapiens

<400> SEQUENCE: 282

Asn Ala Phe Phe Thr Leu Ala Arg Asp Ile Lys Ala Lys Met Asp
1               5                   10                  15

<210> SEQ ID NO 283
<211> LENGTH: 12
<212> TYPE: PRT
<213> ORGANISM: Homo sapiens

<400> SEQUENCE: 283

Leu Leu Gln Gln Ile Ser Gln His Gln Glu His Phe
1               5                   10

<210> SEQ ID NO 284
<211> LENGTH: 14
<212> TYPE: PRT
<213> ORGANISM: Homo sapiens

<400> SEQUENCE: 284

Thr Glu Gln Phe Thr Ala Met Arg Asp Leu Tyr Met Lys Asn
1               5                   10

<210> SEQ ID NO 285
<211> LENGTH: 16
<212> TYPE: PRT
<213> ORGANISM: Homo sapiens

<400> SEQUENCE: 285

Ile Pro Ser Val Phe Ile Gly Glu Ser Ser Ala Asn Ser Leu Lys Asp
1               5                   10                  15
```

```
<210> SEQ ID NO 286
<211> LENGTH: 16
<212> TYPE: PRT
<213> ORGANISM: Homo sapiens

<400> SEQUENCE: 286

Ala Asp Arg Asp Thr Tyr Arg Arg Ser Ala Val Pro Pro Gly Ala Asp
1               5                   10                  15

<210> SEQ ID NO 287
<211> LENGTH: 15
<212> TYPE: PRT
<213> ORGANISM: Homo sapiens

<400> SEQUENCE: 287

Asp Arg Asp Thr Tyr Arg Arg Ser Ala Val Pro Pro Gly Ala Asp
1               5                   10                  15

<210> SEQ ID NO 288
<211> LENGTH: 14
<212> TYPE: PRT
<213> ORGANISM: Homo sapiens

<400> SEQUENCE: 288

Arg Asp Thr Tyr Arg Arg Ser Ala Val Pro Pro Gly Ala Asp
1               5                   10

<210> SEQ ID NO 289
<211> LENGTH: 14
<212> TYPE: PRT
<213> ORGANISM: Homo sapiens

<400> SEQUENCE: 289

Leu Pro Pro Asn Trp Lys Tyr Glu Ser Ser Thr Ala Ser Ala
1               5                   10

<210> SEQ ID NO 290
<211> LENGTH: 15
<212> TYPE: PRT
<213> ORGANISM: Homo sapiens

<400> SEQUENCE: 290

Arg Thr Phe His Arg Ala Ala Ser Ser Ala Ala Gln Gly Ala Phe
1               5                   10                  15

<210> SEQ ID NO 291
<211> LENGTH: 15
<212> TYPE: PRT
<213> ORGANISM: Homo sapiens

<400> SEQUENCE: 291

Ser Arg Thr Phe His Arg Ala Ala Ser Ser Ala Ala Gln Gly Ala
1               5                   10                  15

<210> SEQ ID NO 292
<211> LENGTH: 16
<212> TYPE: PRT
<213> ORGANISM: Homo sapiens

<400> SEQUENCE: 292

Ser Ser Arg Thr Phe His Arg Ala Ala Ser Ser Ala Ala Gln Gly Ala
1               5                   10                  15

<210> SEQ ID NO 293
<211> LENGTH: 17
```

-continued

```
<212> TYPE: PRT
<213> ORGANISM: Homo sapiens

<400> SEQUENCE: 293

Ser Ser Arg Thr Phe His Arg Ala Ala Ser Ser Ala Ala Gln Gly Ala
1               5                   10                  15

Phe

<210> SEQ ID NO 294
<211> LENGTH: 14
<212> TYPE: PRT
<213> ORGANISM: Homo sapiens

<400> SEQUENCE: 294

Tyr Gly Ser Tyr Ser Thr Gln Ala Ser Ala Ala Ala Ala Thr
1               5                   10

<210> SEQ ID NO 295
<211> LENGTH: 15
<212> TYPE: PRT
<213> ORGANISM: Homo sapiens

<400> SEQUENCE: 295

Tyr Gly Ser Tyr Ser Thr Gln Ala Ser Ala Ala Ala Ala Thr Ala
1               5                   10                  15

<210> SEQ ID NO 296
<211> LENGTH: 16
<212> TYPE: PRT
<213> ORGANISM: Homo sapiens

<400> SEQUENCE: 296

Tyr Gly Ser Tyr Ser Thr Gln Ala Ser Ala Ala Ala Ala Thr Ala Glu
1               5                   10                  15

<210> SEQ ID NO 297
<211> LENGTH: 14
<212> TYPE: PRT
<213> ORGANISM: Homo sapiens

<400> SEQUENCE: 297

Val Pro Met Tyr Ile Gly Glu Ile Ser Pro Thr Ala Leu Arg
1               5                   10

<210> SEQ ID NO 298
<211> LENGTH: 12
<212> TYPE: PRT
<213> ORGANISM: Homo sapiens

<400> SEQUENCE: 298

Ile Ser Ile Tyr Ser Ser Glu Arg Ser Val Leu Gln
1               5                   10

<210> SEQ ID NO 299
<211> LENGTH: 18
<212> TYPE: PRT
<213> ORGANISM: Homo sapiens

<400> SEQUENCE: 299

Val Ala Ala Val Phe Ile Ala Gln Leu Ser Gln Gln Ser Leu Asp Phe
1               5                   10                  15

Val Lys

<210> SEQ ID NO 300
```

```
<211> LENGTH: 17
<212> TYPE: PRT
<213> ORGANISM: Homo sapiens

<400> SEQUENCE: 300

Thr Gly Ala Leu Tyr Arg Ile Gly Asp Leu Gln Ala Phe Gln Gly His
1               5                   10                  15

Gly

<210> SEQ ID NO 301
<211> LENGTH: 14
<212> TYPE: PRT
<213> ORGANISM: Homo sapiens

<400> SEQUENCE: 301

Asp Tyr Tyr Lys Gly Glu Glu Ser Asn Ser Ser Ala Asn Lys
1               5                   10

<210> SEQ ID NO 302
<211> LENGTH: 15
<212> TYPE: PRT
<213> ORGANISM: Homo sapiens

<400> SEQUENCE: 302

Lys Pro Gly Ile Tyr Arg Ser Asn Met Asp Gly Ser Ala Ala Tyr
1               5                   10                  15

<210> SEQ ID NO 303
<211> LENGTH: 18
<212> TYPE: PRT
<213> ORGANISM: Homo sapiens

<400> SEQUENCE: 303

Arg His Pro Ile Asn Glu Tyr Tyr Ile Ala Asp Ala Ser Glu Asp Gln
1               5                   10                  15

Val Phe

<210> SEQ ID NO 304
<211> LENGTH: 15
<212> TYPE: PRT
<213> ORGANISM: Homo sapiens

<400> SEQUENCE: 304

Asn Pro Arg Lys Phe Asn Leu Asp Ala Thr Glu Leu Ser Ile Arg
1               5                   10                  15

<210> SEQ ID NO 305
<211> LENGTH: 16
<212> TYPE: PRT
<213> ORGANISM: Homo sapiens

<400> SEQUENCE: 305

Asn Pro Arg Lys Phe Asn Leu Asp Ala Thr Glu Leu Ser Ile Arg Lys
1               5                   10                  15

<210> SEQ ID NO 306
<211> LENGTH: 17
<212> TYPE: PRT
<213> ORGANISM: Homo sapiens

<400> SEQUENCE: 306

Asn Pro Arg Lys Phe Asn Leu Asp Ala Thr Glu Leu Ser Ile Arg Lys
1               5                   10                  15

Ala
```

```
<210> SEQ ID NO 307
<211> LENGTH: 17
<212> TYPE: PRT
<213> ORGANISM: Homo sapiens

<400> SEQUENCE: 307

Gly Pro Pro Ile Gly Ser Phe Thr Leu Ile Asp Ser Glu Val Ser Gln
1               5                   10                  15

Leu

<210> SEQ ID NO 308
<211> LENGTH: 18
<212> TYPE: PRT
<213> ORGANISM: Homo sapiens

<400> SEQUENCE: 308

Asn Pro Lys Asp Val Leu Val Gly Ala Asp Ser Val Arg Ala Ala Ile
1               5                   10                  15

Thr Phe

<210> SEQ ID NO 309
<211> LENGTH: 15
<212> TYPE: PRT
<213> ORGANISM: Homo sapiens

<400> SEQUENCE: 309

His Lys Gly Glu Ile Arg Gly Ala Ser Thr Pro Phe Gln Phe Arg
1               5                   10                  15

<210> SEQ ID NO 310
<211> LENGTH: 12
<212> TYPE: PRT
<213> ORGANISM: Homo sapiens

<400> SEQUENCE: 310

Asp Val Ala Phe Val Lys Asp Gln Thr Val Ile Gln
1               5                   10

<210> SEQ ID NO 311
<211> LENGTH: 12
<212> TYPE: PRT
<213> ORGANISM: Homo sapiens

<400> SEQUENCE: 311

Phe Val Lys Asp Gln Thr Val Ile Gln Asn Thr Asp
1               5                   10

<210> SEQ ID NO 312
<211> LENGTH: 13
<212> TYPE: PRT
<213> ORGANISM: Homo sapiens

<400> SEQUENCE: 312

Gly Asp Val Ala Phe Val Lys Asp Gln Thr Val Ile Gln
1               5                   10

<210> SEQ ID NO 313
<211> LENGTH: 16
<212> TYPE: PRT
<213> ORGANISM: Homo sapiens

<400> SEQUENCE: 313

Gly Asp Val Ala Phe Val Lys Asp Gln Thr Val Ile Gln Asn Thr Asp
```

```
                1               5                   10                  15
```

<210> SEQ ID NO 314
<211> LENGTH: 15
<212> TYPE: PRT
<213> ORGANISM: Homo sapiens

<400> SEQUENCE: 314

```
Cys Pro Ser Asp Trp Lys Thr Asp Ser Thr Cys Arg Met Val Thr
1               5                   10                  15
```

<210> SEQ ID NO 315
<211> LENGTH: 16
<212> TYPE: PRT
<213> ORGANISM: Homo sapiens

<400> SEQUENCE: 315

```
Cys Pro Ser Asp Trp Lys Thr Asp Ser Thr Cys Arg Met Val Thr Ser
1               5                   10                  15
```

<210> SEQ ID NO 316
<211> LENGTH: 17
<212> TYPE: PRT
<213> ORGANISM: Homo sapiens

<400> SEQUENCE: 316

```
Cys Pro Ser Asp Trp Lys Thr Asp Ser Thr Cys Arg Met Val Thr Ser
1               5                   10                  15

Glu
```

<210> SEQ ID NO 317
<211> LENGTH: 15
<212> TYPE: PRT
<213> ORGANISM: Homo sapiens

<400> SEQUENCE: 317

```
Phe Thr Tyr Ile Asn Leu Asp Lys Ala Val Leu Gly Thr Ser Asn
1               5                   10                  15
```

<210> SEQ ID NO 318
<211> LENGTH: 14
<212> TYPE: PRT
<213> ORGANISM: Homo sapiens

<400> SEQUENCE: 318

```
Tyr Val Ala Tyr Ser Lys Ala Ala Thr Val Thr Gly Lys Leu
1               5                   10
```

<210> SEQ ID NO 319
<211> LENGTH: 13
<212> TYPE: PRT
<213> ORGANISM: Homo sapiens

<400> SEQUENCE: 319

```
Glu Ile Ile His Lys Ala Leu Ile Asp Arg Asn Ile Gln
1               5                   10
```

<210> SEQ ID NO 320
<211> LENGTH: 15
<212> TYPE: PRT
<213> ORGANISM: Homo sapiens

<400> SEQUENCE: 320

```
Gly Pro Leu Ser Trp Tyr Ser Asp Pro Gly Leu Ala Gly Val Ser
1               5                   10                  15
```

<210> SEQ ID NO 321
<211> LENGTH: 13
<212> TYPE: PRT
<213> ORGANISM: Homo sapiens

<400> SEQUENCE: 321

Leu Lys Pro Glu Phe Val Asp Ile Ile Asn Ala Lys Gln
1               5                   10

<210> SEQ ID NO 322
<211> LENGTH: 15
<212> TYPE: PRT
<213> ORGANISM: Homo sapiens

<400> SEQUENCE: 322

Gly Ser Ser Tyr Gly Ser Glu Thr Ser Ile Pro Ala Ala Ala His
1               5                   10                  15

<210> SEQ ID NO 323
<211> LENGTH: 16
<212> TYPE: PRT
<213> ORGANISM: Homo sapiens

<400> SEQUENCE: 323

Ala Lys Phe Trp Glu Val Ile Ser Asp Glu His Gly Ile Asp Pro Thr
1               5                   10                  15

<210> SEQ ID NO 324
<211> LENGTH: 12
<212> TYPE: PRT
<213> ORGANISM: Homo sapiens

<400> SEQUENCE: 324

Glu Pro Tyr Asn Ala Thr Leu Ser Val His Gln Leu
1               5                   10

<210> SEQ ID NO 325
<211> LENGTH: 14
<212> TYPE: PRT
<213> ORGANISM: Homo sapiens

<400> SEQUENCE: 325

Glu Pro Tyr Asn Ala Thr Leu Ser Val His Gln Leu Val Glu
1               5                   10

<210> SEQ ID NO 326
<211> LENGTH: 15
<212> TYPE: PRT
<213> ORGANISM: Homo sapiens

<400> SEQUENCE: 326

Asp Tyr Asn Ile Gln Lys Glu Ser Thr Leu His Leu Val Leu Arg
1               5                   10                  15

<210> SEQ ID NO 327
<211> LENGTH: 14
<212> TYPE: PRT
<213> ORGANISM: Homo sapiens

<400> SEQUENCE: 327

Ser Asp Tyr Asn Ile Gln Lys Glu Ser Thr Leu His Leu Val
1               5                   10

<210> SEQ ID NO 328

```
<211> LENGTH: 20
<212> TYPE: PRT
<213> ORGANISM: Homo sapiens

<400> SEQUENCE: 328

Asp Lys Gly Ala Phe Arg Ile Glu Ile Asn Phe Pro Ala Glu Tyr Pro
1               5                   10                  15

Phe Lys Pro Pro
            20

<210> SEQ ID NO 329
<211> LENGTH: 19
<212> TYPE: PRT
<213> ORGANISM: Homo sapiens

<400> SEQUENCE: 329

Lys Gly Ala Phe Arg Ile Glu Ile Asn Phe Pro Ala Glu Tyr Pro Phe
1               5                   10                  15

Lys Pro Pro

<210> SEQ ID NO 330
<211> LENGTH: 24
<212> TYPE: PRT
<213> ORGANISM: Homo sapiens

<400> SEQUENCE: 330

Asn Pro Pro Tyr Asp Lys Gly Ala Phe Arg Ile Glu Ile Asn Phe Pro
1               5                   10                  15

Ala Glu Tyr Pro Phe Lys Pro Pro
            20

<210> SEQ ID NO 331
<211> LENGTH: 23
<212> TYPE: PRT
<213> ORGANISM: Homo sapiens

<400> SEQUENCE: 331

Pro Pro Tyr Asp Lys Gly Ala Phe Arg Ile Glu Ile Asn Phe Pro Ala
1               5                   10                  15

Glu Tyr Pro Phe Lys Pro Pro
            20

<210> SEQ ID NO 332
<211> LENGTH: 15
<212> TYPE: PRT
<213> ORGANISM: Homo sapiens

<400> SEQUENCE: 332

Asn Pro Asp Thr Leu Ser Ala Met Ser Asn Pro Arg Ala Met Gln
1               5                   10                  15

<210> SEQ ID NO 333
<211> LENGTH: 15
<212> TYPE: PRT
<213> ORGANISM: Homo sapiens

<400> SEQUENCE: 333

Gln Leu Ile Tyr Ile Pro Leu Pro Asp Glu Lys Ser Arg Val Ala
1               5                   10                  15

<210> SEQ ID NO 334
<211> LENGTH: 14
<212> TYPE: PRT
<213> ORGANISM: Homo sapiens
```

-continued

```
<400> SEQUENCE: 334

Ala Ala Lys Tyr Gln Leu Asp Pro Thr Ala Ser Ile Ser Ala
1               5                   10

<210> SEQ ID NO 335
<211> LENGTH: 18
<212> TYPE: PRT
<213> ORGANISM: Homo sapiens

<400> SEQUENCE: 335

Asp Pro Asp Pro Glu Asp Phe Ala Asp Glu Gln Ser Leu Val Gly Arg
1               5                   10                  15

Phe Ile

<210> SEQ ID NO 336
<211> LENGTH: 16
<212> TYPE: PRT
<213> ORGANISM: Homo sapiens

<400> SEQUENCE: 336

Ala Pro Ser Gly Phe Tyr Ile Ala Ser Gly Asp Val Ser Gly Lys Leu
1               5                   10                  15

<210> SEQ ID NO 337
<211> LENGTH: 17
<212> TYPE: PRT
<213> ORGANISM: Homo sapiens

<400> SEQUENCE: 337

Ala Pro Ser Gly Phe Tyr Ile Ala Ser Gly Asp Val Ser Gly Lys Leu
1               5                   10                  15

Arg

<210> SEQ ID NO 338
<211> LENGTH: 15
<212> TYPE: PRT
<213> ORGANISM: Homo sapiens

<400> SEQUENCE: 338

Arg Ala Ser Trp Arg Ile Ile Ser Ser Ile Glu Gln Lys Glu Glu
1               5                   10                  15
```